US011014876B2

(12) United States Patent
Cogle et al.

(10) Patent No.: US 11,014,876 B2
(45) Date of Patent: May 25, 2021

(54) POLYAMINE SULFONAMIDES AND USES THEREOF

(71) Applicants: University of Florida Research Foundation, Inc., Gainesville, FL (US); Torrey Pines Institute for Molecular Studies, Port St. Lucie, FL (US)

(72) Inventors: Christopher R. Cogle, Gainesville, FL (US); Amy M. Meacham, Gainesville, FL (US); Peter P. Sayeski, Gainesville, FL (US); Marcello A. Giulianotti, Port St. Lucie, FL (US); Richard A. Houghten, Port St. Lucie, FL (US); Gregory S. Welmaker, Port St. Lucie, FL (US)

(73) Assignees: University of Florida Research Foundation, Inc., Gainesville, FL (US); Torrey Pines Institute for Molecular Studies, Port St. Lucie, FL (US)

( * ) Notice: Subject to any disclaimer, the term of this patent is extended or adjusted under 35 U.S.C. 154(b) by 0 days.

(21) Appl. No.: 15/766,680

(22) PCT Filed: Nov. 4, 2016

(86) PCT No.: PCT/US2016/060598
§ 371 (c)(1),
(2) Date: Apr. 6, 2018

(87) PCT Pub. No.: WO2017/079609
PCT Pub. Date: May 11, 2017

(65) Prior Publication Data

US 2018/0297942 A1 Oct. 18, 2018

Related U.S. Application Data

(60) Provisional application No. 62/250,983, filed on Nov. 4, 2015.

(51) Int. Cl.

| | |
|---|---|
| ***C07C 311/18*** | (2006.01) |
| ***C07C 311/05*** | (2006.01) |
| ***C07D 279/02*** | (2006.01) |
| ***A61K 31/18*** | (2006.01) |
| ***A61K 45/06*** | (2006.01) |

(52) U.S. Cl.
CPC ............ *C07C 311/18* (2013.01); *A61K 31/18* (2013.01); *A61K 45/06* (2013.01); *C07C 311/05* (2013.01); *C07D 279/02* (2013.01); *C07B 2200/07* (2013.01)

(58) Field of Classification Search
CPC .... C07C 311/18; C07C 311/05; C07D 279/02
See application file for complete search history.

(56) References Cited

FOREIGN PATENT DOCUMENTS

WO WO 2006/123020 A1 11/2006

OTHER PUBLICATIONS

STN Registry database entry for CAS RN 1844864-30-7, entry date of Jan. 11, 2016, Accessed Jul. 9, 2019.*
STN Registry database entry for CAS RN 359781-77-4, entry date of Oct. 2, 2001, Accessed Jul. 9, 2019.*
STN Registry database entry for CAS RN 155625-53-9, entry date of Jun. 9, 1994, Accessed Jul. 9, 2019.*
STN Registry database entry for CAS RN 906748-10-5, entry date of Sep. 15, 2006, Accessed Feb. 3, 2020.*
Kamioka et al., Org. Biomol. Chem., 2010, 8, pp. 2529-2536.*
O'Brien et al., Tetrahedron, 2014, , 5082-5092.*
Ottesen et al., J. Org. Chem., 2010, 75, 4983-4991.*
[No Author Listed], CID 68064388. Compound Summary. Nov. 30, 2012.
[No Author Listed], CID 90392987. Compound Summary. Feb. 13, 2015.
[No Author Listed], CID 82511689. Compound Summary. Oct. 20, 2014.
Extended European Search Report in connection with Application No. EP 16863066.3, dated Feb. 19, 2019.
Debevec et al., Libraries from Libraries: A Series of Sulfonamide Linked Heterocycles Derived from the Same Scaffold. Tetrahedron Lett. Aug. 7, 2013; 54(32):4296-99. doi: 10.1016/j.tetlet.2013.06.003.
Sudhakar et al., New chiral [N,N,N]-ligand containing titanium/zirconium precatalysts for 1-hexene polymerization. J Poly Sci. Jul. 1, 2006;44(13):4006-14. Doi: 10.1002/pola.21502.

* cited by examiner

*Primary Examiner* — Alicia L Otton
(74) *Attorney, Agent, or Firm* — Wolf, Greenfield & Sacks, P.C.

(57) ABSTRACT

Cancer is a disease for which there remains a great unmet medical need, and therefore the discovery and development of new antineoplastic agents is critically important. The present invention relates in part to new therapeutic compounds with antineoplastic activity. Provided herein are polyamine sulfonamides such as compounds of Formula (I), or pharmaceutically acceptable salts thereof, which may be used in the treatment and/or prevention of diseases such as cancer. Also provided herein are pharmaceutical compositions and kits comprising the inventive compounds. Furthermore, the present invention provides methods of treating and/or preventing diseases (e.g., cancer) using compounds of Formula (I), or pharmaceutically acceptable salts thereof or pharmaceutical compositions thereof. Other methods provided include methods for inducing apoptosis of a cell, as well as methods for inhibiting alpha-enolase enzymatic activity in vivo and in vitro.

43 Claims, 10 Drawing Sheets

POLYAMINE SULFONAMIDES AND USES THEREOF

RELATED APPLICATIONS

This application is a national stage filing under 35 U.S.C. § 371 of international PCT application, PCT/US2016/060598, filed Nov. 4, 2016, which claims priority under 35 U.S.C. § 119(e) to U.S. Provisional Application, U.S. Ser. No. 62/250,983, filed on Nov. 4, 2015, each of which is incorporated herein by reference.

BACKGROUND OF THE INVENTION

Cancer is a disease for which there remains a great unmet medical need. According to the World Health Organization, about 14.1 million new cases of cancer were diagnosed across the globe in 2012, resulting in approximately 15% of human deaths that year. See, e.g., *World Cancer Report* 2014, *World Health Organization*, Chapter 1.1. Hematological cancers are cancers that affect the blood, bone marrow, and lymphatic system, and account for approximately 10% of all cancers diagnosed in the United States. It has been estimated that one person in the United States is diagnosed with a hematological cancer every three minutes. See, e.g., *Blood Cancer Facts* 2014-2015, The Leukemia and Lymphoma Society; *Cancer Facts & Figures* 2015, *American Chemical Society,* 2015. Examples of common hematological cancers include leukemias (e.g., acute lymphoblastic leukemia (ALL), chronic lymphocytic leukemia (CLL), chronic myeloid leukemia (CML), acute myeloid leukemia (AML)), lymphomas (e.g., Hodgkin's and non-Hodgkin's lymphomas), and myelomas (e.g., multiple myeloma (MM)).

Acute myeloid leukemia (AML) is the most common leukemia in adults. AML arises from a the neoplastic transformation of hematopoietic stem and progenitor cells. This disease occurs in approximately 0.5% of the population, usually in adults over the age of 45. Although 50-70% of AML patients respond to induction chemotherapy, nearly 80% of patients will die of refractory disease. Moreover, the current treatment for AML, which hasn't changed since the 1960s, is highly toxic, requires inpatient hospitalization for 4 weeks on average, causes life-threatening side effects in 80% of patients and kills 10-20% of patients. For most patients with AML, the only cure is allogeneic hematopoietic cell transplant. However, only a small fraction of patients are eligible for transplant due to lack of suitable donor and significant co-morbidities that portend for transplant-related death. In terms of financial costs, the all-cause cost of treating AML in the United States is estimated to be in the billions of dollars each year. Given this large unmet need and high cost of treating complications of disease, new antineopastic agents are critically needed for AML and related diseases such as the myelodysplastic syndromes (MDS) and other proliferative diseases.

SUMMARY OF THE INVENTION

The greatest challenge in treating acute myeloid leukemia (AML) is refractory cases of AML, with close to 80% of patients dying of disease. Human AML cells functionally integrate within blood vessels, occasionally fusing with endothelial cells (ECs). Acute myeloid leukemia cells in close proximity to endothelial cells exit the cell cycle and consequently become more resistant to cell cycle agents such as cytarabine, azacitidine, decitabine, doxorubicin, daunorubicin, and idarubicin. In order to identify novel agents for the treatment of cancer (e.g., hematological cancers such as leukemia), a human AML-BMEC (acute myseloid leukemia-bone marrow microvascular endothelial cell) co-culture assay for high-throughput screening of agents that are selectively toxic to AML cells was developed. Using a combinatorial chemistry and positional scanning strategy, 30 million compounds were screened, and new polyamine sulfonamides with antiproliferative activity were discovered. These compounds demonstrated selective toxicity in AML cells despite attachment to BMECs (bone marrow microvascular endothelial cells). Provided herein are novel polyamine sulfonamides, such as compounds of Formula (I), which can be used for the treatment and/or prevention of proliferative diseases such as cancer.

In one aspect, the present invention provides polyamine sulfonamides such as compounds of Formula (I):

(I)

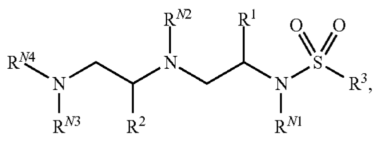

and pharmaceutically acceptable salts, hydrates, solvates, polymorphs, co-crystals, tautomers, stereoisomers, isotopically labeled derivatives, and prodrugs thereof, wherein $R^1$, $R^2$, $R^3$, $R^{N1}$, $R^{N2}$, $R^{N3}$, and $R^{N4}$ are as defined herein.

In certain embodiments of the present invention, a compound of Formula (I) is of Formula (II):

(II)

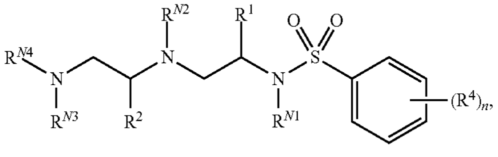

or a pharmaceutically acceptable salt, hydrate, solvate, polymorph, co-crystal, tautomer, stereoisomer, isotopically labeled derivative, or prodrug thereof, wherein n, $R^1$, $R^2$, $R^4$, $R^{N1}$, $R^{N2}$, $R^{N3}$, and $R^{N4}$ are as defined herein.

In certain embodiments, a compound of Formula (I) is of Formula (III):

(III)

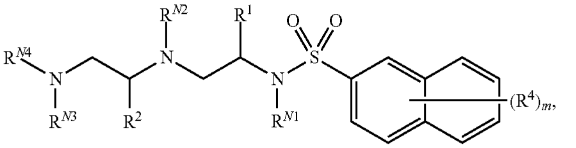

or a pharmaceutically acceptable salt, hydrate, solvate, polymorph, co-crystal, tautomer, stereoisomer, isotopically labeled derivative, or prodrug thereof, wherein m, $R^1$, $R^2$, $R^4$, $R^{N1}$, $R^{N2}$, $R^{N3}$, and $R^{N4}$ are as defined herein.

Exemplary compounds of Formula (I) include, but are not limited to, the following compounds:

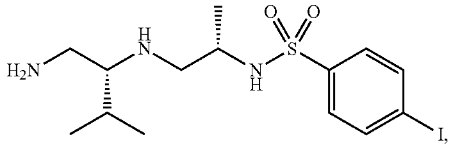
,
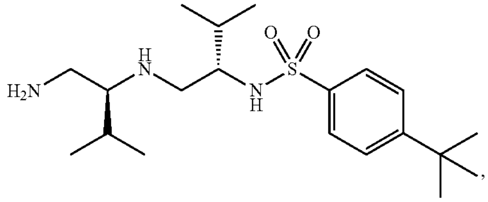
,
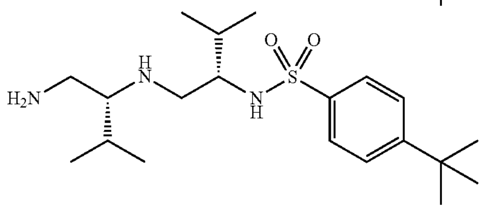
,
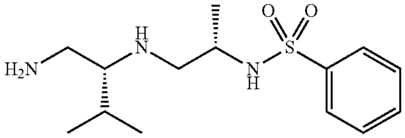
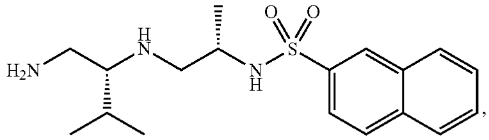
,
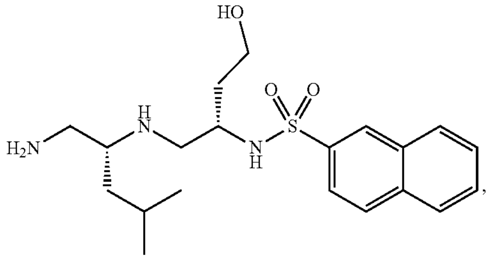
,
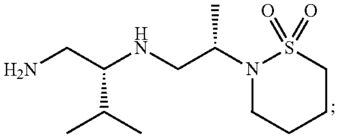
;

and pharmaceutically acceptable salts, hydrates, solvates, polymorphs, co-crystals, tautomers, stereoisomers, isotopically labeled derivatives, and prodrugs thereof.

In certain embodiments, a compound of Formula (I) is the following:

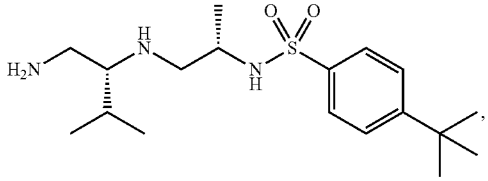 [SMILES: CC(C)[C@H](CN)NC[C@H](C)NS(=O)(=O)c1ccc(C(C)(C)C)cc1]
, or a pharmaceutically acceptable salt, hydrate, solvate, polymorph, co-crystal, tautomer, stereoisomer, isotopically labeled derivative, or prodrug thereof.

In another aspect, the present invention provides pharmaceutical compositions comprising a compound of Formula (I), or a pharmaceutically acceptable salt, hydrate, solvate, polymorph, co-crystal, tautomer, stereoisomer, isotopically labeled derivative, or prodrug thereof, and optionally a pharmaceutically acceptable excipient. In certain embodiments, the pharmaceutical compositions described herein include a therapeutically effective amount of a compound of Formula (I), or a pharmaceutically acceptable salt, solvate, hydrate, polymorph, co-crystal, tautomer, stereoisomer, isotopically labeled derivative, or prodrug thereof. The pharmaceutical compositions described herein may be useful for treating and/or preventing a disease or condition (e.g., cancer) in a subject.

In another aspect, the present invention provides methods for treating and/or preventing a disease in a subject. The methods may comprise administering to a subject in need thereof a therapeutically effective amount of a compound of Formula (I), or a pharmaceutically acceptable salt, hydrate, solvate, polymorph, co-crystal, tautomer, stereoisomer, isotopically labeled derivative, or prodrug thereof, or a pharmaceutical composition thereof. In certain embodiments, the disease is a proliferative disease such as cancer. In certain embodiments, the cancer is a hematological cancer (e.g., leukemia, lymphoma, myeloma). In certain embodiments, the cancer is leukemia (e.g., acute myeloid leukemia (AML)). In certain embodiments, the cancer is an FLT3 mutant cancer such as FLT3 mutant AML.

Compounds of the present invention can induce apoptosis of cells. Therefore, also provided herein are methods of inducing apoptosis of a cell in a subject or biological sample, the methods comprising administering to the subject or biological sample a compound of Formula (I), or a pharmaceutically acceptable salt, hydrate, solvate, polymorph, co-crystal, tautomer, stereoisomer, isotopically labeled derivative, or prodrug thereof, or a pharmaceutical composition thereof. In certain embodiments, the cell is a cancer cell. In certain embodiments, the cell is a hematopoietic cancer cell (e.g., leukemia (e.g., AML), lymphoma, myeloma).

Compounds of the present invention are effective inhibitors of alpha-enolase (Enolase 1, ENO1), which is an enzyme expressed in most tissues. Alpha-enolase overexpression is associated with several cancers and tumors including, but not limited to, hemotological cancers, gliomas, neuroendocrine tumors, neuroblastomas, prostate cancer, pancreatic cancer, cholangiocarcinoma, thyroid cancer, lung cancer, and breast cancer. In untreated cancers (e.g., hemotolocial cancers such as leukemia (e.g., AML), enolase activity is increased due to increased protein expression. Enolase provides ATP as an energy source via its role in glycolysis. Enolase also supports microtubule polymerization and re-organization, which are required for cell cycling. Without wishing to be bound by a particular theory, compounds of the present invention can inhibit alpha-enolase enzymatic activity, thereby reducing ATP for microtubule polymerization and leading to apoptotic cell death.

Provided herein are methods of modulating the enzymatic activity of (i.e., inhibiting) alpha-enolase, the methods comprising contacting the alpa-enolase with a compound of Formula (I), or a pharmaceutically acceptable salt, hydrate, solvate, polymorph, co-crystal, tautomer, stereoisomer, isotopically labeled derivative, or prodrug thereof, or a pharmaceutical composition thereof.

The present invention also provides uses of compounds of Formula (I), and pharmaceutically acceptable salts, hydrates, solvates, polymorphs, co-crystals, tautomers, stereoisomers, isotopically labeled derivatives, and prodrugs thereof, and pharmaceutical compositions thereof, in methods described herein (e.g., treatment of diseases such as cancer, inducing apoptosis of a cell, modulating the activity of alpha-enolase).

Additionally, the present invention provides uses of compounds of Formula (I), and pharmaceutically acceptable salts, hydrates, solvates, polymorphs, co-crystals, tautomers, stereoisomers, isotopically labeled derivatives, and prodrugs thereof, and pharmaceutical compositions thereof, for the manufacture of medicaments (e.g., for the treatment of diseases such as cancer).

Another aspect of the present invention relates to kits comprising a compound of Formula (I), or a salt, hydrate, solvate, polymorph, co-crystal, tautomer, stereoisomer, isotopically labeled derivative, or prodrug thereof, or pharmaceutical composition of the invention. The kits described herein may include a single dose or multiple doses of the compound or pharmaceutical composition thereof. The provided kits may be useful in a method of the invention (e.g., a method of treating and/or preventing a disease in a subject). A kit of the invention may further include instructions for using the kit (e.g., instructions for using the compound or pharmaceutical composition included in the kit).

The details of certain embodiments of the invention are set forth herein. Other features, objects, and advantages of the invention will be apparent from the Detailed Description, Figures, Examples, and Claims.

Definitions

Chemical Definitions

Definitions of specific functional groups and chemical terms are described in more detail below. The chemical elements are identified in accordance with the Periodic Table of the Elements, CAS version, *Handbook of Chemistry and Physics,* 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999*; Smith and* March, *March's Advanced Organic Chemistry,* 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis,* 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H., *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

In a formula, ∿∿ is a single bond where the stereochemistry of the moieties immediately attached thereto is not specified, - - - is absent or a single bond, and ═ or ═ is a single or double bond.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of $^{12}C$ with $^{13}C$ or $^{14}C$ are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., $-CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., $-CF_3$, Bn).

The term "haloalkyl" is a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include $—CHF_2$, $—CH_2F$, $—CF_3$, $—CH_2CF_3$, $—CF_2CF_3$, $—CF_2CF_2CF_3$, $—CC_3$, $—CFCl_2$, $—CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C═C double bond for which the stereochemistry is not specified (e.g., $—CH═CHCH_3$ or

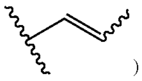

)

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("hetero$C_{2-8}$ alkenyl"). In some embodiments, a heteroalkenyl group has 2 to 7 carbon atoms, at least one double bond, and 1 or more heteroatoms within the parent chain ("hetero$C_{2-7}$ alkenyl"). In some embodiments, a heteroalkenyl group has 2 to 6 carbon atoms, at least one double bond, and 1 or more heteroatoms within the parent chain ("hetero$C_{2-6}$ alkenyl"). In some embodiments, a heteroalkenyl group has 2 to 5 carbon atoms, at least one double bond, and 1 or 2 heteroatoms within the parent chain ("hetero$C_{2-5}$ alkenyl"). In some embodiments, a heteroalkenyl group has 2 to 4 carbon atoms, at least one double bond, and 1 or 2 heteroatoms within the parent chain ("hetero$C_{2-4}$ alkenyl"). In some embodiments, a heteroalkenyl group has 2 to 3 carbon atoms, at least one double bond, and 1 heteroatom within the parent chain ("hetero$C_{2-3}$ alkenyl"). In some embodiments, a heteroalkenyl group has 2 to 6 carbon atoms, at least one double bond, and 1 or 2 heteroatoms within the parent chain ("hetero$C_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted hetero$C_{2-10}$ alkenyl. In certain embodiments, the heteroalkenyl group is a substituted hetero$C_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_2$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("hetero$C_{2-10}$ alkynyl"). In some embodiments, a heteroalkynyl group has 2 to 9 carbon atoms, at least one triple bond, and 1 or more heteroatoms within the parent chain ("hetero$C_{2-9}$ alkynyl"). In some embodiments, a heteroalkynyl group has 2 to 8 carbon atoms, at least one triple bond, and 1 or more heteroatoms within the parent chain ("hetero$C_{2-8}$ alkynyl"). In some embodiments, a heteroalkynyl group has 2 to 7 carbon atoms, at least one triple bond, and 1 or more heteroatoms within the parent chain ("hetero$C_{2-7}$ alkynyl"). In some embodiments, a heteroalkynyl group has 2 to 6 carbon atoms, at least one triple bond, and 1 or more heteroatoms within the parent chain ("hetero$C_{2-6}$ alkynyl"). In some embodiments, a heteroalkynyl group has 2 to 5 carbon atoms, at least one triple bond, and 1 or 2 heteroatoms within the parent chain ("hetero$C_{2-5}$ alkynyl"). In some embodiments, a heteroalkynyl group has 2 to 4 carbon atoms, at least one triple bond, and 1 or 2 heteroatoms within the parent chain ("hetero$C_{2-4}$ alkynyl"). In some embodiments, a heteroalkynyl group has 2 to 3 carbon atoms, at least one triple bond, and 1 heteroatom within the parent chain ("hetero$C_{2-3}$ alkynyl"). In some embodiments, a heteroalkynyl group has 2 to 6 carbon atoms, at least one triple bond, and 1 or 2 heteroatoms within the parent chain ("hetero$C_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted hetero$C_{2-10}$ alkynyl. In certain embodiments, the heteroalkynyl group is a substituted hetero$C_{2-10}$ alkynyl.

The term "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-4}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

The term "aralkyl" as generally defined herein is a subset of"alkyl" and refers to an alkyl group substituted by an aryl group, wherein the point of attachment is on the alkyl moiety (e.g., -alkyl-heterocyclyl). In certain embodiments, heterocyclylalkyl is $—C_{1-6}$ alkyl-aryl. In certain embodiments, heterocyclylalkyl is $—CH_2(CH_2)_{0-6}$-aryl. In certain embodiments, heterocyclylalkyl is $—CH_2$-aryl.

"Heteroaralkyl" is a subset of"alkyl" and refers to an alkyl group substituted by a heteroaryl group, wherein the point of attachment is on the alkyl moiety (e.g., -alkyl-heteroaryl). In certain embodiments, heteroaralkyl is $—C_{1-6}$ alkyl-heteroaryl. In certain embodiments, heteroaralkyl is $—CH_2(CH_2)_{0-6}$-heteroaryl. In certain embodiments, heteroaralkyl is $—CH_2$-heteroaryl.

"Heterocyclylalkyl" is a subset of"alkyl" and refers to an alkyl group substituted by a heterocyclyl group, wherein the point of attachment is on the alkyl moiety (e.g., -alkyl-heterocyclyl). In certain embodiments, heterocyclylalkyl is $—C_{1-6}$ alkyl-heterocyclyl. In certain embodiments, heterocyclylalkyl is $-CH_2(CH_2)_{0-6}$-heterocyclyl. In certain embodiments, heterocyclylalkyl is $-CH_2$-heterocyclyl.

The term "heteroaryl" refers to a radical of a 5-14 membered monocyclic or polycyclic (e.g., bicyclic, tricyclic) 4n+2 aromatic ring system (e.g., having 6, 10, or 14 $\pi$ electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl, and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl, and phenazinyl.

The term "unsaturated bond" refers to a double or triple bond. The term "unsaturated" or "partially unsaturated" refers to a moiety that includes at least one double or triple bond. The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3^+X^-$, —$N(OR^{cc})R^{bb}$, —SH, —$SR^{aa}$, —$SSR^{cc}$, —$C(=O)R^{aa}$, —$CO_2H$, —CHO, —$C(OR^{cc})_3$, —$CO_2R^{aa}$, —$OC(=O)R^{aa}$, —$OCO_2R^{aa}$, —$C(=O)N(R^{bb})_2$, —$OC(=O)N(R^{bb})_2$, —$NR^{bb}C(=O)R^{aa}$, —$NR^{bb}CO_2R^{aa}$, —$NR^{bb}C(=O)N(R^{bb})_2$, —$C(=NR^{bb})R^{aa}$, —$C(=NR^{bb})OR^{aa}$, —$OC(=NR^{bb})R^{aa}$, —$OC(=NR^{bb})OR^{aa}$, —$C(=NR^{bb})N(R^{bb})_2$, —$OC(=NR^{bb})N(R^{bb})_2$, —$NR^{bb}C(=NR^{bb})N(R^{bb})_2$, —$C(=O)NR^{bb}SO_2R^{aa}$, —$NR^{bb}SO_2R^{aa}$, —$SO_2N(R^{bb})_2$, —$SO_2R^{aa}$, —$SO_2OR^{aa}$, —$OSO_2R^{aa}$, —$S(=O)R^{aa}$, —$OS(=O)R^{aa}$, —$Si(R^{aa})_3$, —$OSi(R^{aa})_3$—$C(=S)N(R^{bb})_2$, —$C(=O)SR^{aa}$, —$C(=S)SR^{aa}$, —$SC(=S)SR^{aa}$, —$SC(=O)SR^{aa}$, —$OC(=O)SR^{aa}$, —$SC(=O)OR^{aa}$, —$SC(=O)R^{aa}$, —$P(=O)(R^{aa})_2$, —$P(=O)(OR^{cc})_2$, —$OP(=O)(R^{aa})_2$, —$OP(=O)(OR^{cc})_2$, —$P(=O)(N(R^{bb})_2)_2$, —$OP(=O)(N(R^{bb})_2)_2$, —$NR^{bb}P(=O)(R^{aa})_2$, —$NR^{bb}P(=)(OR^{cc})_2$, —$NR^{bb}P(=O)(N(R^{bb})_2)_2$, —$P(R^{cc})_2$, —$P(OR^{cc})_2$, —$P(R^{cc})_3^+X^-$, —$P(OR^{cc})_3^+X^-$, —$P(R^{cc})_4$, —$P(OR^{cc})_4$, —$OP(R^{cc})_2$, —$OP(R^{cc})_3^+X^-$, —$OP(OR^{cc})_2$, —$OP(OR^{cc})_3^+X^-$, —$OP(R^{cc})_4$, —$OP(OR^{cc})_4$, —$B(R^{aa})_2$, —$B(OR^{cc})_2$, —$BR_{aa}(OR^{cc})$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

or two geminal hydrogens on a carbon atom are replaced with the group =O, =S, =$NN(R^{bb})_2$, =$NNR^{bb}C(=O)R^{aa}$, =$NNR^{bb}C(=O)OR^{aa}$, =$NNR^{bb}S(=O)_2R^{aa}$, =$NR^{bb}$, or =$NOR^{cc}$; each instance of $R^{aa}$ is, independently, selected from $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

$R^{bb}$ is, independently, selected from hydrogen, —OH, —$OR^{aa}$, —$N(R^{cc})_2$, —CN, —$C(=O)R^{aa}$, —$C(=O)N(R^{cc})_2$, —$CO_2R^{aa}$, —$SO_2R^{aa}$, —$C(=NR^{cc})OR^{aa}$, —$C(=NR^{cc})N(R^{cc})_2$, —$SO_2N(R^{cc})_2$, —$SO_2R^{cc}$, —$SO_2OR^{cc}$, —$SOR^{aa}$, —$C(=S)N(R^{cc})_2$, —$C(=O)SR^{cc}$, —$C(=S)SR^{cc}$, —$P(=O)(R^{aa})_2$, —$P(=O)(OR^{cc})_2$, —$P(=O)(N(R^{cc})_2)_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R_{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —$NO_2$, —$N_3$, —$SO_2H$, —$SO_3H$, —OH, —$OR^{ee}$, —$ON(R^{ff})_2$, —$N(R^{ff})_2$, —$N(R^{ff})_3^+X^-$, —$N(OR^{ee})R^{ff}$, —SH, —$SR^{ee}$, —$SSR^{ee}$, —$C(=O)R^{ee}$, —$CO_2H$, —$CO_2R^{ee}$, —$OC(=O)R^{ee}$, —$OCO_2R^{ee}$, —$C(=O)N(R^{ff})_2$, —$OC(=O)N(R^{ff})_2$, —$NR^{ff}C(=O)R^{ee}$, —$NR^{ff}CO_2R^{ee}$, —$NR^{ff}C(=O)N(R^{ff})_2$, —$C(=NR^{ff})OR^{ee}$, —$OC(=NR^{ff})R^{ee}$, —$OC(=NR^{ff})OR^{ee}$, —$C(=NR^{ff})N(R^{ff})_2$, —$OC(=NR^{ff})N(R^{ff})_2$, —$NR^{ff}C(=NR^{ff})N(R^{ff})_2$, —$NR^{ff}SO_2R^{ee}$, —$SO_2N(R^{ff})_2$, —$SO_2R^{ee}$, —$SO_2OR^{ee}$, —$OSO_2R^{ee}$, —$S(=O)R^{ee}$, —$Si(R^{ee})_3$, —$OSi(R^{ee})_3$, —$C(=S)N(R^{ff})_2$, —$C(=O)SR^{ee}$, —$C(=S)SR^{ee}$, —$SC(=S)SR^{ee}$, —$P(=O)(OR^{ee})_2$, —$P(=O)(R^{ee})_2$, —$OP(=O)(R^{ee})_2$, —$OP(=O)(OR^{ee})_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S; wherein X is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$alkenyl, hetero$C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4 or 5 $R^{gg}$ groups; and each instance of $R^{gg}$ is, independently, halogen, —CN, —$NO_2$, —$N_3$, —$SO_2H$, —$SO_3H$, —OH, —$OC_{1-6}$ alkyl, —$ON(C_{1-6}$ alkyl$)_2$, —$N(C_{1-6}$ alkyl$)_2$, —$N(C_{1-6}$ alkyl$)_3^+X^-$, —$NH(C_{1-6}$ alkyl$)_2^+X^-$, —$NH_2(C_{1-6}$ alkyl)+$X^-$, —$NH_3^+X^-$, —$N(OC_{1-6}$ alkyl)($C_{1-6}$ alkyl), —N(OH)($C_{1-6}$ alkyl), —NH(OH), —SH, —$SC_{1-6}$ alkyl, —SS($C_{1-6}$ alkyl), —C(=O)($C_{1-6}$ alkyl), —$CO_2H$, —$CO_2$($C_{1-6}$ alkyl), —OC(=O)($C_{1-6}$ alkyl), —$OCO_2$($C_{1-6}$ alkyl), —$C(=O)NH_2$, —C(=O)N($C_{1-6}$ alkyl)$_2$, —OC(═O)NH($C_{1-6}$ alkyl), —NHC(═O)($C_{1-6}$ alkyl), —N($C_{1-6}$ alkyl)C(═O)($C_{1-6}$ alkyl), —NHCO$_2$($C_{1-6}$ alkyl), —NHC(═O)N($C_{1-6}$ alkyl)$_2$, —NHC(═O)NH($C_{1-6}$ alkyl), —NHC(═O)NH$_2$, —C(═NH)O($C_{1-6}$ alkyl), —OC(═NH)($C_{1-6}$ alkyl), —OC(═NH)O$C_{1-6}$ alkyl, —C(═NH)N($C_{1-6}$ alkyl)$_2$, —C(═NH)NH($C_{1-6}$ alkyl), —C(═NH)NH$_2$, —OC(═NH)N($C_{1-6}$ alkyl)$_2$, —OC(═NH)NH($C_{1-6}$ alkyl), —OC(═NH)NH$_2$, —NHC(═NH)N($C_{1-6}$ alkyl)$_2$, —NHC(═NH)NH$_2$, —NHSO$_2$($C_{1-6}$ alkyl), —SO$_2$N($C_{1-6}$ alkyl)$_2$, —SO$_2$NH($C_{1-6}$ alkyl), —SO$_2$NH$_2$, —SO$_2$($C_{1-6}$ alkyl), —SO$_2$O($C_{1-6}$ alkyl), —OSO$_2$($C_{1-6}$ alkyl), —SO($C_{1-6}$ alkyl), —Si($C_{1-6}$ alkyl)$_3$, —OSi($C_{1-6}$ alkyl)$_3$—C(═S)N($C_{1-6}$ alkyl)$_2$, C(═S)NH($C_{1-6}$ alkyl), C(═S)NH$_2$, —C(═O)S($C_{1-6}$ alkyl), —C(═S)S$C_{1-6}$ alkyl, —SC(═S)S$C_{1-6}$ alkyl, —P(═O)(O$C_{1-6}$ alkyl)$_2$, —P(═O)($C_{1-6}$ alkyl)$_2$, —OP(═O)($C_{1-6}$ alkyl)$_2$, —OP(═O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form ═O or ═S; wherein $X^-$ is a counterion.

In certain embodiments, carbon atom substituents include halogen, —CN, —NO$_2$, —N$_3$, —SO$_2$H, —SO$_3$H, —OH, —OR$^{aa}$, —N(R$^{bb}$)$_2$, —N(R$^{bb}$)$_3^+$X$^-$, —SH, —SR$^{aa}$, —C(═O)R$^{aa}$, —CO$_2$H, —CHO, —CO$_2$R$^{aa}$, —OC(═O)R$^{aa}$, —OCO$_2$R$^{aa}$, —C(═O)N(R$^{bb}$)$_2$, —OC(═O)N(R$^{bb}$)$_2$, —NR$^{bb}$C(═O)R$^{aa}$—NR$^{bb}$CO$_2$R$^{aa}$, —NR$^{bb}$C(═O)N(R$^{bb}$)$_2$, —NR$^{bb}$(═NR$^{bb}$)N(R$^{bb}$)$_2$, —NR$^{bb}$SO$_2$R$^{aa}$, —SO$_2$N(R$^{bb}$)$_2$, —SO$_2$R, —OSO$_2$R$^{aa}$, —S(═O)R$^{aa}$, —OS(═O)R$^{aa}$, —Si(R$^{aa}$)$_3$, —OSi(R$^{aa}$)$_3$, $C_{1-10}$ alkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group ═O, ═S, ═NN(R$^{bb}$)$_2$, ═NNR$^{bb}$C(═O)R$^{aa}$, ═NNR$^{bb}$C(═O)OR$^{aa}$, ═NNR$^{bb}$S(═O)$_2$R$^{aa}$, ═NR$^{bb}$, or ═NORaa;

wherein each instance of R$^{aa}$ is, independently, selected from $C_{1-10}$ alkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, $C_{1-10}$ alkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or a nitrogen protecting group; or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{dd}$ is, independently, selected from halogen, —CN, —NO$_2$, —N$_3$, —SO$_2$H, —SO$_3$H, —OH, —OR$^{aa}$, —N(R$^{bb}$)$_2$, —N(R$^{bb}$)$_3^+$X$^-$, —SH, —SR$^{aa}$, —C(═O)R$^{aa}$, —CO$_2$H, —CHO, —CO$_2$R$^{aa}$, —OC(═O)R$^{aa}$, —OCO$_2$R$^{aa}$, —C(═O)N(R$^{bb}$)$_2$, —OC(═O)N(R$^{bb}$)$_2$, —NR$^{bb}$C(═O)R$^{aa}$, —NR$^{bb}$CO$_2$R$^{aa}$, —NR$^{bb}$C(═O)N(R$^{bb}$)$_2$, —NR$^{bb}$(═NR$^{bb}$)N(R$^{bb}$)$_2$, —NR$^{bb}$SO$_2$R$^{aa}$, —SO$_2$N(R$^{bb}$)$_2$, —SO$_2$R$^{aa}$, —OSO$_2$R$^{aa}$, —S(═O)R$^{aa}$, —OS(═O)R$^{aa}$, —Si(R$^{aa}$)$_3$, —OSi(R$^{aa}$)$_3$, $C_{1-10}$ alkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two geminal R$^{dd}$ substituents can be joined to form ═O or ═S; wherein X$^-$ is a counterion.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(═O)SR$^{aa}$, —OC(═O)R$^{aa}$, —OCO$_2$R$^{aa}$, —OC(═O)N(R$^{bb}$)$_2$, —OC(═NR$^{bb}$)R$^{aa}$, —OC(═NR$^{bb}$)OR$^{aa}$, —OC(═NR$^{bb}$)N(R$^{bb}$)$_2$, —OS(═O)R$^{aa}$, —OSO$_2$R$^{aa}$, —OSi(R$^{aa}$)$_3$, —OP(R$^{cc}$)$_2$, —OP(R$^{cc}$)$_3^+$X$^-$, —OP(OR$^{cc}$)$_2$, —OP(OR$^{cc}$)$_3^+$X$^-$, —OP(═O)(R$^{aa}$)$_2$, —OP(═O)(OR$^{cc}$)$_2$, and —OP(═O)(N(R$^{bb}$)$_2$)$_2$, wherein X$^-$, R$^{aa}$, R$^{bb}$, and R$^{cc}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a monosubstituted amino or a disubstituted amino group. The term "substituted with nitrogen" refers to a group that is substituted with amino or substituted amino.

The term "monosubstituted amino" refers to an amino group wherein the nitrogen atom directly attached to the parent molecule is substituted with one hydrogen and one group other than hydrogen and includes groups selected from —NH(R$^{bb}$), —NHC(═O)R$^{aa}$, —NHCO$_2$R$^{aa}$, —NHC(═O)N(R$^{bb}$)$_2$, —NHC(═NR$^{bb}$)N(R$^{bb}$)$_2$, —NHSO$_2$R$^{aa}$, —NHP(═O)(OR$^{cc}$)$_2$, and —NHP(═O)(N(R$^{bb}$)$_2$)$_2$, wherein R$^{aa}$, R$^{bb}$ and R$^{cc}$ are as defined herein, and wherein R$^{bb}$ of the group —NH(R$^{bb}$) is not hydrogen.

The term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(═O)R$^{aa}$, —NR$^{bb}$CO$_2$R$^{aa}$—NR$^{bb}$C(═O)N(R$^{bb}$)$_2$, —NR$^{bb}$(═NR$^{bb}$)N(R$^{bb}$)$_2$, —NR$^{bb}$SO$_2$R, —NR$^{bb}$P(═O)(OR$^{cc}$)$_2$, and —NR$^{bb}$P(═O)(N(R$^{bb}$)$_2$)$_2$, wherein R$^{aa}$, R$^{bb}$, and R$^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3^+$X$^-$, wherein R$^{bb}$ and X are as defined herein.

The term "sulfonyl" refers to a group selected from —SO$_2$N(R$^{bb}$)$_2$, —SO$_2$R$^{aa}$, and —SO$_2$OR$^{aa}$, wherein R$^{aa}$ and R$^{bb}$ are as defined herein.

The term "sulfinyl" refers to the group —S(═O)R$^{aa}$, wherein R$^{aa}$ is as defined herein.

The term "acyl" refers to a group having the general formula —C(═O)R$^{X1}$, —C(═O)OR$^{X1}$, —C(═O)—O—C(═O)R$^{X1}$, —C(═O)SR$^{X1}$, —C(═O)N(R$^{X1}$)$_2$, —C(═S)R$^{X1}$, —C(═S)N(R$^{X1}$)$_2$, —C(═S)O(R$^{X1}$), —C(═S)S(R$^{X1}$), —C(═NR$^{X1}$)R$_{X1}$, —C(═NR$^{X1}$)OR$^{X1}$, —C(═NR$^{X1}$)SR$^{X1}$, and —C(═NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—$CO_2H$), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "carbonyl" refers a group wherein the carbon directly attached to the parent molecule is $sp^2$ hybridized, and is substituted with an oxygen, nitrogen or sulfur atom, e.g., a group selected from ketones (—C(═O)$R^{aa}$), carboxylic acids (—$CO_2H$), aldehydes (—CHO), esters (—$CO_2R^{aa}$, —C(═O)$SR^{aa}$, —C(═S)$SR^{aa}$), amides (—C(═O)N($R^{bb}$)$_2$, —C(═O)$NR^{bb}SO_2R^{aa}$, —C(═S)N($R^{bb}$)$_2$), and imines (—C(═$NR^{bb}$)$R^{aa}$, —C(═$NR^{bb}$)$OR^{aa}$), —C(═$NR^{bb}$)N($R^{bb}$)$_2$), wherein $R^{aa}$ and $R^{bb}$ are as defined herein.

The term "silyl" refers to the group —Si($R^{aa}$)$_3$, wherein $R^{aa}$ is as defined herein.

The term "oxo" refers to the group ═O, and the term "thiooxo" refers to the group ═S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —$OR^{aa}$, —N($R^{cc}$)$_2$, —CN, —C(═O)$R^{aa}$, —C(═O)N($R^{cc}$)$_2$, —$CO_2R^{aa}$, —$SO_2R^{aa}$, —C(═$NR^{bb}$)$R^{aa}$, —C(═$NR^{cc}$)$OR^{aa}$, —C(═$NR^{cc}$)N($R^{cc}$)$_2$, —$SO_2$N($R^{cc}$)$_2$, —$SO_2R^{cc}$, —$SO_2OR^{cc}$, —$SOR^{aa}$, —C(═S)N($R^{cc}$)$_2$, —C(═O)$SR^{cc}$, —C(═S)$SR^{cc}$, —P(═O)($OR^{cc}$)$_2$, —P(═O)($R^{aa}$)$_2$, —P(═O)(N($R^{cc}$)$_2$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —$OR^{aa}$, —N($R^{cc}$)$_2$, —C(═O)$R^{aa}$, —C(═O)N($R^{cc}$)$_2$, —$CO_2R^{aa}$, —$SO_2R^{aa}$, —C(═$NR^{cc}$)$R^{aa}$, —C(═$NR^{cc}$)$OR^{aa}$, —C(═$NR^{cc}$)N($R^{cc}$)$_2$, —$SO_2$N($R^{cc}$)$_2$, —$SO_2R^{cc}$, —$SO_2OR^{cc}$, —$SOR_{aa}$, —C(═S)N($R^{cc}$)$_2$, —C(═O)$SR^{cc}$, —C(═S)$SR^{cc}$, $C_{1-10}$alkyl (e.g., aralkyl, heteroaralkyl), $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 memhbered hetemrnrvl ronups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

For example, nitrogen protecting groups such as amide groups (e.g., —C(═O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenyl azophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(═O)$OR^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-l-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methyl sulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzi soxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl) methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-i-cyclopropylmethyl carbamate, 1-methyl-l-(3,5-dimethoxyphenyl)ethyl carbamate, 1-methyl-i-(p-phenylazophenyl)ethyl carbamate, 1-methyl-i-phenylethyl carbamate, 1-methyl-i-(4-pyridyl) ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), 3-trimethyl silylethanesulfonamide (SES), 9-anthracenesulfonamide, 4-(4',8'-dimethoxynaphthylmethyl)benzenesulfonamide (DNMBS), benzylsulfonamide, trifluoromethyl sulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-l, 1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethyl silyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methyl amine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxyb enzylideneamine, N-diphenylmethyl eneamine, N-[(2-pyridyl)mesityl]methyleneamine, N—(N',N'-dimethyl aminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrob enzenesulfenamide, pentachlorobenzenesulfenamide, 2-nitro-4-methoxyb enzenesulfenamide, triphenylmethylsulfenamide, and 3-nitropyridinesulfenamide (Npys). In certain embodiments, a nitrogen protecting group is benzyl (Bn), tert-butyloxycarbonyl (BOC), carbobenzyloxy (Cbz), 9-flurenylmethyloxycarbonyl (Fmoc), trifluoroacetyl, triphenylmethyl, acetyl (Ac), benzoyl (Bz), p-methoxybenzyl (PMB), 3,4-dimethoxybenzyl (DMPM), p-methoxyphenyl (PMP), 2,2,2-trichloroethyloxycarbonyl (Troc), triphenylmethyl (Tr), tosyl (Ts), brosyl (Bs), nosyl (Ns), mesyl (Ms), triflyl (Tf), or dansyl (Ds).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3^+$X$^-$, —P(OR$^{cc}$)$_2$, —P(OR$^{cc}$)$_3^+$X$^-$, —P(=O)(R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons 1999 incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethyl silyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethyl silylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris (levulinoyloxyphenyl)methyl, 4,4',4"-tris(b enzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S- dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethvlhenznote (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenyl acetate, isobutyrate, monosuccinoate, (E)-2-methyl-2-butenoate, o-(methoxyacyl)benzoate, a-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). In certain embodiments, an oxygen protecting group is silyl. In certain embodiments, an oxygen protecting group is t-butyldiphenylsilyl (TBDPS), t-butyldimethylsilyl (TBDMS), triisoproylsilyl (TIPS), triphenylsilyl (TPS), triethylsilyl (TES), trimethylsilyl (TMS), triisopropylsiloxymethyl (TOM), acetyl (Ac), benzoyl (Bz), allyl carbonate, 2,2,2-trichloroethyl carbonate (Troc), 2-trimethyl silylethyl carbonate, methoxymethyl (MOM), 1-ethoxyethyl (EE), 2-methyoxy-2-propyl (MOP), 2,2,2-trichloroethoxyethyl, 2-methoxyethoxymethyl (MEM), 2-trimethylsilylethoxymethyl (SEM), methylthiomethyl (MTM), tetrahydropyranyl (THP), tetrahydrofuranyl (THF), p-methoxyphenyl (PMP), triphenylmethyl (Tr), methoxytrityl (MMT), dimethoxytrityl (DMT), allyl, p-methoxybenzyl (PMB), t-butyl, benzyl (Bn), allyl, or pivaloyl (Piv).

In certain embodiments, the substituent present on a sulfur atom is a sulfur protecting group (also referred to as a "thiol protecting group"). Sulfur protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3{}^+X^-$, $-P(OR^{cc})_2$, $-P(OR^{cc})_3X^-$, $-P(=O)(R^{aa})_2$, $-P(=O)(OR^{cc})_2$, and $-P(=O)(N(R^{bb})_2)_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $F^-$), $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4]^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

As used herein, a "leaving group" (LG) is an art-understood term referring to a molecular fragment that departs with a pair of electrons in heterolytic bond cleavage, wherein the molecular fragment is an anion or neutral molecule. As used herein, a leaving group can be an atom or a group capable of being displaced by a nucleophile. See, for example, Smith, *March Advanced Organic Chemistry* 6th ed. (501-502). Exemplary leaving groups include, but are not limited to, halo (e.g., chloro, bromo, iodo) and activated substituted hydroxyl groups (e.g., $-OC(=O)SR^{aa}$, $-OC(=O)R^{aa}$, $-OCO_2R^{aa}$, $-OC(=O)N(R^{bb})_2$, $-OC(=NR^{bb})R^{aa}$, $-OC(=NR^{bb})OR^{aa}$, $-OC(=NR^{bb})N(R^{bb})_2$, $-OS(=O)R^{aa}$, $-OSO_2R^{aa}$, $-OP(R^{cc})_2$, $-OP(R^{cc})_3$, $-OP(=O)_2R^{aa}$, $-OP(=O)(R^{aa})_2$, $-OP(=O)(OR^{cc})_2$, $-OP(=O)_2N(R^{bb})_2$, and $-OP(=O)(NR^{bb})_2$, wherein $R^{aa}$, $R^{bb}$, and $R^{cc}$ are as defined herein).

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

A "non-hydrogen group" or "non-hydrogen substituent" refers to any group other than hydrogen.

Other Definitions

The following definitions are more general terms used throughout the present application.

As used herein, the term "salt" refers to any and all salts, and encompasses pharmaceutically acceptable salts.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences,* 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R.x $H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R•0.5 $H_2O$)), and polyhydrates (x is a number greater than 1, e.g., dihydrates (R•2 $H_2O$) and hexahydrates (R•6 $H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorph" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, e.g., Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The term "co-crystal" refers to a crystalline structure comprising at least two different components (e.g., a compound of Formula (I) and an acid), wherein each of the components is independently an atom, ion, or molecule. In certain embodiments, none of the components is a solvent. In certain embodiments, at least one of the components is a solvent. A co-crystal of a compound of Formula (I) and an acid is different from a salt formed from a compound of Formula (I) and the acid. In the salt, the compound is complexed with the acid in a way that proton transfer (e.g., a complete proton transfer) from the acid to the compound easily occurs at room temperature. In the co-crystal, however, the compound is complexed with the acid in a way that proton transfer from the acid to the compound does not easily occur at room temperature. In certain embodiments, in the co-crystal, there is no proton transfer from the acid to the compound. In certain embodiments, in the co-crystal, there is partial proton transfer from the acid to the compound. Co-crystals may be useful to improve the properties (e.g., solubility, stability, and ease of formulation) of a compound of Formula (I).

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. The term "patient" refers to a human subject in need of treatment of a disease. The subject may also be a plant. In certain embodiments, the plant is a land plant. In certain embodiments, the plant is a non-vascular land plant. In certain embodiments, the plant is a vascular land plant. In certain embodiments, the plant is a seed plant. In certain embodiments, the plant is a cultivated plant. In certain embodiments, the plant is a dicot. In certain embodiments, the plant is a monocot. In certain embodiments, the plant is a flowering plant. In some embodiments, the plant is a cereal plant, e.g., maize, corn, wheat, rice, oat, barley, rye, or millet. In some embodiments, the plant is a legume, e.g., a bean plant, e.g., soybean plant. In some embodiments, the plant is a tree or shrub.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The term "target tissue" refers to any biological tissue of a subject (including a group of cells, a body part, or an organ) or a part thereof, including blood and/or lymph vessels, which is the object to which a compound, particle, and/or composition of the invention is delivered. A target tissue may be an abnormal or unhealthy tissue, which may need to be treated. A target tissue may also be a normal or healthy tissue that is under a higher than normal risk of becoming abnormal or unhealthy, which may need to be prevented. In certain embodiments, the target tissue is the liver. In certain embodiments, the target tissue is the lung. A "non-target tissue" is any biological tissue of a subject (including a group of cells, a body part, or an organ) or a part thereof, including blood and/or lymph vessels, which is not a target tissue.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent. In certain embodiments, a therapeutically effective amount is an amount sufficient for treating a proliferative disease. In certain embodiments, a therapeutically effective amount is an amount sufficient for treating cancer. In certain embodiments, a therapeutically effective amount is an amount sufficient for treating leukemia. In certain embodiments, a therapeutically effective amount is an amount sufficient for treating acute myeloid leukemia.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent. In certain embodiments, a prophylactically effective amount is an amount sufficient for preventing any disease or condition described herein.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "cancer" refers to a class of diseases characterized by the development of abnormal cells that proliferate uncontrollably and have the ability to infiltrate and destroy normal body tissues. See, e.g., *Stedman's Medical Dictionary,* 25th ed.; Hensyl ed.; Williams & Wilkins: Philadelphia, 1990. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., acute monocytic leukemia, acute myelomonocytic leukemia, acute promyelocytic leukemia), chronic myelocytic leukemia (CML), and chronic lymphocytic leukemia (CLL)); myelodysplastic syndromes; myeloproliferative neoplasms; myelofibrosis; lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenstrom's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

A "hematological disease" includes a disease which affects a hematopoietic cell or tissue. Hematological diseases include diseases associated with aberrant hematological content and/or function. Hematological diseases include hematological cancers. Examples of hematological diseases include diseases resulting from bone marrow irradiation or chemotherapy treatments for cancer, diseases such as pernicious anemia, hemorrhagic anemia, hemolytic anemia, aplastic anemia, sickle cell anemia, sideroblastic anemia, myelodysplastic syndromes, myeloproliferative neoplasms, myelofibrosis (i.e., primary and secondary), anemia associated with chronic infections such as malaria, trypanosomiasis, HTV, hepatitis virus or other viruses, myelophthisic anemias caused by marrow deficiencies, renal failure resulting from anemia, anemia, polycythemia, infectious mononucleosis (EVI), acute non-lymphocytic leukemia (ANLL), acute myeloid leukemia (AML), acute promyelocytic leukemia (APL), acute myelomonocytic leukemia (AMMoL), polycythemia vera, lymphoma, acute lymphocytic leukemia (ALL), chronic lymphocytic leukemia, Wilm's tumor, Ewing's sarcoma, retinoblastoma, hemophilia, disorders associated with an increased risk of thrombosis, herpes, thalassemia, antibody-mediated disorders such as transfusion reactions and erythroblastosis, mechanical trauma to red blood cells such as micro-angiopathic hemolytic anemias, thrombotic thrombocytopenic purpura and disseminated intravascular coagulation, infections by parasites such as *Plasmodium*, chemical injuries from, e.g., lead poisoning, and hypersplenism.

"Antiproliferative agents" include "anti-cancer agents", and encompass biotherapeutic anti-cancer agents as well as chemotherapeutic agents. Exemplary biotherapeutic antiproliferative agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune checkpoint inhibitors, chemokine receptor inhibitors, immune cell growth factors (e.g., GM-CSF) and antibodies (e.g. HERCEPTIN (trastuzumab), T-DM1, AVASTIN (bevacizumab), ERBITUX (cetuximab), VECTIBIX (panitumumab), RITUXAN (rituximab), BEXXAR (tositumomab)). Exemplary chemotherapeutic agents (i.e., chemotherapeutic anti-proliferative agents) include, but are not limited to, anti-estrogens (e.g. tamoxifen, raloxifene, and megestrol), LHRH agonists (e.g. goscrclin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), *vinca* alkaloids (e.g. vincristine, vinblastine, vindesine, and vinorelbine), taxoids (e.g. paclitaxel or a paclitaxel equivalent such as nanoparticle albumin-bound paclitaxel (ABRAXANE), docosahexaenoic acid bound-n litxel (DHA-na clitixel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonuclotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), $Ca^{2+}$ ATPase inhibitors (e.g. thapsigargin), imatinib, thalidomide, lenalidomide, tyrosine kinase inhibitors (e.g., axitinib (AGO13736), bosutinib (SKI-606), cediranib (RECENTIN$^T$, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temirnlimii (CC-779) everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

As used herein, the term "apoptosis" refers to a regulated network of biochemical events which lead to a selective form of cell suicide and is characterized by readily observable morphological and biochemical phenomena. Cells undergoing apoptosis show characteristic morphological and biochemical features. These features include chromatin aggregation or condensation, DNA fragmentation, nuclear and cytoplasmic condensation, partition of cytoplasm and nucleus into membrane bound vesicles (apoptotic bodies) which contain ribosomes, morphologically intact mitochondria and nuclear material. Cytochrome C release from mitochondria is seen as an indication of mitochondrial outer membrane permeabilization accompanying apoptosis.

As used herein, "inhibition", "inhibiting", "inhibit" and "inhibitor", and the like, refer to the ability of a compound to reduce, slow, halt, or prevent the activity of a biological process (e.g., a biological process in a cell). In certain embodiments, such inhibition is of about 1% to 99.9%. In certain embodiments, the inhibition is about 1% to about 95%. In certain embodiments, the inhibition is about 5% to 90%. In certain embodiments, the inhibition is about 10% to 85%. In certain embodiments, the inhibition is about 15% to 80%. In certain embodiments, the inhibition is about 20% to 75%. In certain embodiments, the inhibition is about 25% to 70%. In certain embodiments, the inhibition is about 30% to 65%. In certain embodiments, the inhibition is about 35% to 60%. In certain embodiments, the inhibition is about 40% to 55%. In certain embodiments, the inhibition is about 45% to 50%. In certain embodiments, the inhibition is about 5%, 10%, 15%, 20%, 25%, 30%, 35%, 40%, 45%, 50%, 55%, 60%, 65%, 70%, 75%, 80%, 85%, 90%, 95%, or 99.9%.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF CERTAIN EMBODIMENTS

Figure 1:
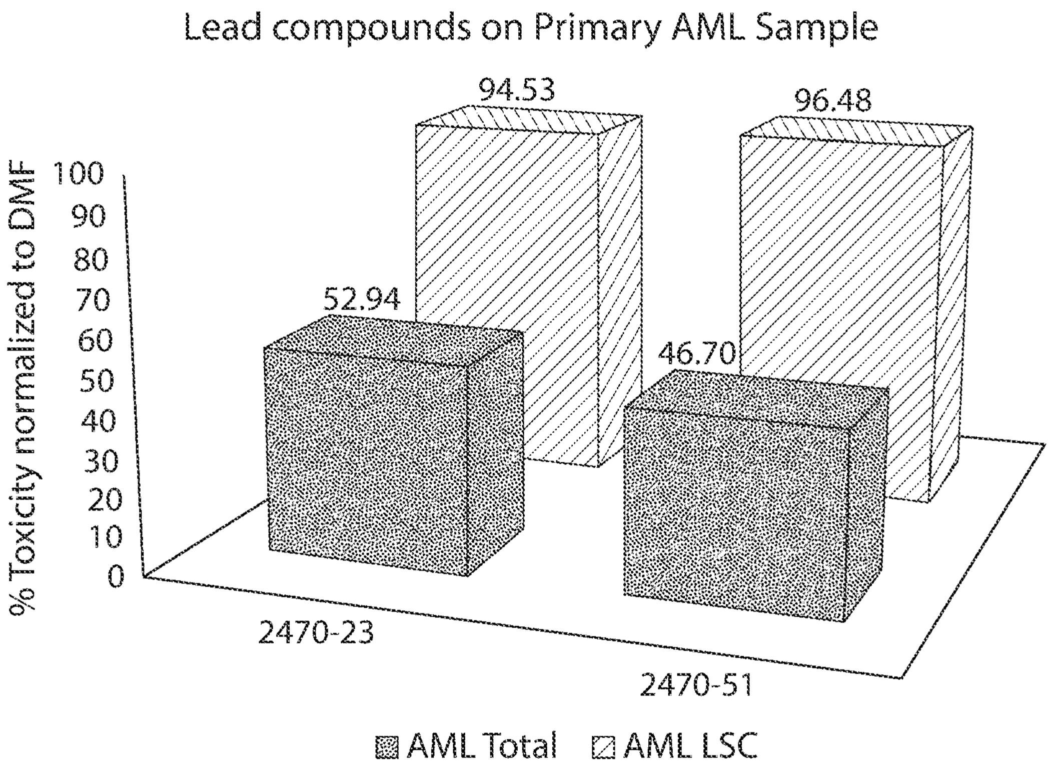
FIG. 1. Comparing average AML-LSC toxicity vs. AML total toxicity. Fresh human primary leukemia bone marrow mononuclear cells were treated with single doses of compounds 2470-23 and 2470-51 at a single time point and the killing of the leukemia stem cell (LSC) population (defined as CD34+CD38-CD123+) was quantified versus the total AML cell population. This demonstrates that both compounds selectively kills the AML LSC fraction, which is responsible for cancer refractoriness and relapse.

Effective treatment of acute myeloid leukemia (AML) and related diseases constitute an unmet medical need, and therefore the discovery and development of new anti-proliferative agents is critically important. Human AML cells functionally integrate within blood vessels, occasionally fusing with endothelial cells (ECs), and consequently can become more resistant to existing antineoplastic agents. The present invention relates in part to new therapeutic compounds with anti-neoplastic activity. Provided herein are polyamine sulfonamides such as compounds of Formula (I), and pharmaceutically acceptable salts, hydrates, solvates, polymorphs, co-crystals, tautomers, stereoisomers, isotopically labeled derivatives, and prodrugs thereof, which may be used in the treatment and/or prevention of diseases such as cancer and other proliferative diseases. Also provided herein are pharmaceutical compositions and kits comprising the inventive compounds. Furthermore, the present invention provides methods of treating diseases (e.g., hematological cancers such as AML) using compounds of Formula (I), or pharmaceutically acceptable salts, hydrates, solvates, polymorphs, co-crystals, tautomers, stereoisomers, isotopically labeled derivatives, or prodrugs thereof, or pharmaceutical compositions thereof. Also provided herein are methods of inhibiting the enzymatic activity of alpha-enolase proteins and inducing apoptosis of cells using compounds of Formula (I), or pharmaceutically acceptable salts, hydrates, solvates, polymorphs, co-crystals, tautomers, stereoisomers, isotopically labeled derivatives, or prodrugs thereof, or pharmaceutical compositions thereof. The following describes in detail several embodiments of the invention.

Compounds

One aspect of the present invention relates to polyamine sulfonamides, which may be useful in the treatment and/or prevention of diseases or conditions. In certain embodiments, the polyamine sulfonamides of the present invention are of Formula (I). Provided herein are compounds of Formula (I):

(I)

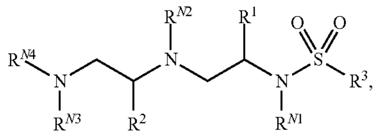

and pharmaceutically acceptable salts, hydrates, solvates, polymorphs, co-crystals, tautomers, stereoisomers, isotopically labeled derivatives, and prodrugs thereof, wherein:

$R^1$ is hydrogen, optionally substituted $C_{1-6}$ alkyl, optionally substituted carbocyclyl, optionally substituted heterocyclyl, optionally substituted heterocyclylalkyl, or optionally substituted heteroaralkyl;

$R^2$ is hydrogen, optionally substituted $C_{1-6}$ alkyl, optionally substituted carbocyclyl, optionally substituted heterocyclyl, optionally substituted heterocyclylalkyl, or optionally substituted heteroaralkyl;

$R^3$ is optionally substituted alkyl, optionally substituted aryl, optionally substituted heteroaryl, optionally substituted carbocyclyl, or optionally substituted heterocyclyl; and $R^{N1}$, $R^{N2}$, $R^{N3}$, and $R^{N4}$ are each independently hydrogen, optionally substituted alkyl, optionally substituted aryl, optionally substituted acyl, or a nitrogen protecting group; or optionally $R^{N3}$ and $R^{N4}$ are joined together with the intervening atoms to form optionally substituted heterocyclyl or optionally substituted heteroaryl;

optionally wherein $R^2$ and either $R^{N3}$ or $R^{N4}$ are joined together with the intervening atoms to form optionally substituted heterocyclyl; or optionally wherein $R^1$ and $R^{N2}$ are joined together with the intervening atoms to form optionally substituted heterocyclyl; or optionally wherein $R^3$ and $R^{N1}$ are joined together with the intervening atoms to form optionally substituted heterocyclyl;

provided that at least one of $R^1$ and $R^2$ is a non-hydrogen group; and provided that neither $R^1$ or $R^2$ is benzyl.

Also provided herein are compounds of Formula (I):

(I)

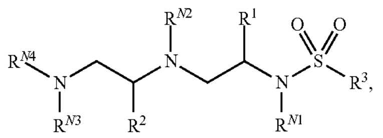

and pharmaceutically acceptable salts, hydrates, solvates, polymorphs, co-crystals, tautomers, stereoisomers, isotopically labeled derivatives, and prodrugs thereof, wherein:

$R^1$ is hydrogen, optionally substituted $C_{1-6}$ alkyl, optionally substituted carbocyclyl, optionally substituted heterocyclyl, optionally substituted heterocyclylalkyl, or optionally substituted heteroaralkyl;

$R^2$ is hydrogen, optionally substituted $C_{1-6}$ alkyl, optionally substituted carbocyclyl, optionally substituted heterocyclyl, optionally substituted heterocyclylalkyl, or optionally substituted heteroaralkyl;

$R^3$ is optionally substituted alkyl, optionally substituted aryl, optionally substituted heteroaryl, optionally substituted carbocyclyl, or optionally substituted heterocyclyl; and $R^{N1}$, $R^{N2}$, $R^{N3}$, and $R^{N4}$ are each independently hydrogen, optionally substituted alkyl, optionally substituted aryl, optionally substituted acyl, or a nitrogen protecting group; or optionally $R^{N3}$ and $R^{N4}$ are joined together with the intervening atoms to form optionally substituted heterocyclyl or optionally substituted heteroaryl;

provided that at least one of $R^1$ and $R^2$ is a non-hydrogen group; and provided that neither $R^1$ or $R^2$ is benzyl.

As described herein, at least one of $R^1$ and $R^2$ is not hydrogen (i.e., either or both $R^1$ are $R^2$ are a non-hydrogen substituent). In certain embodiments, $R^1$ is hydrogen, and $R^2$ is a non-hydrogen substituent. In certain embodiments, $R^2$ is hydrogen, and $R^1$ is a non-hydrogen substituent. In certain embodiments, both $R^1$ and $R^2$ are not hydrogen (i.e., both $R^1$ and $R^2$ are non-hydrogen substituents).

As described herein, both $R^1$ and $R^2$ are not benzyl (i.e., neither $R^1$ nor $R^2$ is benzyl). As generally defined herein, benzyl is $-CH_2Ph$.

In certain embodiments of Formula (I), $R^2$ and either $R^{N3}$ or $R^{N4}$ are joined together with the intervening atoms to form optionally substituted heterocyclyl. In certain embodiments, $R^1$ and $R^{N2}$ are joined together with the intervening atoms to form optionally substituted heterocyclyl. In other embodiments, $R^3$ and $R^{N1}$ are joined together with the intervening atoms to form optionally substituted heterocyclyl. In certain embodiments, a compound of Formula (I) is of one of the following formulae:

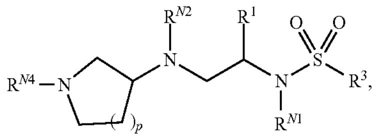

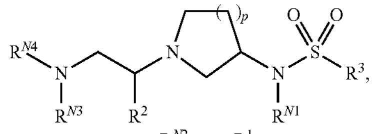

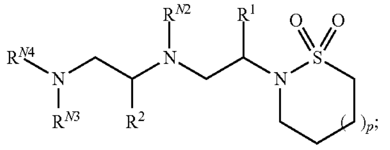

or a pharmaceutically acceptable salt, hydrate, solvate, polymorph, co-crystal, tautomer, stereoisomer, isotopically labeled derivative, or prodrug thereof, wherein:

p is 0, 1, or 2.

In certain embodiments, a compound of Formula (I) is of one of the following formulae:

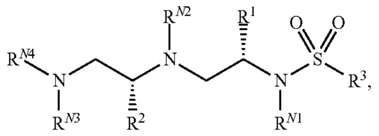

-continued

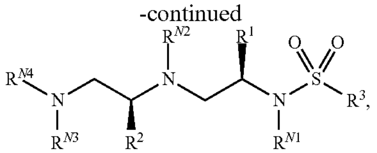

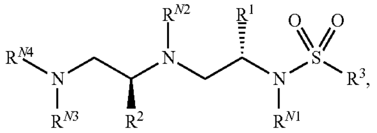

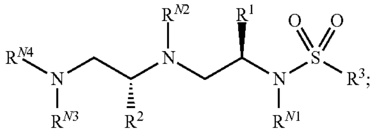

or a pharmaceutically acceptable salt, hydrate, solvate, polymorph, co-crystal, tautomer, stereoisomer, isotopically labeled derivative, or prodrug thereof.

Formula (I) includes substituents $R^3$, $R^1$, $R^2$, $R^{N1}$, $R^{N2}$, $R^{N3}$, and $R^{N4}$. In certain embodiments, $R^3$ is optionally substituted alkyl, optionally substituted aryl, optionally substituted heteroaryl, optionally substituted carbocyclyl, or optionally substituted heterocyclyl; $R^1$ is optionally substituted $C_{1-6}$ alkyl; $R^2$ is optionally substituted $C_{1-6}$ alkyl; and $R^{N1}$, $R^{N2}$, $R^{N3}$, and $R^{N4}$ are H. In certain embodiments, $R^3$ is optionally substituted alkyl; $R^1$ is optionally substituted $C_{1-6}$alkyl; $R^2$ is optionally substituted $C_{1-6}$ alkyl; and $R^{N1}$, $R^{N2}$, $R^{N3}$, and $R^{N4}$ are H. In certain embodiments, $R^3$ is optionally substituted heteroaryl; $R^1$ is optionally substituted $C_{1-6}$ alkyl; $R^2$ is optionally substituted $C_{1-6}$ alkyl; and $R^{N1}$, $R^{N2}$, $R^{N3}$, and $R^{N4}$ are H. In certain embodiments, $R^3$ is optionally substituted carbocyclyl; $R^1$ is optionally substituted $C_{1-6}$ alkyl; $R^2$ is optionally substituted $C_{1-6}$ alkyl; and $R^{N1}$, $R^{N2}$, $R^{N3}$, and $R^{N4}$ are H. In certain embodiments, $R^3$ is optionally substituted heterocyclyl; $R^1$ is optionally substituted $C_{1-6}$ alkyl; $R^2$ is optionally substituted $C_{1-6}$ alkyl; and $R^{N1}$, $R^{N2}$, $R^{N3}$, and $R^{N4}$ are H. In certain embodiments, $R^3$ is optionally substituted heteroaryl; $R^1$ is optionally substituted $C_{1-6}$ alkyl; $R^2$ is optionally substituted $C_{1-6}$ alkyl; and $R^{N1}$, $R^{N2}$, $R^{N3}$, and $R^{N4}$ are H. In certain embodiments, $R^3$ is optionally substituted aryl; $R^1$ is optionally substituted $C_{1-6}$ alkyl; $R^2$ is optionally substituted $C_{1-6}$ alkyl; and $R^{N1}$, $R^{N2}$, $R^{N3}$, and $R^{N4}$ are H. In certain embodiments, $R^3$ is optionally substituted phenyl; $R^1$ is optionally substituted $C_{1-6}$ alkyl; $R^2$ is optionally substituted $C_{1-6}$ alkyl; and $R^{N1}$, $R^{N2}$, $R^{N3}$, and $R^{N4}$ are H. In certain embodiments, $R^3$ is optionally substituted naphthyl; $R^1$ is optionally substituted $C_{1-6}$ alkyl; $R^2$ is optionally substituted $C_{1-6}$ alkyl; and $R^{N1}$, $R^{N2}$, $R^{N3}$, and $R^{N4}$ are H.

In certain embodiments, the compound of Formula (I) is of the following formula:

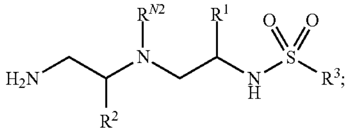

or a pharmaceutically acceptable salt, hydrate, solvate, polymorph, co-crystal, tautomer, stereoisomer, isotopically labeled derivative, or prodrug thereof.

In certain embodiments, the compound of Formula (I) is of one of the following formulae:

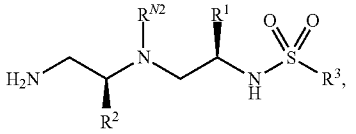

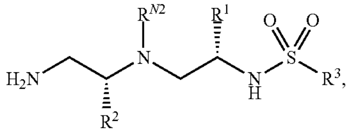

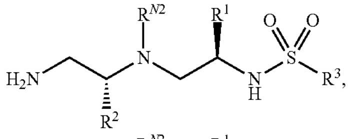

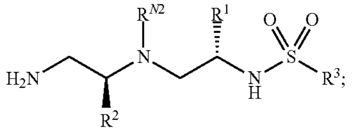

or a pharmaceutically acceptable salt, hydrate, solvate, polymorph, co-crystal, tautomer, stereoisomer, isotopically labeled derivative, or prodrug thereof.

In certain embodiments, the compound of Formula (I) is of the following formula:

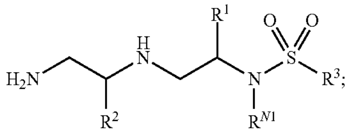

or a pharmaceutically acceptable salt, hydrate, solvate, polymorph, co-crystal, tautomer, stereoisomer, isotopically labeled derivative, or prodrug thereof.

In certain embodiments, the compound of Formula (I) is of one of the following formulae:

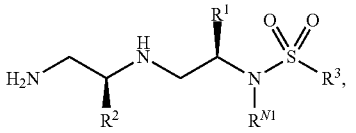

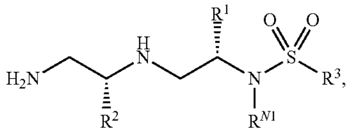

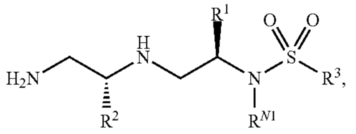

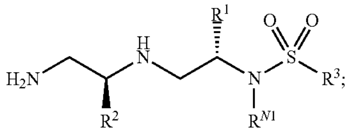

or a pharmaceutically acceptable salt, hydrate, solvate, polymorph, co-crystal, tautomer, stereoisomer, isotopically labeled derivative, or prodrug thereof.

In certain embodiments, the compound of Formula (I) is of the following formula:

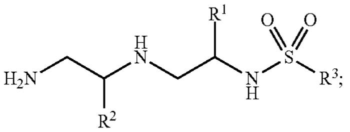

or a pharmaceutically acceptable salt, hydrate, solvate, polymorph, co-crystal, tautomer, stereoisomer, isotopically labeled derivative, or prodrug thereof.

In certain embodiments, the compound of Formula (I) is of one of the following formulae:

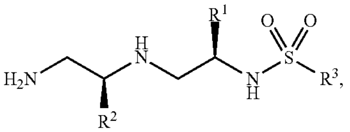

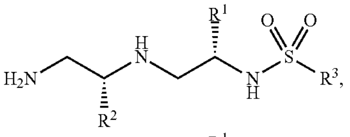

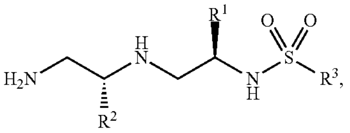

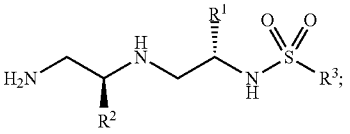

or a pharmaceutically acceptable salt, hydrate, solvate, polymorph, co-crystal, tautomer, stereoisomer, isotopically labeled derivative, or prodrug thereof.

In certain embodiments, the compound of Formula (I) is of the following formula:

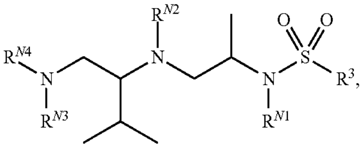

or a pharmaceutically acceptable salt, hydrate, solvate, polymorph, co-crystal, tautomer, stereoisomer, isotopically labeled derivative, or prodrug thereof.

In certain embodiments, a compound of Formula (I) is of one of the following formulae:

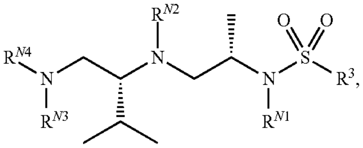

-continued

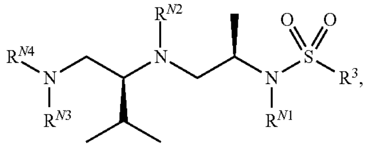

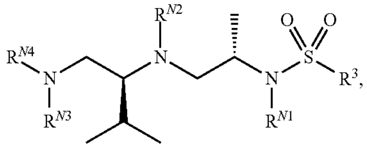

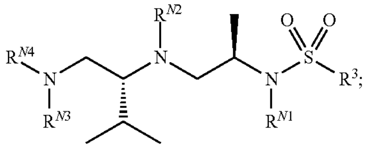

or a pharmaceutically acceptable salt, hydrate, solvate, polymorph, co-crystal, tautomer, stereoisomer, isotopically labeled derivative, or prodrug thereof.

In certain embodiments, the compound of Formula (I) is of the following formula:

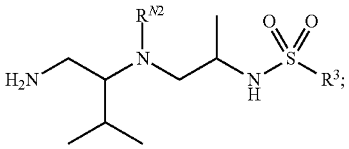

or a pharmaceutically acceptable salt, hydrate, solvate, polymorph, co-crystal, tautomer, stereoisomer, isotopically labeled derivative, or prodrug thereof.

In certain embodiments, the compound of Formula (I) is of one of the following formulae:

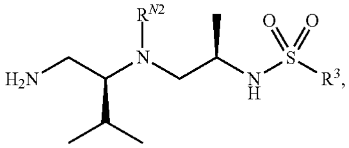

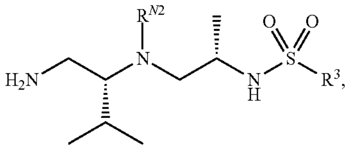

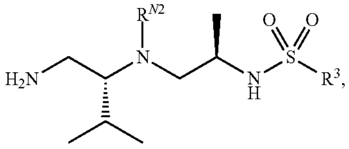

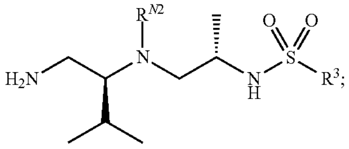

or a pharmaceutically acceptable salt, hydrate, solvate, polymorph, co-crystal, tautomer, stereoisomer, isotopically labeled derivative, or prodrug thereof.

In certain embodiments, the compound of Formula (I) is of the following formula:

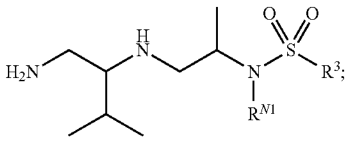

or a pharmaceutically acceptable salt, hydrate, solvate, polymorph, co-crystal, tautomer, stereoisomer, isotopically labeled derivative, or prodrug thereof.

In certain embodiments, the compound of Formula (I) is of one of the following formulae:

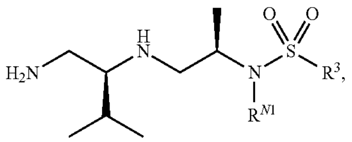

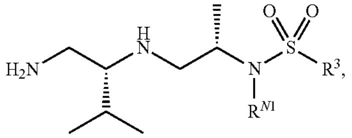

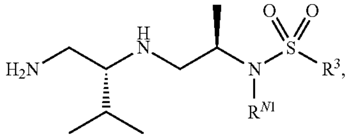

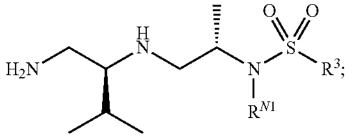

or a pharmaceutically acceptable salt, hydrate, solvate, polymorph, co-crystal, tautomer, stereoisomer, isotopically labeled derivative, or prodrug thereof.

In certain embodiments, the compound of Formula (I) is of the following formula:

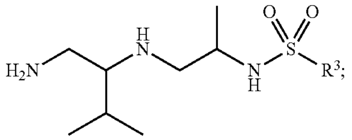

or a pharmaceutically acceptable salt, hydrate, solvate, polymorph, co-crystal, tautomer, stereoisomer, isotopically labeled derivative, or prodrug thereof.

In certain embodiments, the compound of Formula (I) is of one of the following formulae:

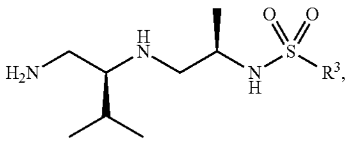

-continued

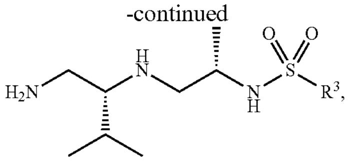

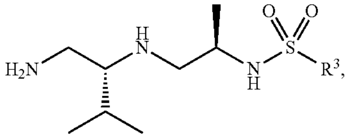

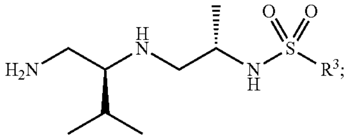

or a pharmaceutically acceptable salt, hydrate, solvate, polymorph, co-crystal, tautomer, stereoisomer, isotopically labeled derivative, or prodrug thereof.

In certain embodiments, the compound of Formula (I) is of the following formula:

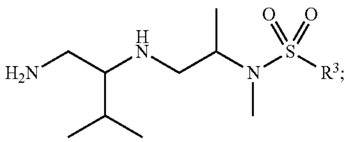

or a pharmaceutically acceptable salt, hydrate, solvate, polymorph, co-crystal, tautomer, stereoisomer, isotopically labeled derivative, or prodrug thereof.

In certain embodiments, the compound of Formula (I) is of one of the following formulae:

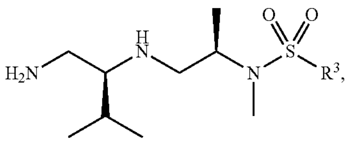

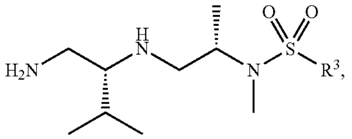

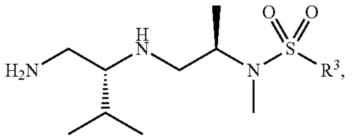

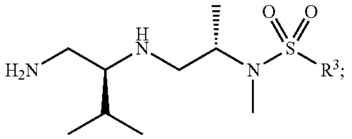

or a pharmaceutically acceptable salt, hydrate, solvate, polymorph, co-crystal, tautomer, stereoisomer, isotopically labeled derivative, or prodrug thereof.

In certain embodiments, $R^3$ and $R^{N1}$ are joined together with the intervening atoms to form optionally substituted heterocyclyl; and a compound of Formula (I) is of the following formula:

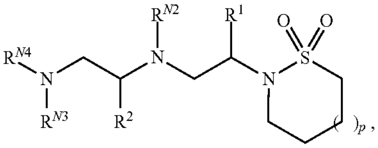

or a pharmaceutically acceptable salt, hydrate, solvate, polymorph, co-crystal, tautomer, stereoisomer, isotopically labeled derivative, or prodrug thereof.

In certain embodiments, the compound of Formula (I) is of one of the following formulae:

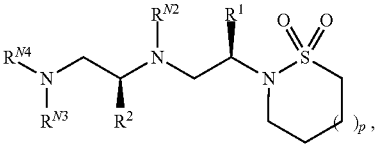

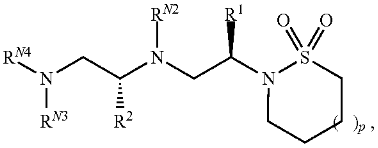

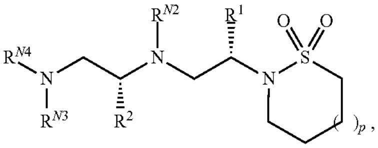

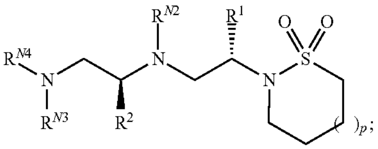

or a pharmaceutically acceptable salt, hydrate, solvate, polymorph, co-crystal, tautomer, stereoisomer, isotopically labeled derivative, or prodrug thereof.

In certain embodiments, a compound of Formula (I) is of the following formula:

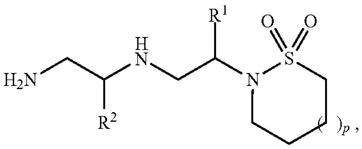

or a pharmaceutically acceptable salt, hydrate, solvate, polymorph, co-crystal, tautomer, stereoisomer, isotopically labeled derivative, or prodrug thereof.

In certain embodiments, the compound of Formula (I) is of one of the following formulae:

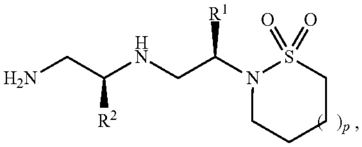

-continued

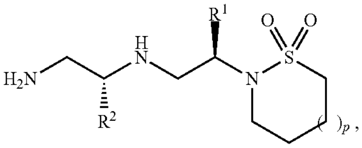

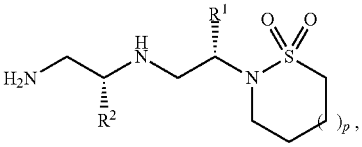

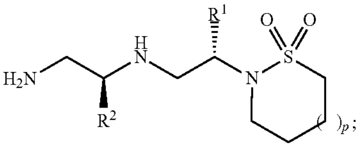

or a pharmaceutically acceptable salt, hydrate, solvate, polymorph, co-crystal, tautomer, stereoisomer, isotopically labeled derivative, or prodrug thereof.

In certain embodiments, a compound of Formula (I) is of the following formula:

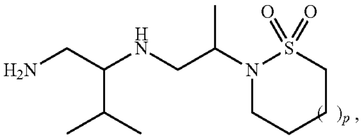

or a pharmaceutically acceptable salt, hydrate, solvate, polymorph, co-crystal, tautomer, stereoisomer, isotopically labeled derivative, or prodrug thereof.

In certain embodiments, the compound of Formula (I) is of one of the following formulae:

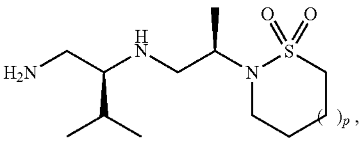

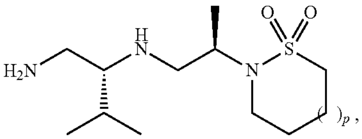

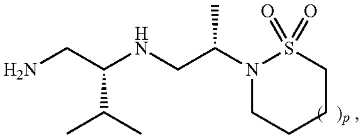

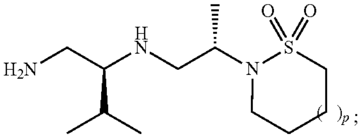

or a pharmaceutically acceptable salt, hydrate, solvate, polymorph, co-crystal, tautomer, stereoisomer, isotopically labeled derivative, or prodrug thereof.

In certain embodiments, a compound of Formula (I) is of the following formula:

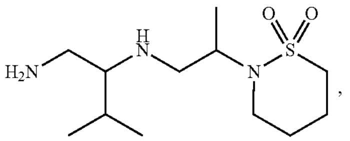 [SMILES: CC(C)C(CN)NCC(C)N1CCCCS1(=O)=O]

or a pharmaceutically acceptable salt, hydrate, solvate, polymorph, co-crystal, tautomer, stereoisomer, isotopically labeled derivative, or prodrug thereof.

In certain embodiments, the compound of Formula (I) is of one of the following formulae:

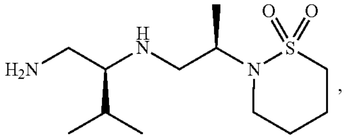

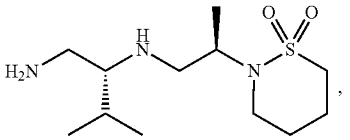

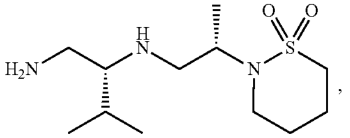

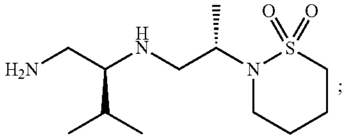

or a pharmaceutically acceptable salt, hydrate, solvate, polymorph, co-crystal, tautomer, stereoisomer, isotopically labeled derivative, or prodrug thereof.

In certain embodiments, $R^2$ and $R^{N3}$ are joined together with the intervening atoms to form optionally substituted heterocyclyl; and the compound of Formula (I) is of the formula:

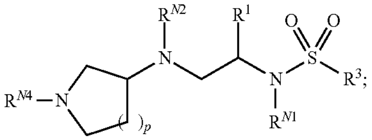

or a pharmaceutically acceptable salt, hydrate, solvate, polymorph, co-crystal, tautomer, stereoisomer, isotopically labeled derivative, or prodrug thereof.

In certain embodiments, the compound of Formula (I) is of one of the following formulae:

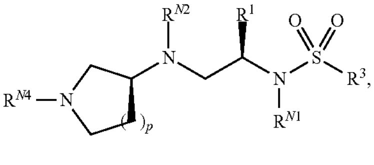

-continued

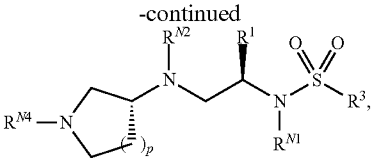

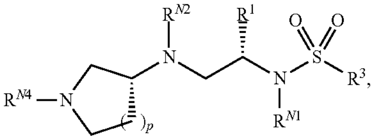

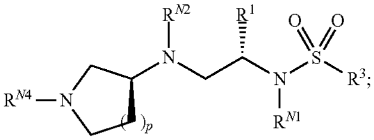

or a pharmaceutically acceptable salt, hydrate, solvate, polymorph, co-crystal, tautomer, stereoisomer, isotopically labeled derivative, or prodrug thereof.

In certain embodiments, the compound of Formula (I) is of the formula:

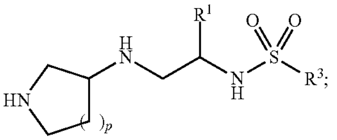

or a pharmaceutically acceptable salt, hydrate, solvate, polymorph, co-crystal, tautomer, stereoisomer, isotopically labeled derivative, or prodrug thereof.

In certain embodiments, the compound of Formula (I) is of one of the following formulae:

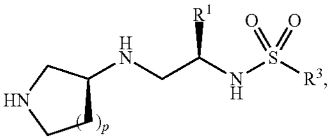

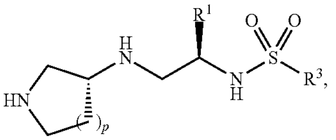

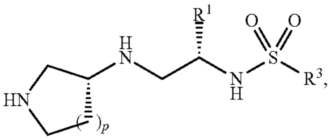

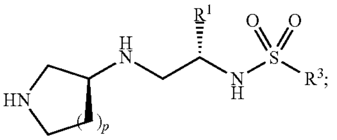

or a pharmaceutically acceptable salt, hydrate, solvate, polymorph, co-crystal, tautomer, stereoisomer, isotopically labeled derivative, or prodrug thereof.

In certain embodiments, $R^1$ and $R^{N2}$ are joined together to form optionally substituted heterocyclyl; and the compound of Formula (I) is of the following formula:

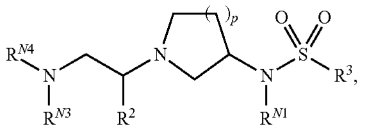

or a pharmaceutically acceptable salt, hydrate, solvate, polymorph, co-crystal, tautomer, stereoisomer isotopically labeled derivative, or prodrug thereof.

In certain embodiments, the compound of Formula (I) is of one of the following formula:

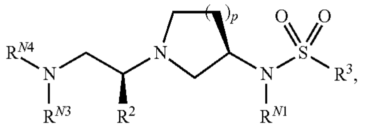

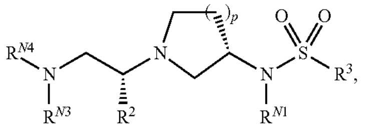

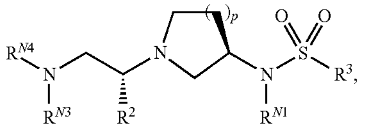

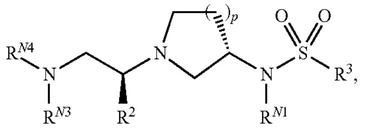

or a pharmaceutically acceptable salt, hydrate, solvate, polymorph, co-crystal, tautomer, stereoisomer, isotopically labeled derivative, or prodrug thereof.

In certain embodiments, $R^1$ and $R^{N2}$ are joined together to form optionally substituted heterocyclyl; and the compound of Formula (I) is of the following formula:

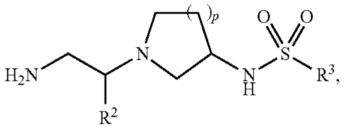

or a pharmaceutically acceptable salt, hydrate, solvate, polymorph, co-crystal, tautomer, stereoisomer, isotopically labeled derivative, or prodrug thereof.

In certain embodiments, the compound of Formula (I) is of one of the following formula:

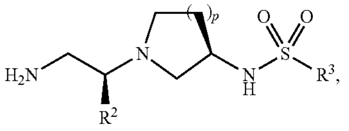

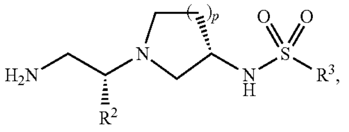

-continued

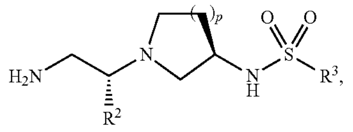

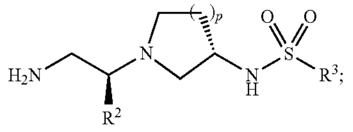

or a pharmaceutically acceptable salt, hydrate, solvate, polymorph, co-crystal, tautomer, stereoisomer, isotopically labeled derivative, or prodrug thereof.

In certain embodiments, $R^3$ is optionally substituted phenyl; and the compound of Formula (I) is of Formula (II):

(II)

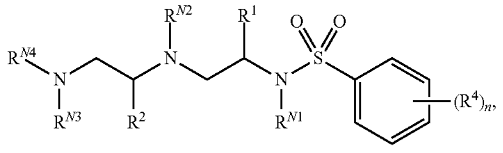

or a pharmaceutically acceptable salt, hydrate, solvate, polymorph, co-crystal, tautomer, stereoisomer, isotopically labeled derivative, or prodrug thereof, wherein:

$R^1$ is hydrogen, optionally substituted $C_{1-6}$ alkyl, optionally substituted carbocyclyl, optionally substituted heterocyclyl, optionally substituted heterocyclylalkyl, or optionally substituted heteroaralkyl;

$R^2$ is hydrogen, optionally substituted $C_{1-6}$ alkyl, optionally substituted carbocyclyl, optionally substituted heterocyclyl, optionally substituted heterocyclylalkyl, or optionally substituted heteroaralkyl;

$R^{N1}$, $R^{N2}$, $R^{N3}$, and $R^{N4}$ are each independently hydrogen, optionally substituted alkyl, optionally substituted aryl, optionally substituted acyl, or a nitrogen protecting group; or optionally $R^{N3}$ and $R^{N4}$ are joined together with the intervening atoms to form optionally substituted heterocyclyl or optionally substituted heteroaryl;

each instance of $R^4$ is independently hydrogen, halogen, —CN, —$NO_2$, —$N_3$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^{4a}$, —$N(R^{4b})_2$, or —$SR^{4c}$;

each instance of $R^{4a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or an oxygen protecting group;

each instance of $R^{4b}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group; or optionally two $R^{3b}$ are joined together with the intervening atoms to form optionally substituted heterocyclyl or optionally substituted heteroaryl;

each instance of $R^{4c}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a sulfur protecting group; and n is 0, 1, 2, 3, 4, or 5; optionally wherein $R^2$ and either $R^{N3}$ or $R^{N4}$ are joined together with the intervening atoms to form optionally substituted heterocyclyl; or optionally wherein $R^1$ and $R^{N2}$ are joined together with the intervening atoms to form optionally substituted heterocyclyl; or optionally wherein $R^3$ and $R^{N1}$ are joined together with the intervening atoms to form optionally substituted heterocyclyl;

provided that at least one of $R^1$ and $R^2$ is a non-hydrogen group; and provided that neither $R^1$ or $R^2$ is benzyl.

In certain embodiments, a compound of Formula (I) is of Formula (II):

(II)

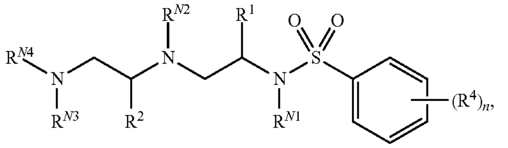

or a pharmaceutically acceptable salt, hydrate, solvate, polymorph, co-crystal, tautomer, stereoisomer, isotopically labeled derivative, or prodrug thereof, wherein:

$R^1$ is hydrogen, optionally substituted $C_{1-6}$ alkyl, optionally substituted carbocyclyl, optionally substituted heterocyclyl, optionally substituted heterocyclylalkyl, or optionally substituted heteroaralkyl;

$R^2$ is hydrogen, optionally substituted $C_{1-6}$ alkyl, optionally substituted carbocyclyl, optionally substituted heterocyclyl, optionally substituted heterocyclylalkyl, or optionally substituted heteroaralkyl;

$R^{N1}$, $R^{N2}$, $R^{N3}$, and $R^{N4}$ are each independently hydrogen, optionally substituted alkyl, optionally substituted aryl, optionally substituted acyl, or a nitrogen protecting group; or optionally $R^{N3}$ and $R^{N4}$ are joined together with the intervening atoms to form optionally substituted heterocyclyl or optionally substituted heteroaryl;

each instance of $R^4$ is independently hydrogen, halogen, —CN, —$NO_2$, —$N_3$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^{4a}$, —$N(R^{4b})_2$, or —$SR^{4c}$;

each instance of $R^{4a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or an oxygen protecting group;

each instance of $R^{4b}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group; or optionally two $R^{3b}$ are joined together with the intervening atoms to form optionally substituted heterocyclyl or optionally substituted heteroaryl;

each instance of $R^{4c}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a sulfur protecting group; and n is 0, 1, 2, 3, 4, or 5;

provided that at least one of $R^1$ and $R^2$ is a non-hydrogen group; and provided that neither $R^1$ or $R^2$ is benzyl.

In certain embodiments of Formula (II), $R^2$ and either $R^{N3}$ or $R^{N4}$ are joined together with the intervening atoms to form optionally substituted heterocyclyl. In certain embodiments, $R^1$ and $R^{N2}$ are joined together with the intervening atoms to form optionally substituted heterocyclyl. In other embodiments, $R^3$ and $R^{N1}$ are joined together with the intervening atoms to form optionally substituted heterocyclyl.

In certain embodiments, a compound of Formula (II) is of one of the following formulae:

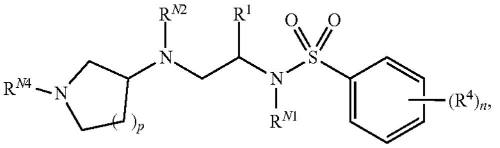

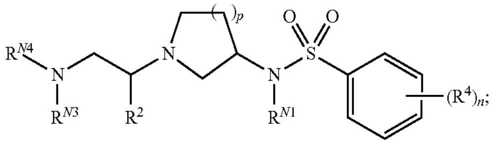

or a pharmaceutically acceptable salt, hydrate, solvate, polymorp, co-crystal, tautomer, stereoisomer, isotopically labeled derivative, or prodrug thereof, wherein:

p is 0, 1, or 2.

In certain embodiments, a compound of Formula (II) is of one of the following formulae:

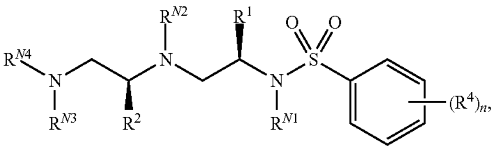

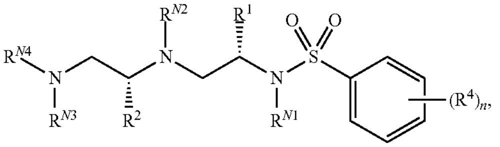

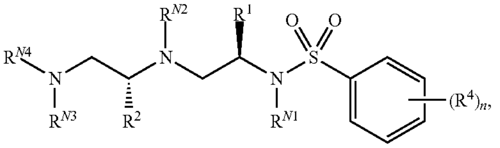

-continued

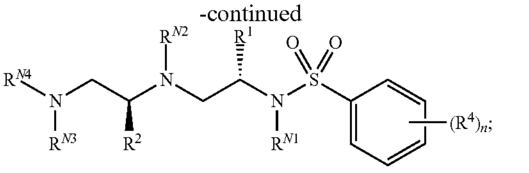

or a pharmaceutically acceptable salt, hydrate, solvate, polymorph, co-crystal, tautomer, stereoisomer, isotopically labeled derivative, or prodrug thereof.

Formula (II) includes the substituents $R^1$, $R^2$, $R^4$, $R^{N1}$, $R^{N2}$, $R^{N3}$, $R^{N4}$ and the variable n. In certain embodiments, $R^1$ is optionally substituted $C_{1-6}$ alkyl; $R^2$ is optionally substituted $C_{1-6}$ alkyl; $R^{N1}$, $R^{N2}$, $R^{N3}$, $R^{N4}$ are H; n is 1, 2, 3, 4, or 5; and each instance of $R^4$ is independently hydrogen, halogen, —CN, —$NO_2$, —$N_3$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^{4a}$, $N(R^{4b})_2$, or —$SR^{4c}$, wherein $R^{4a}$, $R^{4b}$, and $R^{4c}$ are as defined herein. In certain embodiments, $R^1$ is optionally substituted $C_{1-6}$ alkyl; $R^2$ is optionally substituted $C_{1-6}$ alkyl; $R^{N1}$, $R^{N2}$, $R^{N3}$, and $R^{N4}$ are H; n is 1; and $R^4$ is as defined herein. In certain embodiments, $R^1$ is optionally substituted $C_{1-6}$ alkyl; $R^2$ is optionally substituted $C_{1-6}$ alkyl; $R^{N1}$, $R^{N2}$, $R^{N3}$, and $R^{N4}$ are H; n is 1; and $R^4$ is halogen. In certain embodiments, $R^1$ is optionally substituted $C_{1-6}$ alkyl; $R^2$ is optionally substituted $C_{1-6}$ alkyl; $R^{N1}$, $R^{N2}$, $R^{N3}$, and $R^{N4}$ are H; n is 1; $R^4$ is halogen; and $R^4$ is para to the point of attachment of the sulfonamide group to the benzenoid ring. In certain embodiments, $R^1$ is optionally substituted $C_{1-3}$ alkyl; $R^2$ is optionally substituted $C_{1-3}$ alkyl; $R^{N1}$, $R^{N2}$, $R^{N3}$, and $R^{N4}$ are H; n is 1; and $R^4$ is halogen. In certain embodiments, $R^1$ is unsubstituted $C_{1-3}$ alkyl; $R^2$ is unsubstituted $C_{1-3}$ alkyl; $R^{N1}$, $R^{N2}$, $R^{N3}$, and $R^{N4}$ are H; n is 1; and $R^4$ is halogen. In certain embodiments, $R^1$ is selected from the group consisting of methyl, ethyl, propyl, iso-propyl, butyl, iso-butyl, sec-butyl, and tert-butyl; $R^2$ is selected from the group consisting of methyl, ethyl, propyl, iso-propyl, butyl, iso-butyl, sec-butyl, and tert-butyl; $R^{N1}$, $R^{N2}$, $R^{N3}$, and $R^{N4}$ are H; n is 1; and $R^4$ is halogen. In certain embodiments, $R^1$ is iso-propyl; $R^2$ is iso-propyl; $R^{N}$, $R^{N2}$, $R^{N3}$, and $R^{N4}$ are H; n is 1; and $R^4$ is halogen. In certain embodiments, $R^1$ is iso-propyl; $R^2$ is iso-propyl; $R^{N1}$, $R^{N2}$, $R^{N3}$, and $R^{N4}$ are H; n is 1; and $R^4$ is iodo (I). In certain embodiments, $R^1$ is iso-propyl; $R^2$ is iso-propyl; $R^{N1}$, $R^{N2}$, $R^{N3}$, and $R^{N4}$ are H; n is 1; $R^4$ is iodo (I); and $R^4$ is para to the point of attachment of the sulfonamide group to the benzenoid ring.

In certain embodiments, $R^1$ is optionally substituted $C_{1-6}$ alkyl; $R^2$ is optionally substituted $C_{1-6}$ alkyl; $R^{N1}$, $R^{N2}$, $R^{N3}$, and $R^{N4}$ are H; n is 1; and $R^4$ is optionally substituted alkyl. In certain embodiments, $R^1$ is optionally substituted $C_{1-6}$ alkyl; $R^2$ is optionally substituted $C_{1-6}$ alkyl; $R^{N1}$, $R^{N2}$, $R^{N3}$, and $R^{N4}$ are H; n is 1; and $R^4$ is optionally substituted $C_{1-6}$ alkyl. In certain embodiments, $R^1$ is optionally substituted $C_{1-6}$ alkyl; $R^2$ is optionally substituted $C_{1-6}$ alkyl; $R^{N1}$, $R^{N2}$, $R^{N3}$, and $R^{N4}$ are H; n is 1; and $R^4$ is unsubstituted $C_{1-6}$ alkyl.

In certain embodiments, $R^1$ is optionally substituted $C_{1-6}$ alkyl; $R^2$ is optionally substituted $C_{1-6}$ alkyl; $R^{N1}$, $R^{N2}$, $R^{N3}$ and $R^{N4}$ are H; n is 1; $R^4$ is unsubstituted $C_{1-6}$ alkyl; and $R^4$ is para to the point of attachment of the sulfonamide group to the benzenoid ring. In certain embodiments, $R^1$ is optionally substituted $C_{1-6}$ alkyl; $R^2$ is optionally substituted $C_{1-6}$ alkyl; $R^{N1}$, $R^{N2}$, $R^{N3}$, and $R^{N4}$ are H; n is 1; and $R^4$ is selected from the group consisting of methyl, ethyl, propyl, iso-propyl, butyl, iso-butyl, sec-butyl, and tert-butyl. In certain embodiments, $R^1$ is optionally substituted $C_{1-3}$ alkyl; $R^2$ is optionally substituted $C_{1-3}$ alkyl; $R^{N1}$, $R^{N2}$, $R^{N3}$, and $R^{N4}$ are H; n is 1; and $R^4$ is optionally substituted $C_{1-6}$ alkyl. In certain embodiments, $R^1$ is unsubstituted $C_{1-3}$ alkyl; $R^2$ is unsubstituted $C_{1-3}$ alkyl; $R^{N1}$, $R^{N2}$, $R^{N3}$, and $R^{N4}$ are H; n is 1; and $R^4$ is optionally substituted $C_{1-6}$ alkyl. In certain embodiments, $R^1$ is selected from the group consisting of methyl, ethyl, propyl, iso-propyl, butyl, iso-butyl, sec-butyl, and tert-butyl; $R^2$ is selected from the group consisting of methyl, ethyl, propyl, iso-propyl, butyl, iso-butyl, sec-butyl, and tert-butyl; $R^{N1}$, $R^{N2}$, $R^{N3}$, and $R^{N4}$ are H; n is 1; and $R^4$ is optionally substituted $C_{1-6}$ alkyl. In certain embodiments, $R^1$ is methyl; $R^2$ is iso-propyl; $R^{N1}$, $R^{N2}$, $R^{N3}$, and $R^{N4}$ are H; n is 1; and $R^4$ is optionally substituted $C_{1-6}$ alkyl. In certain embodiments, $R^1$ is methyl; $R^2$ is iso-propyl; $R^{N1}$, $R^{N2}$, $R^{N3}$, and $R^{N4}$ are H; n is 1; and $R^4$ is optionally substituted $C_{1-6}$ alkyl. In certain embodiments, $R^1$ is methyl; $R^2$ is iso-propyl; $R^{N1}$, $R^{N2}$, $R^{N3}$, and $R^{N4}$ are H; n is 1; and $R^4$ is unsubstituted $C_{1-6}$ alkyl. In certain embodiments, $R^1$ is methyl; $R^2$ is iso-propyl; $R^{N1}$, $R^{N2}$, $R^{N3}$, and $R^{N4}$ are H; n is 1; and $R^4$ is selected from the group consisting of methyl, ethyl, propyl, iso-propyl, butyl, iso-butyl, sec-butyl, and tert-butyl. In certain embodiments, $R^1$ is methyl; $R^2$ is iso-propyl; $R^{N1}$, $R^{N2}$, $R^{N3}$, and $R^{N4}$ are H; n is 1; and $R^4$ is tert-butyl. In certain embodiments, $R^1$ is methyl; $R^2$ is iso-propyl; $R^{N1}$, $R^{N2}R^{N3}$, and $R^{N4}$ are H; n is 1; $R^4$ is tert-butyl; and $R^4$ is para to the point of attachment of the sulfonamide group to the benzenoid ring.

In certain embodiments, the compound of Formula (II) is of the following formula:

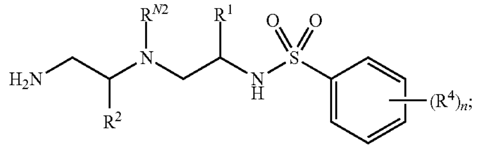

or a pharmaceutically acceptable salt, hydrate, solvate, polymorph, co-crystal, tautomer, stereoisomer, isotopically labeled derivative, or prodrug thereof.

In certain embodiments, the compound of Formula (II) is of one of the following formulae:

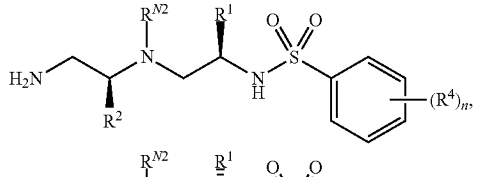

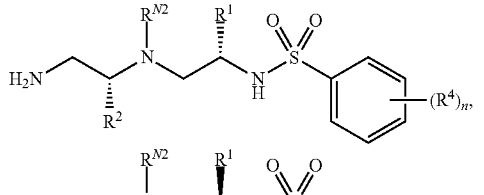

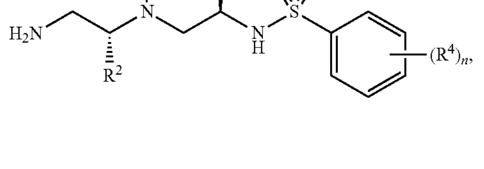

-continued

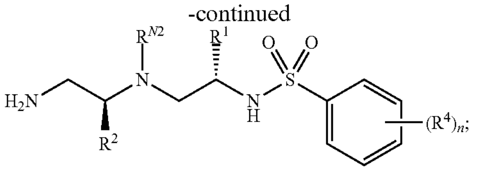

or a pharmaceutically acceptable salt, hydrate, solvate, polymorph, co-crystal, tautomer, stereoisomer, isotopically labeled derivative, or prodrug thereof.

In certain embodiments, the compound of Formula (II) is of the following formula:

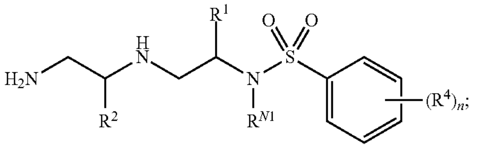

or a pharmaceutically acceptable salt, hydrate, solvate, polymorph, co-crystal, tautomer, stereoisomer, isotopically labeled derivative, or prodrug thereof.

In certain embodiments, the compound of Formula (II) is of one of the following formulae:

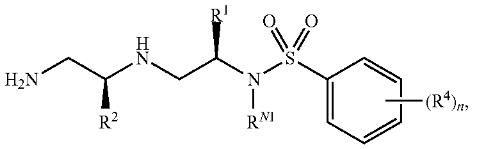

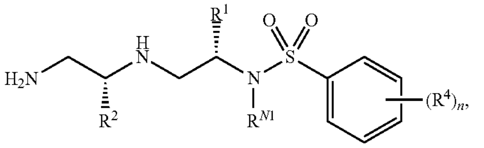

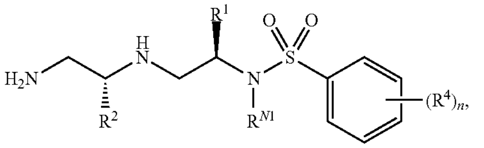

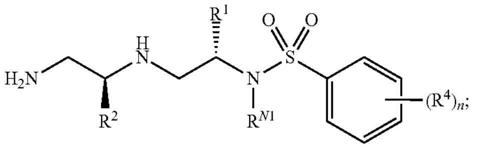

or a pharmaceutically acceptable salt, hydrate, solvate, polymorph, co-crystal, tautomer, stereoisomer, isotopically labeled derivative, or prodrug thereof.

In certain embodiments, $R^{N1}$, $R^{N2}$, $R^{N3}$, and $R^{N4}$ are hydrogen; and the compound of Formula (II) is of Formula (II-a):

(II-a)

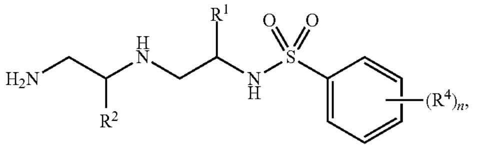

or a pharmaceutically acceptable salt, hydrate, solvate, polymorph, co-crystal, tautomer, stereoisomer, isotopically labeled derivative, or prodrug thereof.

In certain embodiments, a compound of Formula (II-a) is of one of the following formulae:

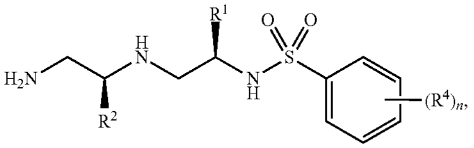

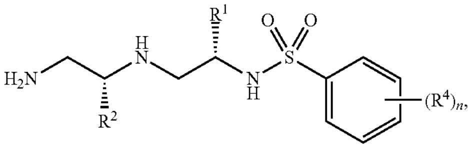

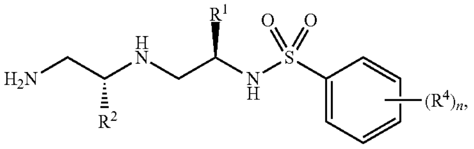

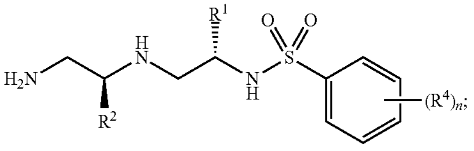

or a pharmaceutically acceptable salt, hydrate, solvate, polymorph, co-crystal, tautomer, stereoisomer, isotopically labeled derivative, or prodrug thereof.

In certain embodiments, the compound of Formula (II) is of Formula (II-b) or (II-c):

(II-b)

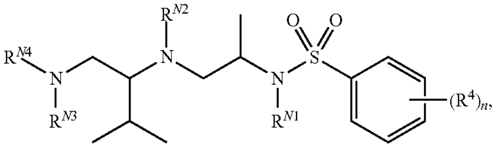

(II-c)

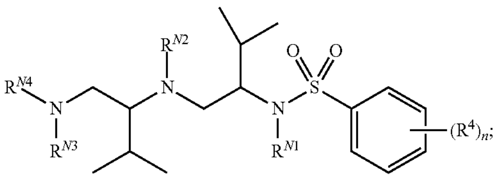

or a pharmaceutically acceptable salt, hydrate, solvate, polymorph, co-crystal, tautomer, stereoisomer, isotopically labeled derivative, or prodrug thereof.

In certain embodiments, the compound of Formula (II-b) is of one of the following formulae:

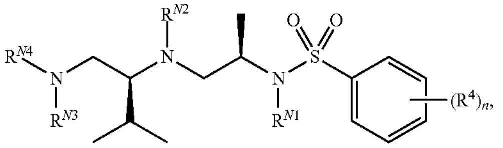

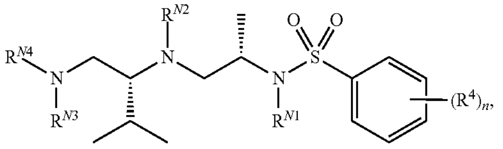

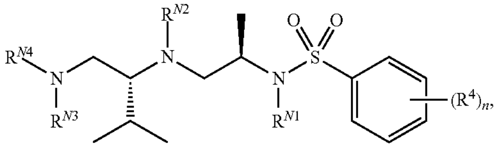

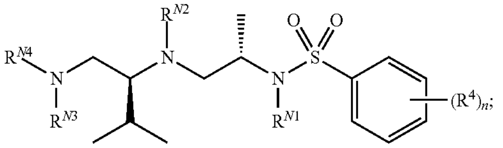

or a pharmaceutically acceptable salt, hydrate, solvate, polymorph, co-crystal, tautomer, stereoisomer, isotopically labeled derivative, or prodrug thereof.

In certain embodiments, the compound of Formula (II-c) is of one of the following formulae:

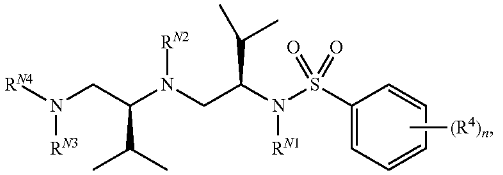

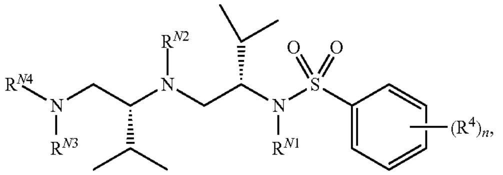

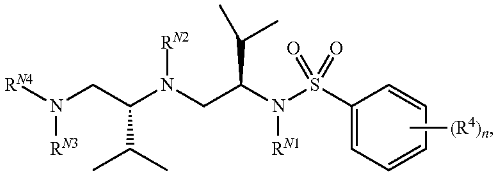

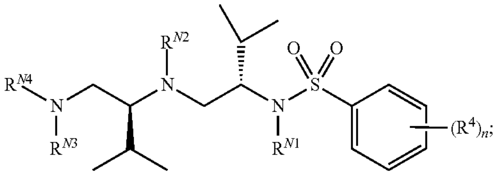

or a pharmaceutically acceptable salt, hydrate, solvate, polymorph, co-crystal, tautomer, stereoisomer, isotopically labeled derivative, or prodrug thereof.

In certain embodiments, $R^{N1}$, $R^{N2}$, $R^{N3}$, and $R^{N4}$ are hydrogen; and the compound of Formula (II-a) is of Formula (II-d) or (II-e):

(II-d)

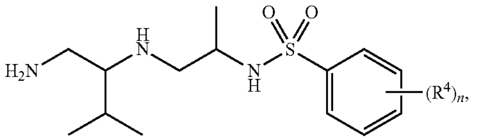

(II-e)

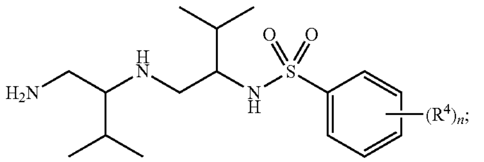

In certain embodiments, a compound of Formula (II-d) is of one of the following formulae:

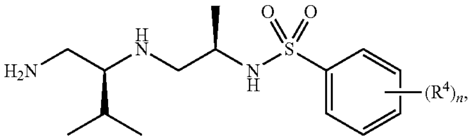

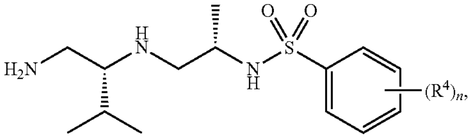

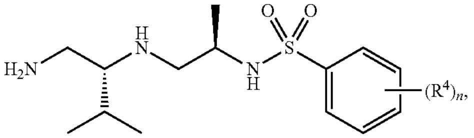

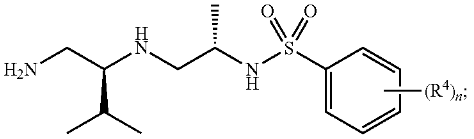

or a pharmaceutically acceptable salt, hydrate, solvate, polymorph, co-crystal, tautomer, stereoisomer, isotopically labeled derivative, or prodrug thereof.

In certain embodiments, a compound of Formula (II-e) is of one of the following formulae:

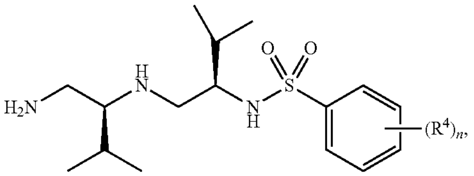

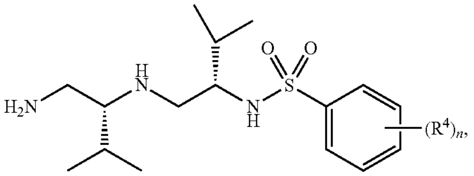

-continued

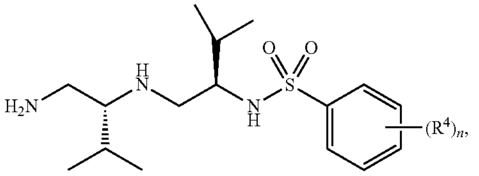

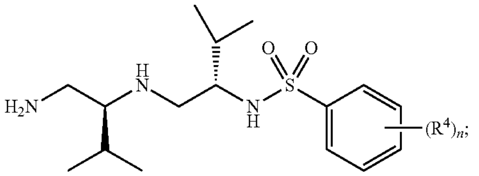

or a pharmaceutically acceptable salt, hydrate, solvate, polymorph, co-crystal, tautomer, stereoisomer, isotopically labeled derivative, or prodrug thereof.

In certain embodiments, the compound of Formula (II) is of the following formula:

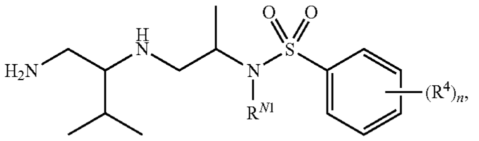

or a pharmaceutically acceptable salt, hydrate, solvate, polymorph, co-crystal, tautomer, stereoisomer, isotopically labeled derivative, or prodrug thereof.

In certain embodiments, the compound of Formula (II) is of one of the following formulae:

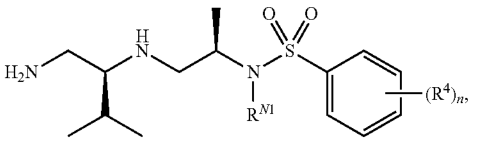

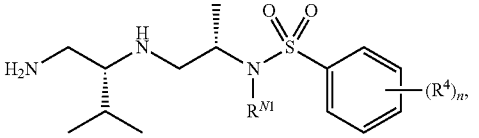

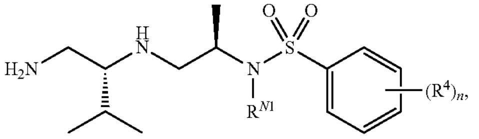

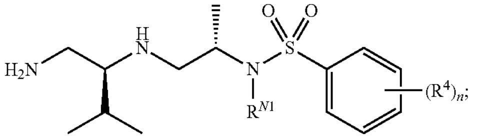

or a pharmaceutically acceptable salt, hydrate, solvate, polymorph, co-crystal, tautomer, stereoisomer, isotopically labeled derivative, or prodrug thereof.

In certain embodiments, the compound of Formula (II) is of the following formula:

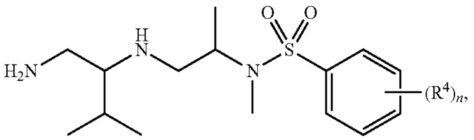

or a pharmaceutically acceptable salt, hydrate, solvate, polymorph, co-crystal, tautomer, stereoisomer, isotopically labeled derivative, or prodrug thereof.

In certain embodiments, the compound of Formula (II) is of one of the following formulae:

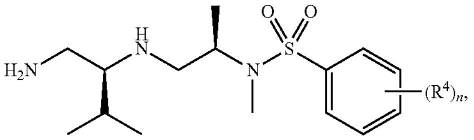

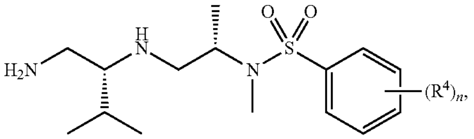

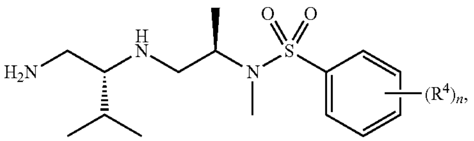

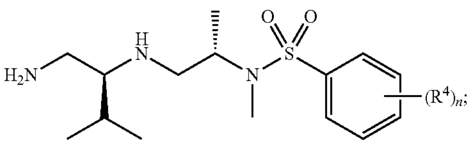

or a pharmaceutically acceptable salt, hydrate, solvate, polymorph, co-crystal, tautomer, stereoisomer, isotopically labeled derivative, or prodrug thereof.

In certain embodiments, the compound of Formula (II) is of the following formula:

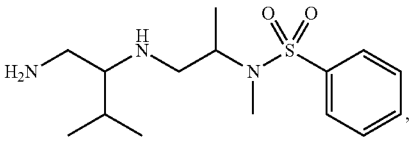

or a pharmaceutically acceptable salt, hydrate, solvate, polymorph, co-crystal, tautomer, stereoisomer, isotopically labeled derivative, or prodrug thereof.

In certain embodiments, the compound of Formula (II) is of one of the following formulae:

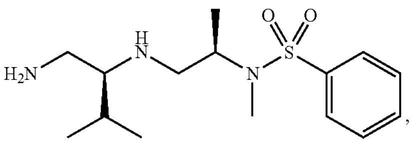

-continued

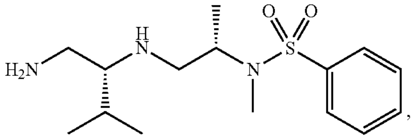

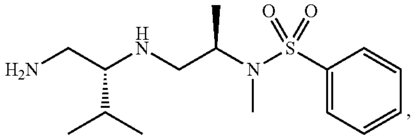

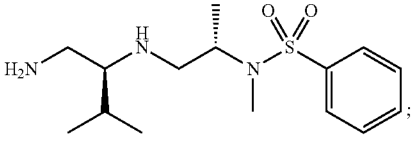

or a pharmaceutically acceptable salt, hydrate, solvate, polymorph, co-crystal, tautomer, stereoisomer, isotopically labeled derivative, or prodrug thereof.

In certain embodiments, n is 1; and the compound of Formula (II) is of Formula (II-f):

(II-f)

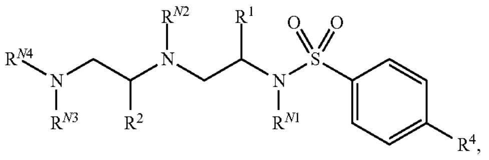

or a pharmaceutically acceptable salt, hydrate, solvate, polymorph, co-crystal, tautomer, stereoisomer, isotopically labeled derivative, or prodrug thereof.

In certain embodiments, a compound of Formula (II-f) is of one of the following formulae:

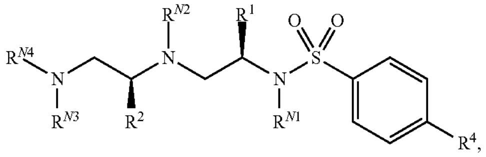

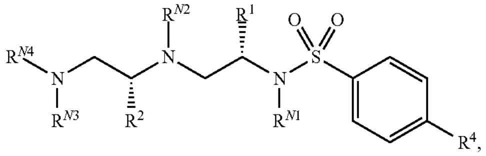

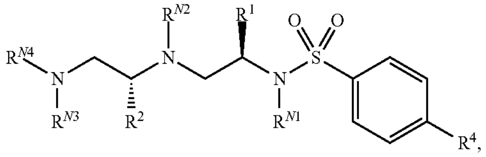

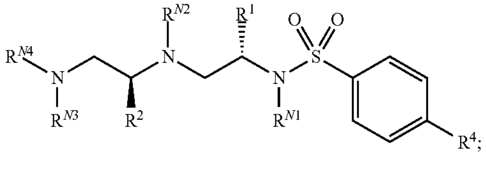

or a pharmaceutically acceptable salt, hydrate, solvate, polymorph, co-crystal, tautomer, stereoisomer, isotopically labeled derivative, or prodrug thereof.

In certain embodiments, the compound of Formula (II) is of Formula (II-g):

(II-g)

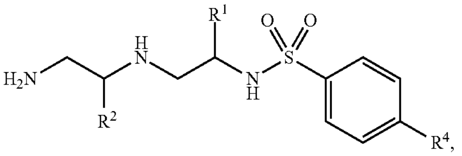

or a pharmaceutically acceptable salt, hydrate, solvate, polymorph, co-crystal, tautomer, stereoisomer, isotopically labeled derivative, or prodrug thereof.

In certain embodiments, the compound of Formula (II-g) is of one of the following formulae:

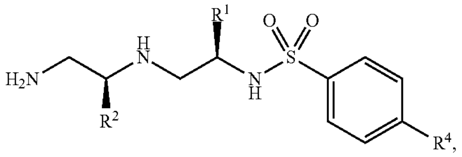

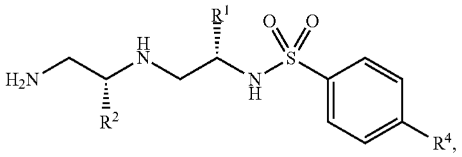

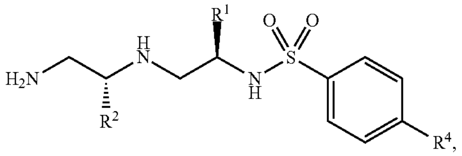

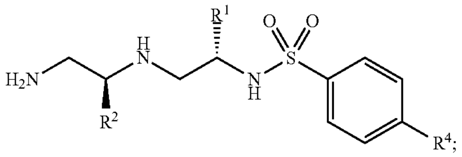

or a pharmaceutically acceptable salt, hydrate, solvate, polymorph, co-crystal, tautomer, stereoisomer, isotopically labeled derivative, or prodrug thereof.

In certain embodiments, the compound of Formula (II) is of Formula (II-h) or (II-i):

(II-h)

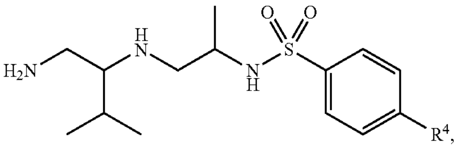

-continued (II-i)

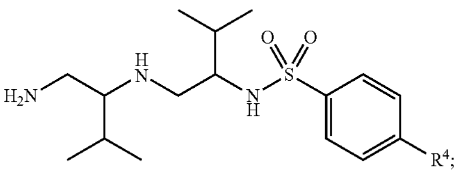

or a pharmaceutically acceptable salt, hydrate, solvate, polymorph, co-crystal, tautomer, stereoisomer, isotopically labeled derivative, or prodrug thereof.

In certain embodiments, a compound of Formula (II-h) is of one of the following formulae:

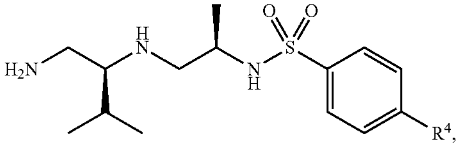

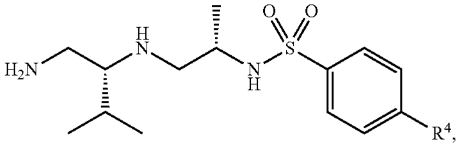

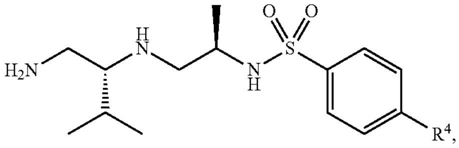

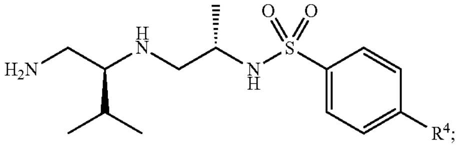

or a pharmaceutically acceptable salt, hydrate, solvate, polymorph, co-crystal, tautomer, stereoisomer, isotopically labeled derivative, or prodrug thereof.

In certain embodiments, a compound of Formula (II-i) is of one of the following formulae:

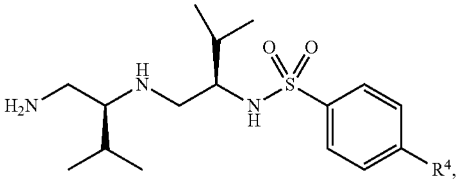

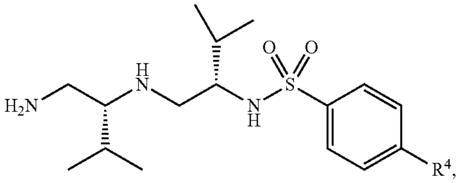

-continued

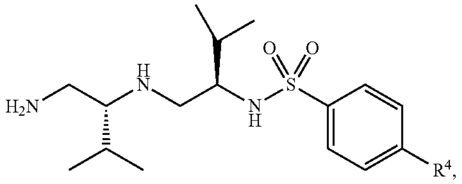

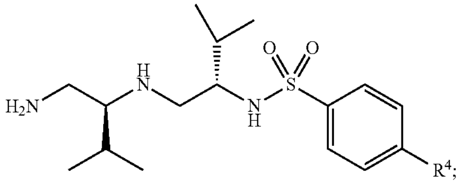

or a pharmaceutically acceptable salt, hydrate, solvate, polymorph, co-crystal, tautomer, stereoisomer, isotopically labeled derivative, or prodrug thereof.

In certain embodiments, the compound of Formula (II) is of Formula (II-j), (II-k), (II-l), or (II-m):

(II-j)

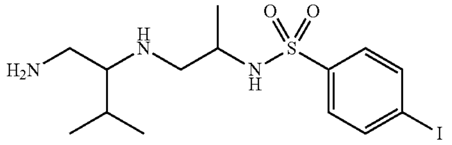

(II-k)

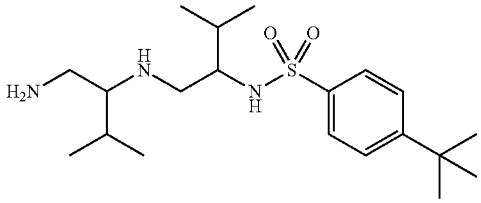

(II-l)

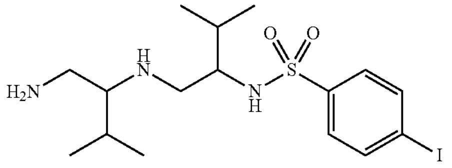

(II-m);

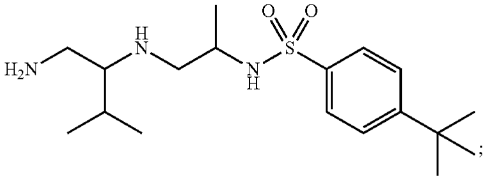

or a pharmaceutically acceptable salt, hydrate, solvate, polymorph, co-crystal, tautomer, stereoisomer, isotopically labeled derivative, or prodrug thereof.

In certain embodiments, a compound of Formula (II-l) is of one of the following formulae:

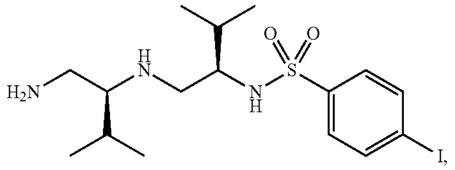

,

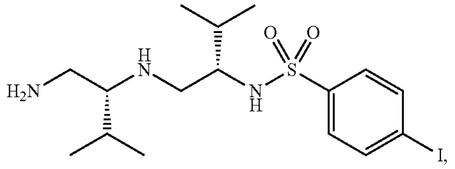

,

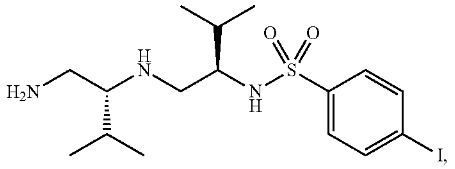

,

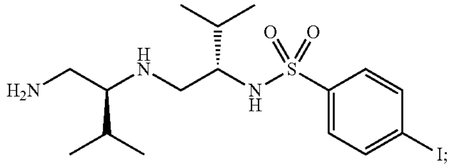

;

or a pharmaceutically acceptable salt, hydrate, solvate, polymorph, co-crystal, tautomer, stereoisomer, isotopically labeled derivative, or prodrug thereof.

In certain embodiments, a compound of Formula (II-m) is of one of the following formulae:

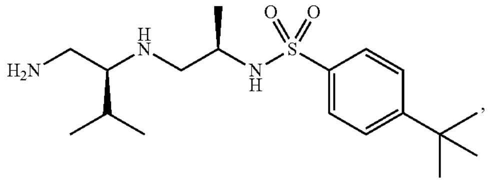

,

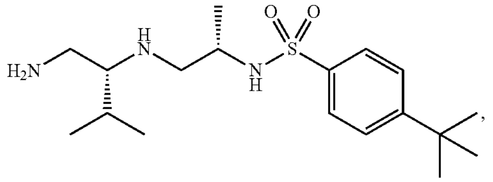

,

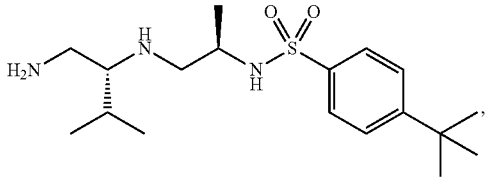

,

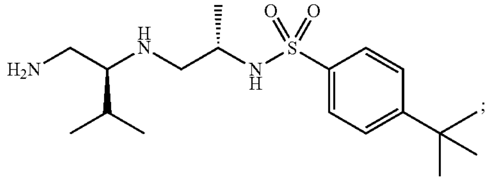

;

or a pharmaceutically acceptable salt, hydrate, solvate, polymorph, co-crystal, tautomer, stereoisomer, isotopically labeled derivative, or prodrug thereof.

In certain embodiments of the invention, a compound of Formula (I) is of one of the following formulae:

(2470-23)

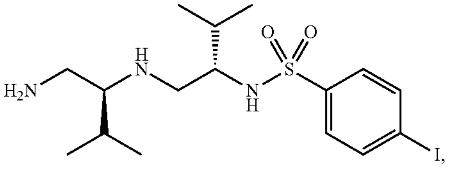

, (2470-15)

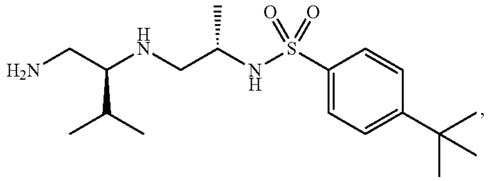

, (2470-51)

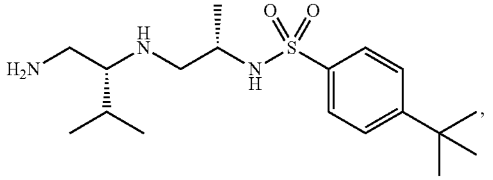

,

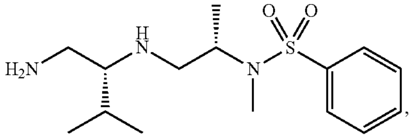 [SMILES: CC(C)C(CN)NCC(C)N(C)S(=O)(=O)c1ccccc1]

,

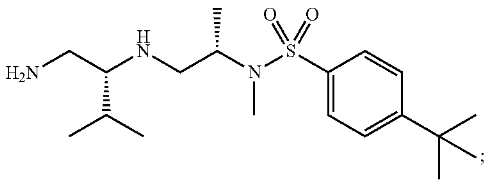

;

or a pharmaceutically acceptable salt, hydrate, solvate, polymorph, co-crystal, tautomer, stereoisomer, isotopically labeled derivative, or prodrug thereof.

In a particular embodiment, a compound of Formula (I) is of the following formula:

(2470-51)

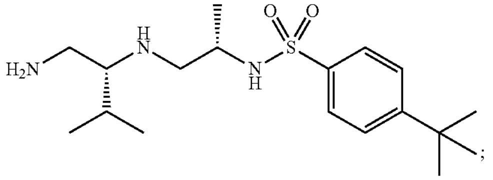

;

or a pharmaceutically acceptable salt, hydrate, solvate, polymorph, co-crystal, tautomer, stereoisomer, isotopically labeled derivative, or prodrug thereof.

In certain embodiments, $R^3$ is optionally substituted naphthyl; and the compound of Formula (I) is of Formula (III):

(III)

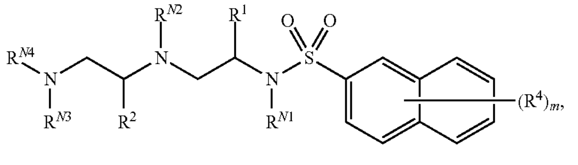

or a pharmaceutically acceptable salt, hydrate, solvate, polymorph, co-crystal, tautomer, stereoisomer, isotopically labeled derivative, or prodrug thereof, wherein:

$R^1$ is hydrogen, optionally substituted $C_{1-6}$ alkyl, optionally substituted carbocyclyl, optionally substituted heterocyclyl, optionally substituted heterocyclylalkyl, or optionally substituted heteroaralkyl;

$R^2$ is hydrogen, optionally substituted $C_{1-6}$ alkyl, optionally substituted carbocyclyl, optionally substituted heterocyclyl, optionally substituted heterocyclylalkyl, or optionally substituted heteroaralkyl;

$R^{N1}$, $R^{N2}$, $R^{N3}$, and $R^{N4}$ are each independently hydrogen, optionally substituted alkyl, optionally substituted aryl, optionally substituted acyl, or a nitrogen protecting group; or optionally $R^{N3}$ and $R^{N4}$ are joined together with the intervening atoms to form optionally substituted heterocyclyl or optionally substituted heteroaryl;

each instance of $R^4$ is independently hydrogen, halogen, —CN, —$NO_2$, —$N_3$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^{4a}$, —$N(R^{4b})_2$, or —$SR^{4c}$;

each instance of $R^{4a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or an oxygen protecting group;

each instance of $R^{4b}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group; or optionally two $R^{3b}$ are joined together with the intervening atoms to form optionally substituted heterocyclyl or optionally substituted heteroaryl;

each instance of $R^{4c}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a sulfur protecting group; and m is 1, 2, 3, 4, 5, 6, or 7;

optionally wherein $R^2$ and either $R^{N3}$ or $R^{N4}$ are joined together with the intervening atoms to form optionally substituted heterocyclyl; or optionally wherein $R^1$ and $R^{N2}$ are joined together with the intervening atoms to form optionally substituted heterocyclyl; or optionally wherein $R^3$ and $R^{N1}$ are joined together with the intervening atoms to form optionally substituted heterocyclyl;

provided that at least one of $R^1$ and $R^2$ is a non-hydrogen group; and provided that neither $R^1$ or $R^2$ is benzyl.

In certain embodiments, the compound of Formula (I) is of Formula (III):

(III)

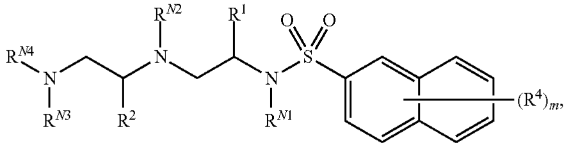

or a pharmaceutically acceptable salt, hydrate, solvate, polymorph, co-crystal, tautomer, stereoisomer, isotopically labeled derivative, or prodrug thereof, wherein:

$R^1$ is hydrogen, optionally substituted $C_{1-6}$ alkyl, optionally substituted carbocyclyl, optionally substituted heterocyclyl, optionally substituted heterocyclylalkyl, or optionally substituted heteroaralkyl;

$R^2$ is hydrogen, optionally substituted $C_{1-6}$ alkyl, optionally substituted carbocyclyl, optionally substituted heterocyclyl, optionally substituted heterocyclylalkyl, or optionally substituted heteroaralkyl;

$R^{N1}$, $R^{N2}$, $R^{N3}$, and $R^{N4}$ are each independently hydrogen, optionally substituted alkyl, optionally substituted aryl, optionally substituted acyl, or a nitrogen protecting group; or optionally $R^{N3}$ and $R^{N4}$ are joined together with the intervening atoms to form optionally substituted heterocyclyl or optionally substituted heteroaryl;

each instance of $R^4$ is independently hydrogen, halogen, —CN, —$NO_2$, —$N_3$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^{4a}$, —$N(R^{4b})_2$, or —$SR^{4c}$;

each instance of $R^{4a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or an oxygen protecting group;

each instance of $R^{4b}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group; or optionally two $R^{3b}$ are joined together with the intervening atoms to form optionally substituted heterocyclyl or optionally substituted heteroaryl;

each instance of $R^{4c}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a sulfur protecting group; and m is 1, 2, 3, 4, 5, 6, or 7;

provided that at least one of $R^1$ and $R^2$ is a non-hydrogen group; and provided that neither $R^1$ or $R^2$ is benzyl.

In certain embodiments of Formula (III), $R^2$ and either $R^{N3}$ or $R^{N4}$ are joined together with the intervening atoms to form optionally substituted heterocyclyl. In certain embodiments, $R^1$ and $R^{N2}$ are joined together with the intervening atoms to form optionally substituted heterocyclyl. In other embodiments, $R^3$ and $R^{N1}$ are joined together with the intervening atoms to form optionally substituted heterocyclyl.

In certain embodiments, a compound of Formula (III) is of one of the following formulae:

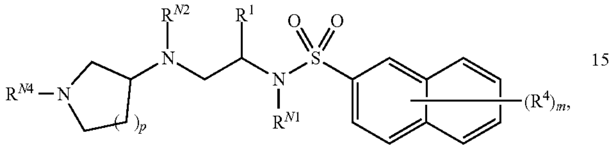

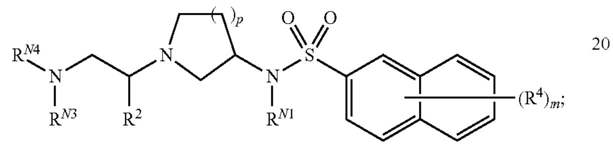

or a pharmaceutically acceptable salt, hydrate, solvate, polymorph, co-crystal, tautomer, stereoisomer, isotopically labeled derivative, or prodrug thereof, wherein:

p is 0, 1, or 2.

In certain embodiments, a compound of Formula (III) is of one of the following formulae:

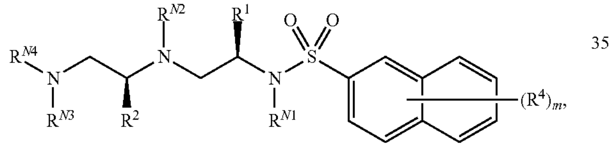

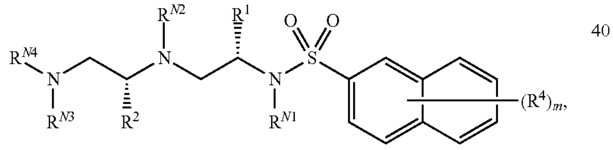

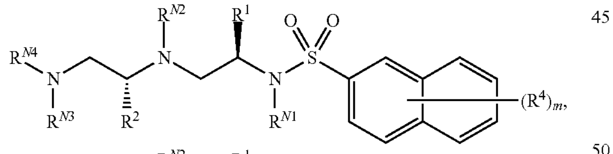

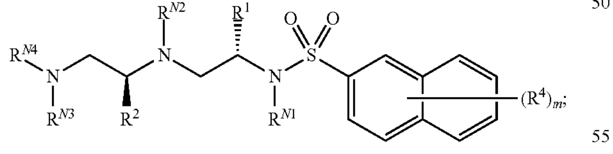

or a pharmaceutically acceptable salt, hydrate, solvate, polymorph, co-crystal, tautomer, stereoisomer, isotopically labeled derivative, or prodrug thereof.

Formula (III) includes the substituents $R^1$, $R^2$, $R^4$, $R^{N1}$, $R^{N2}$, $R^{N3}$, $R^{N4}$ and the variable m. In certain embodiments, $R^1$ is optionally substituted $C_{1-6}$ alkyl; $R^2$ is optionally substituted $C_{1-6}$ alkyl; $R^{N1}$, $R^{N2}$, $R^{N3}$, and $R^{N4}$ are H; m is 1, 2, 3, 4, 5, 6, or 7; and each instance of $R^4$ is independently hydrogen, halogen, —CN, —$NO_2$, —$N_3$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^{4a}$, $N(R^{4b})_2$, or —$SR^{4c}$, wherein $R^{4a}R^{4b}$, and $R^{4c}$ are as defined herein. In certain embodiments, $R^1$ is optionally substituted $C_{1-6}$ alkyl; $R^2$ is optionally substituted $C_{1-6}$alkyl; $R^{N1}$, $R^{N2}$, $R^{N3}$, and $R^{N4}$ are H; and m is 0. In certain embodiments, $R^1$ is optionally substituted $C_{1-6}$ alkyl; $R^2$ is unsubstituted $C_{1-6}$ alkyl; $R^{N1}$, $R^{N2}$, $R^{N3}$, and $R^{N4}$ are H; and m is 0. In certain embodiments, $R^1$ is substituted $C_{1-6}$ alkyl; $R^2$ is unsubstituted $C_{1-6}$ alkyl; $R^{N1}$, $R^{N2}$, $R^{N3}$, and $R^{N4}$ are H; and m is 0. In certain embodiments, $R^1$ is $C_{1-6}$ alkyl substituted with oxygen; $R^2$ is unsubstituted $C_{1-6}$ alkyl; $R^{N1}$, $R^{N2}$, $R^{N3}$, and $R^{N4}$ are H; and m is 0. In certain embodiments, $R^1$ is $C_{1-6}$ alkyl substituted with —OH; $R^2$ is unsubstituted $C_{1-6}$ alkyl; $R^{N1}$, $R^{N2}$, $R^{N3}$, and $R^{N4}$ are H; and m is 0. In certain embodiments, $R^1$ is —$CH_2(CH_2)_{0-4}OR^O$, wherein $R^O$ is hydrogen, optionally substituted $C_{1-6}$ alkyl, optionally substituted acyl, or an oxygen protecting group; $R^2$ is unsubstituted $C_{1-6}$ alkyl; $R^{N1}$, $R^{N2}$, $R^{N3}$, and $R^{N4}$ are H; and m is 0. In certain embodiments, $R^1$ is —$CH_2(CH_2)_{0-4}$ $OR^O$, wherein $R^O$ is optionally substituted $C_{1-6}$ alkyl; $R^2$ is unsubstituted $C_{1-6}$ alkyl; $R^{N1}$, $R^{N2}R^{N3}$, and $R^{N4}$ are H; and m is 0. In certain embodiments, $R^1$ is —$CH_2(CH_2)_{0-4}OR^O$, wherein $R^O$ is hydrogen; $R^2$ is unsubstituted $C_{1-6}$ alkyl; $R^{N1}$, $R^{N2}$, $R^{N3}$, and $R^{N4}$ are H; and m is 0. In certain embodiments, $R^1$ is —$CH_2(CH_2)_{0-4}OR^O$, wherein $R^O$ is hydrogen; $R^2$ is selected from the group consisting of methyl, ethyl, propyl, iso-propyl, butyl, iso-butyl, sec-butyl, and tert-butyl; $R^{N1}$, $R^{N2}$, $R^{N3}$, and $R^{N4}$ are H; and m is 0. In certain embodiments, $R^1$ is —$CH_2(CH_2)_{0-4}$ OH; $R^2$ is iso-butyl; $R^{N1}$, $R^{N2}$, $R^{N3}$, and $R^{N4}$ are H; and m is 0. In certain embodiments, $R^1$ is —$CH_2CH_2OH$; $R^2$ is selected from the group consisting of methyl, ethyl, propyl, iso-propyl, butyl, iso-butyl, sec-butyl, and tert-butyl; $R^{N1}$, $R^{N2}$, $R^{N3}$, and $R^{N4}$ are H; and m is 0. In certain embodiments, $R^1$ is —$CH_2CH_2OH$; $R^2$ is iso-butyl; $R^{N1}$, $R^{N2}$, $R^{N3}$, and $R^{N4}$ are H; and m is 0. In certain embodiments, $R^1$ is —$CH_2CH_2OH$; $R^2$ is iso-butyl; $R^{N1}$, $R^{N2}$, $R^{N3}$, and $R^{N4}$ are H; m is 1, 2, 3, 4, 5, 6, or 7; and $R^4$ is as defined herein.

In certain embodiments, $R^1$ is optionally substituted $C_{1-3}$ alkyl; $R^2$ is optionally substituted $C_{1-6}$alkyl; $R^{N1}$, $R^{N2}$, $R^{N3}$, and $R^{N4}$ are H; and m is 0. In certain embodiments, $R^1$ is unsubstituted $C_{1-3}$ alkyl; $R^2$ is unsubstituted $C_{1-6}$ alkyl; $R^{N1}$, $R^{N2}$, $R^{N3}$, and $R^{N4}$ are H; and m is 0. In certain embodiments, $R^1$ is selected from the group consisting of methyl, ethyl, propyl, iso-propyl; $R^2$ is selected from the group consisting of methyl, ethyl, propyl, iso-propyl, butyl, iso-butyl, sec-butyl, and tert-butyl; $R^{N1}$, $R^{N2}$, $R^{N3}$, and $R^{N4}$ are H; and m is 0. In certain embodiments, $R^1$ is methyl; $R^2$ is selected from the group consisting of methyl, ethyl, propyl, iso-propyl, butyl, iso-butyl, sec-butyl, and tert-butyl; $R^{N1}$, $R^{N2}$, $R^{N3}$, and $R^{N4}$ are H; and m is 0. In certain embodiments, $R^1$ is selected from the group consisting of methyl, ethyl, propyl, iso-propyl; $R^2$ is iso-butyl; $R^{N1}$, $R^{N2}$, $R^{N3}$, and $R^{N4}$ are H; and m is 0. In certain embodiments, $R^1$ is methyl; $R^2$ is iso-butyl; $R^{N1}$, $R^{N2}$, $R^{N3}$, and $R^{N4}$ are H; and m is 0. In certain embodiments, $R^1$ is methyl; $R^2$ is iso-butyl; $R^{N1}$, $R^{N2}$, $R^{N3}$, and $R^{N4}$ are H; m is 1, 2, 3, 4, 5, 6, or 7; and $R^4$ is as defined herein.

In certain embodiments, the compound of Formula (III) is of the following formula:

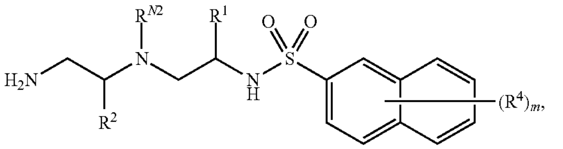

or a pharmaceutically acceptable salt, hydrate, solvate, polymorph, co-crystal, tautomer, stereoisomer, isotopically labeled derivative, or prodrug thereof.

In certain embodiments, the compound of Formula (III) is of one of the following formulae:

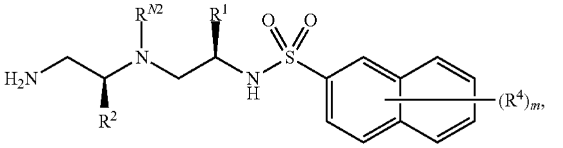

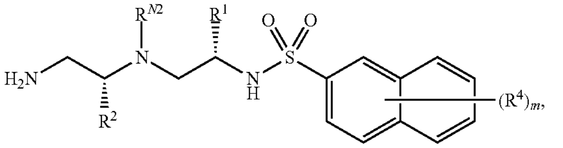

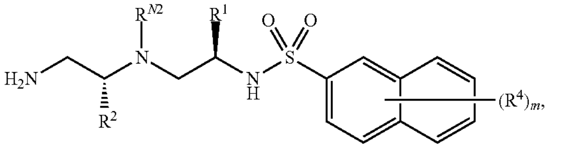

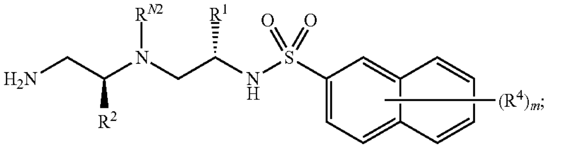

or a pharmaceutically acceptable salt, hydrate, solvate, polymorph, co-crystal, tautomer, stereoisomer, isotopically labeled derivative, or prodrug thereof.

In certain embodiments, the compound of Formula (I) is of Formula (III). In certain embodiments, $R^{N1}$, $R^{N2}$, $R^{N3}$, and $R^{N4}$ are hydrogen, and the compound of Formula (III) is of Formula (III-a):

(III-a)

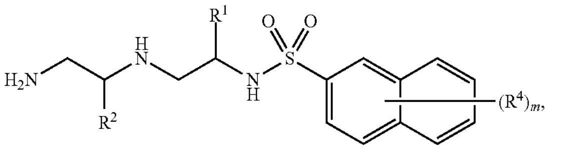

or a pharmaceutically acceptable salt, hydrate, solvate, polymorph, co-crystal, tautomer, stereoisomer, isotopically labeled derivative, or prodrug thereof.

In certain embodiments, a compound of Formula (III-a) is of one of the following formulae:

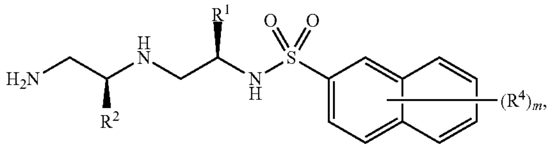

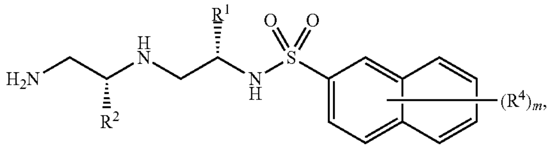

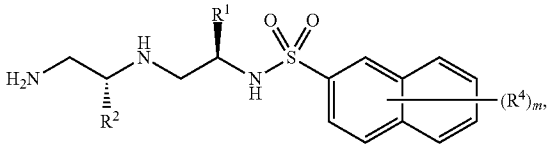

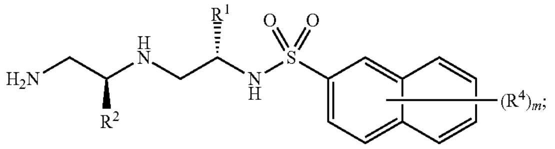

or a pharmaceutically acceptable salt, hydrate, solvate, polymorph, co-crystal, tautomer, stereoisomer, isotopically labeled derivative, or prodrug thereof.

In certain embodiments, the compound of Formula (III) is of Formula (III-b) or (III-c):

(III-b)

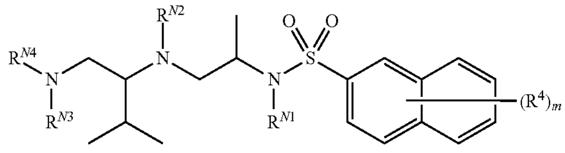

(III-c)

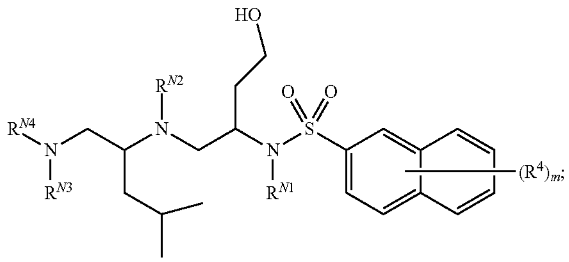

or a pharmaceutically acceptable salt, hydrate, solvate, polymorph, co-crystal, tautomer, stereoisomer, isotopically labeled derivative, or prodrug thereof.

In certain embodiments, a compound of Formula (III-b) is of one of the following formulae:

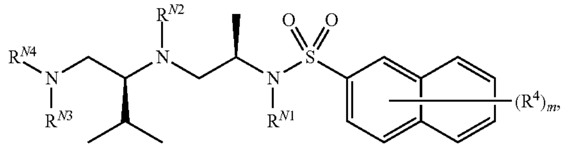

-continued

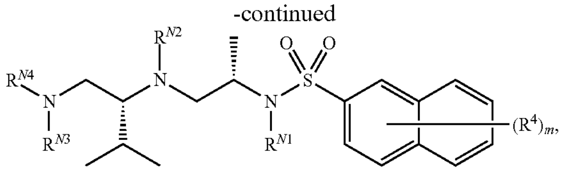

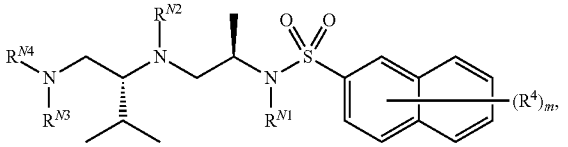

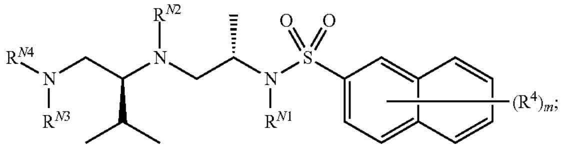

or a pharmaceutically acceptable salt, hydrate, solvate, polymorph, co-crystal, tautomer, stereoisomer, isotopically labeled derivative, or prodrug thereof.

In certain embodiments, a compound of Formula (III-c) is of one of the following formulae:

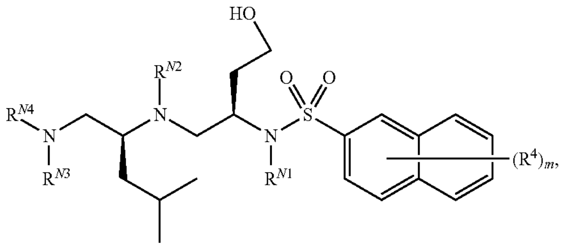

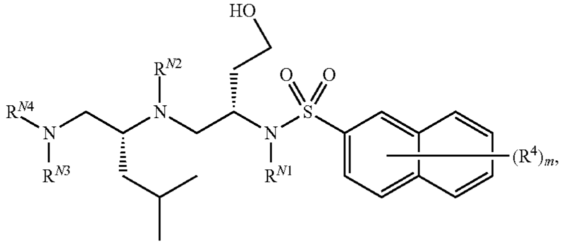

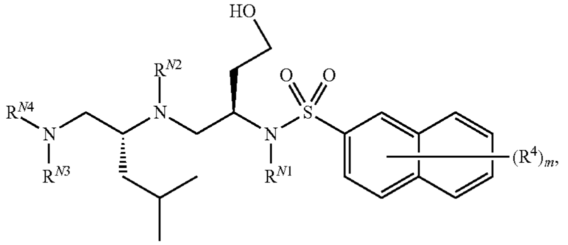

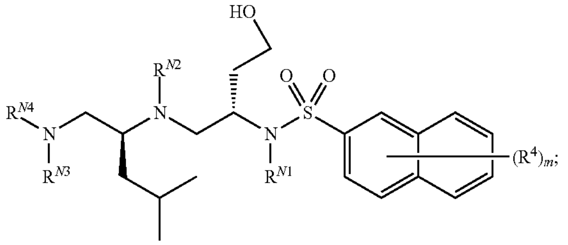

or a pharmaceutically acceptable salt, hydrate, solvate, polymorph, co-crystal, tautomer, stereoisomer, isotopically labeled derivative, or prodrug thereof.

In certain embodiments, the compound of Formula (III) is of Formula (III-d) or (III-e):

(III-d)

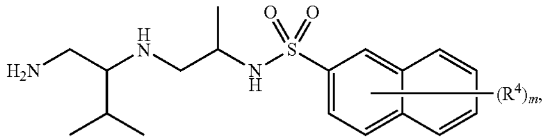

(III-e)

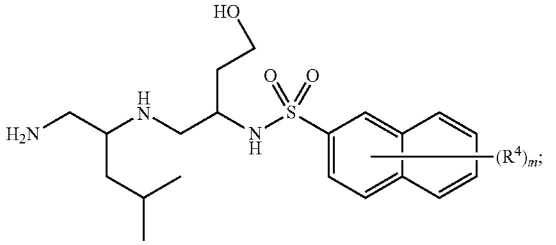

or a pharmaceutically acceptable salt, hydrate, solvate, polymorph, co-crystal, tautomer, stereoisomer, isotopically labeled derivative, or prodrug thereof.

In certain embodiments, a compound of Formula (III-d) is of one of the following formulae:

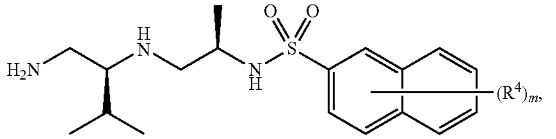

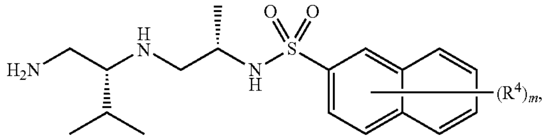

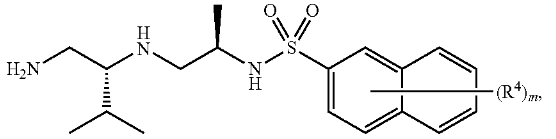

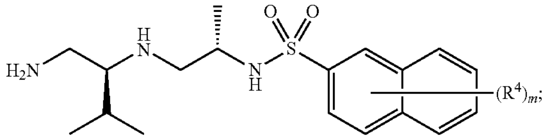

or a pharmaceutically acceptable salt, hydrate, solvate, polymorph, co-crystal, tautomer, stereoisomer, isotopically labeled derivative, or prodrug thereof.

In certain embodiments, a compound of Formula (III-e) is of one of the following formulae:

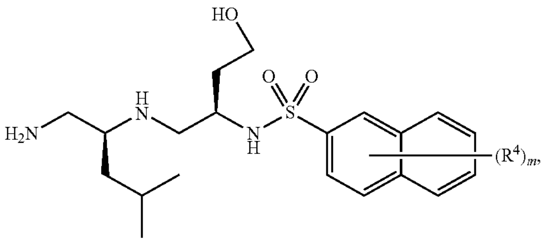

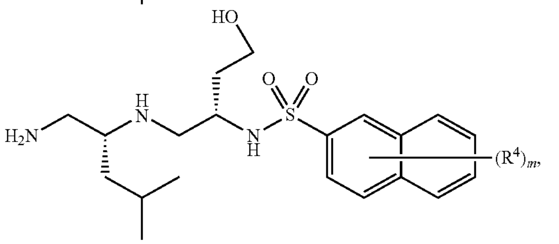

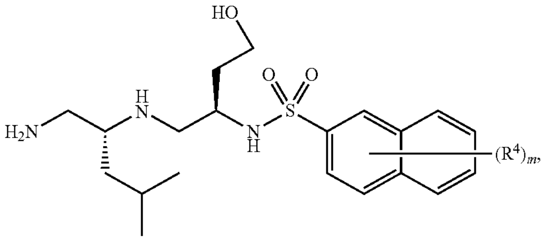

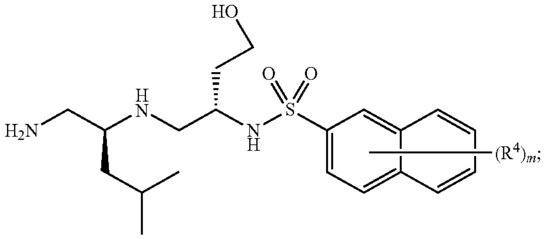

or a pharmaceutically acceptable salt, hydrate, solvate, polymorph, co-crystal, tautomer, stereoisomer, isotopically labeled derivative, or prodrug thereof.

In certain embodiments, the compound of Formula (III) is of Formula (III-f) or (III-g):

(III-f)

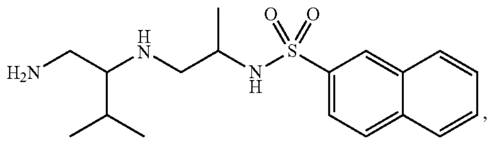

(III-g)

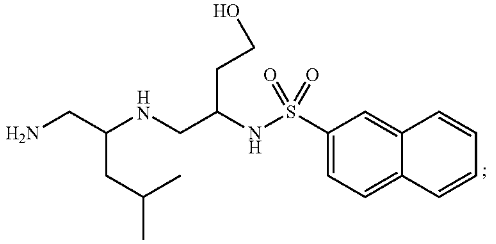

or a pharmaceutically acceptable salt, hydrate, solvate, polymorph, co-crystal, tautomer, stereoisomer, isotopically labeled derivative, or prodrug thereof.

In certain embodiments, a compound of Formula (III-f) is of one of the following formulae:

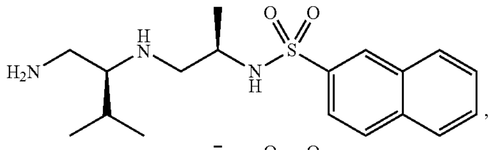

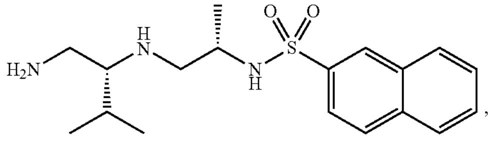

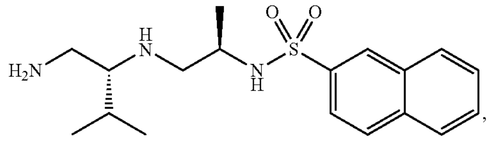

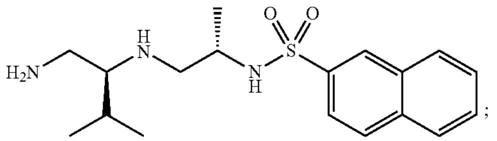

or a pharmaceutically acceptable salt, hydrate, solvate, polymorph, co-crystal, tautomer, stereoisomer, isotopically labeled derivative, or prodrug thereof.

In certain embodiments, a compound of Formula (III-g) is of one of the following formulae:

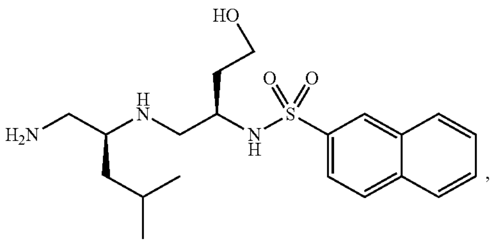

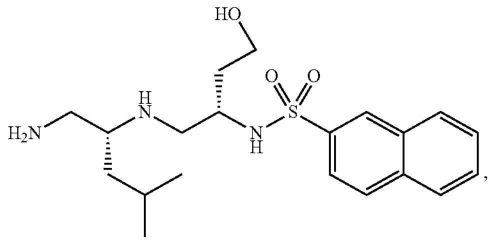

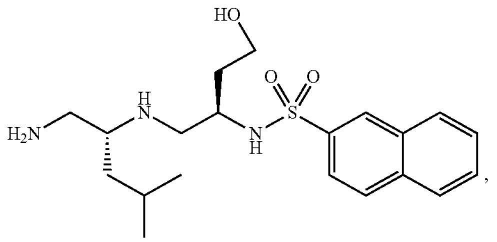

-continued

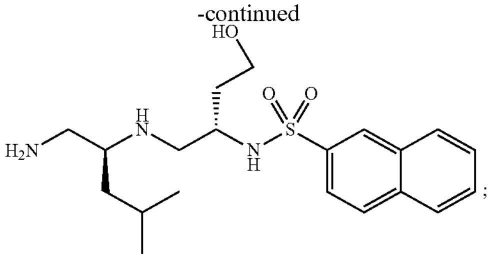;

or a pharmaceutically acceptable salt, hydrate, solvate, polymorph, co-crystal, tautomer, stereoisomer, isotopically labeled derivative, or prodrug thereof.

In certain embodiments, a compound of Formula (III) is of one of the following formulae:

(2470-49)

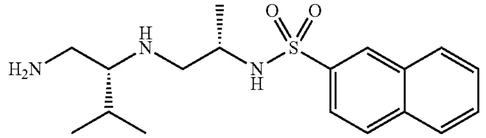

(2470-40)

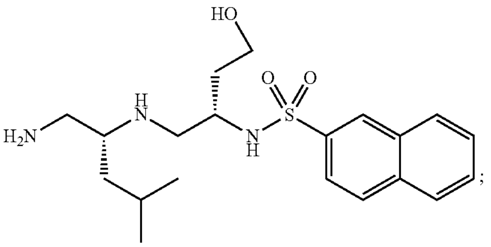;

or a pharmaceutically acceptable salt, hydrate, solvate, polymorph, co-crystal, tautomer, stereoisomer, isotopically labeled derivative, or prodrug thereof.

R Group Definitions

The following definitions apply to all formulae recited herein, including, but not limited to, Formulae (I), (II) and (III).

Groups $R^1$ and $R^2$

As generally defined herein, $R^1$ and $R^2$ are independently hydrogen, optionally substituted $C_{1-6}$ alkyl, optionally substituted carbocyclyl, optionally substituted heterocyclyl, optionally substituted heterocyclylalkyl, or optionally substituted heteroaralyl.

In certain embodiments, $R^1$ is hydrogen. In certain embodiments, $R^1$ is optionally substituted carbocyclyl. In certain embodiments, $R^1$ is optionally substituted heterocyclyl. In certain embodiments, $R^1$ is optionally substituted heterocyclylalkyl. In certain embodiments, $R^1$ is optionally substituted heteroaralkyl. In certain embodiments, $R^1$ is optionally substituted $C_{1-6}$ alkyl. In certain embodiments, $R^1$ is substituted $C_{1-6}$ alkyl. In certain embodiments, $R^1$ is unsubstituted $C_{1-6}$ alkyl. In certain embodiments, $R^1$ is selected from the group consisting of methyl, ethyl, propyl, butyl, iso-propyl, iso-butyl, sec-butyl, and tert-butyl. In certain embodiments, $R^1$ is optionally substituted $C_{1-3}$alkyl. In certain embodiments, $R^1$ is substituted $C_{1-3}$ alkyl. In certain embodiments, $R^1$ is unsubstituted $C_{1-3}$ alkyl. In certain embodiments, $R^1$ is selected from the group consisting of methyl, ethyl, propyl, and iso-propyl. In certain embodiments, $R^1$ is methyl. In certain embodiments, $R^1$ is iso-propyl. In certain embodiments, $R^1$ is iso-butyl.

In certain embodiments, $R^1$ is $C_{1-6}$ alkyl substituted with a nitrogen-, oxygen-, or sulfur-containing moiety. In certain embodiments, $R^1$ is selected from the group consisting of $—CH_2(CH_2)_{0-4}OR^O$, $—CH(OR^O)CH_3$, $—(CH_2)_{1-4}CH(OR^O)CH_3$, $—CH_2(CH_2)_{0-4}SR^S$, and $—CH_2(CH_2)_{0-4}N(R^N)_2$, wherein $R^O$ is hydrogen, optionally substituted $C_{1-6}$ alkyl, optionally substituted acyl, or an oxygen protecting group; $R^S$ is hydrogen, optionally substituted $C_{1-6}$ alkyl, optionally substituted acyl, or a sulfur protecting group; and $R^N$ is optionally substituted $C_{1-6}$ alkyl, optionally substituted acyl, or a nitrogen protecting group; or optionally two $R^N$ are joined together with the intervening atoms to form optionally substituted heterocyclyl or optionally substituted aryl. In certain embodiments, $R^1$ is $—CH_2(CH_2)_{1-4}OR^O$, and $R^O$ is optionally substituted $C_{1-6}$alkyl. In certain embodiments, $R^1$ is $—CH_2(CH_2)_{1-4}OR^O$, and $R^O$ is hydrogen. In certain embodiments, $R^1$ is selected from the group consisting of $—CH_2CH_2OH$, $—CH_2CH_2CH_2OH$, $—CH_2CH_2CH_2CH_2OH$, or $—CH_2CH_2CH_2CH_2OH$. In certain embodiments, $R^1$ is $—CH_2CH_2OH$.

In certain embodiments, $R^1$ is selected from the group consisting of $—CH_2OH$, $—CH_2CH_2OH$, $—CH(OH)CH_3$, $—CH_2CH(OH)CH_3$, $—CH_2SH$, $—CH_2CH_2SCH_3$, $—CH_2NH_2$, $—CH_2CH_2NH_2$, $—CH_2CH_2CH_2NH_2$, $—CH_2CH_2CH_2CH_2NH_2$, and $—CH_2CH_2CH_2CH_2NH_2$.

In certain embodiments, $R^1$ is optionally substituted heterocyclyl. In certain embodiments, $R^1$ is optionally substituted $C_{3-6}$ heterocyclyl. In certain embodiments, $R^1$ is optionally substituted five-membered heterocyclyl. In certain embodiments, $R^1$ is optionally substituted pyrrolidine. In certain embodiments, $R^1$ is of the formula:

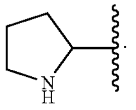

In certain embodiments, $R^1$ is of the formula:

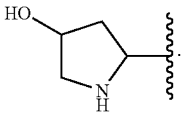

In certain embodiments, $R^1$ is optionally substituted heterocyclylalkyl. In certain embodiments, $R^1$ is optionally substituted $—C_{1-6}$ alkyl-heterocyclyl. In certain embodiments, $R^1$ is optionally substituted $—CH_2$-heterocyclyl. In certain embodiments, $R^1$ is optionally substituted $—CH_2—C_{3-6}$ heterocyclyl. In certain embodiments, $R^1$ is optionally substituted $—CH_2—C_5$ heterocyclyl. In certain embodiments, $R^1$ is optionally substituted $—CH_2—$ pyrrolidine. In certain embodiments, $R^1$ is of the formula:

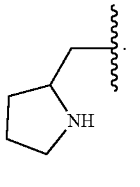 [SMILES: *CC1CCCN1]

In certain embodiments, $R^1$ is optionally substituted heteroaralkyl. In certain embodiments, $R^1$ is optionally substituted —$C_{1-6}$ alkyl-heterocyclyl. In certain embodiments, $R^1$ is optionally substituted —$CH_2$— heterocyclyl. In certain embodiments, $R^1$ is optionally substituted —$CH_2$—$C_{3-6}$ heterocyclyl. In certain embodiments, $R^1$ is optionally substituted —$CH_2$—$C_5$ heterocyclyl. In certain embodiments, $R^1$ is of the formula:

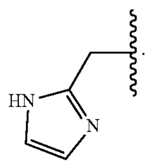 [SMILES: *Cc1ncc[nH]1]

In certain embodiments, $R^1$ is optionally substituted —$CH_2$—$C_{7-10}$ heterocyclyl. In certain embodiments, $R^1$ is of the formula:

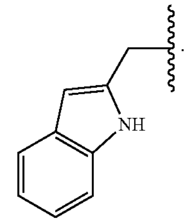

In certain embodiments, $R^1$ is any amino acid side chain, provided that the amino acid is not phenylalanine or tyrosine.

In certain embodiments, $R^2$ is hydrogen. In certain embodiments, $R^2$ is optionally substituted carbocyclyl. In certain embodiments, $R^2$ is optionally substituted heterocyclyl. In certain embodiments, $R^2$ is optionally substituted heterocyclylalkyl. In certain embodiments, $R^2$ is optionally substituted heteroaralkyl. In certain embodiments, $R^2$ is optionally substituted $C_{1-6}$ alkyl. In certain embodiments, $R^2$ is substituted $C_{1-6}$ alkyl. In certain embodiments, $R^2$ is unsubstituted $C_{1-6}$ alkyl. In certain embodiments, $R^2$ is selected from the group consisting of methyl, ethyl, propyl, butyl, iso-propyl, iso-butyl, sec-butyl, and tert-butyl. In certain embodiments, $R^2$ is optionally substituted $C_{1-3}$alkyl. In certain embodiments, $R^2$ is substituted $C_{1-3}$ alkyl. In certain embodiments, $R^2$ is unsubstituted $C_{1-3}$ alkyl. In certain embodiments, $R^2$ is selected from the group consisting of methyl, ethyl, propyl, and iso-propyl. In certain embodiments, $R^2$ is methyl. In certain embodiments, $R^2$ is iso-propyl. In certain embodiments, $R^2$ is iso-butyl.

In certain embodiments, $R^2$ is $C_{1-6}$alkyl substituted with a nitrogen-, oxygen-, or sulfur-containing moiety. In certain embodiments, $R^2$ is selected from the group consisting of —$CH_2(CH_2)_{0-4}OR^O$, —$CH(OR^O)CH_3$, —$(CH_2)_{1-4}CH(OR^O)CH_3$, —$CH_2(CH_2)_{0-4}SR^S$, —$CH_2(CH_2)_{0-4}N(R^N)_2$, wherein $R^O$ is hydrogen, optionally substituted $C_{1-6}$alkyl, optionally substituted acyl, or an oxygen protecting group; $R^S$ is hydrogen, optionally substituted $C_{1-6}$ alkyl, optionally substituted acyl, or a sulfur protecting group; and $R^N$ is optionally substituted $C_{1-6}$alkyl, optionally substituted acyl, or a nitrogen protecting group; or optionally two $R^N$ are joined together with the intervening atoms to form optionally substituted heterocyclyl or optionally substituted aryl. In certain embodiments, $R^2$ is —$CH_2(CH_2)_{1-4}OR^O$, and $R^O$ is optionally substituted $C_{1-6}$alkyl. In certain embodiments, $R^2$ is —$CH_2(CH_2)_{1-4}OR^O$, and $R^O$ is hydrogen. In certain embodiments, $R^2$ is selected from the group consisting of —$CH_2CH_2OH$, —$CH_2CH_2CH_2OH$, —$CH_2CH_2CH_2CH_2OH$, or —$CH_2CH_2CH_2CH_2OH$. In certain embodiments, $R^2$ is —$CH_2CH_2OH$.

In certain embodiments, $R^2$ is selected from the group consisting of —$CH_2OH$, —$CH_2CH_2OH$, —$CH(OH)CH_3$, —$CH_2CH(OH)CH_3$, —$CH_2SH$, —$CH_2CH_2SCH_3$, —$CH_2NH_2$, —$CH_2CH_2NH_2$, —$CH_2CH_2CH_2NH_2$, —$CH_2CH_2CH_2CH_2NH_2$, and —$CH_2CH_2CH_2CH_2NH_2$.

In certain embodiments, $R^2$ is optionally substituted heterocyclyl. In certain embodiments, $R^2$ is optionally substituted $C_{3-6}$heterocyclyl. In certain embodiments, $R^2$ is optionally substituted five-membered heterocyclyl. In certain embodiments, $R^2$ is optionally substituted pyrrolidine. In certain embodiments, $R^2$ is of the formula:

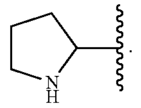 [SMILES: *C1CCCN1]

In certain embodiments, $R^2$ is of the formula:

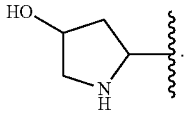

In certain embodiments, $R^2$ is optionally substituted heterocyclylalkyl. In certain embodiments, $R^2$ is optionally substituted —$C_{1-6}$alkyl-heterocyclyl. In certain embodiments, $R^2$ is optionally substituted —$CH_2$-heterocyclyl. In certain embodiments, $R^2$ is optionally substituted —$CH_2$—$C_{3-6}$ heterocyclyl. In certain embodiments, $R^2$ is optionally substituted —$CH_2$—$C_5$ heterocyclyl. In certain embodiments, $R^2$ is optionally substituted —$CH_2$-pyrrolidine. In certain embodiments, $R^2$ is of the formula:

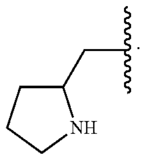 [SMILES: *CC1CCCN1]

In certain embodiments, $R^2$ is optionally substituted heteroaralkyl. In certain embodiments, $R^2$ is optionally substituted —$C_{1-6}$ alkyl-heterocyclyl. In certain embodiments, $R^2$ is optionally substituted —$CH_2$-heterocyclyl. In certain embodiments, $R^2$ is optionally substituted —$CH_2$—$C_{3-6}$ heterocyclyl. In certain embodiments, $R^2$ is optionally substituted —$CH_2$—$C_5$heterocyclyl. In certain embodiments, $R^2$ is of the formula:

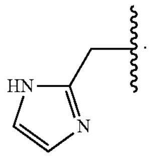

In certain embodiments, $R^2$ is optionally substituted —$CH_2$—$C_{7-10}$ heterocyclyl. In certain embodiments, $R^2$ is of the formula:

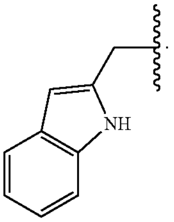 [SMILES: *Cc1cc2ccccc2[nH]1]

In certain embodiments, $R^2$ is any amino acid side chain, provided that the amino acid is not phenylalanine or tyrosine.

In certain embodiments, $R^1$ is optionally substituted $C_{1-6}$ alkyl; and $R^2$ is optionally substituted $C_{1-6}$ alkyl. In certain embodiments, $R^1$ is unsubstituted $C_{1-6}$ alkyl; and $R^2$ is unsubstituted $C_{1-6}$ alkyl. In certain embodiments, $R^1$ is optionally substituted $C_{1-3}$ alkyl; and $R^2$ is optionally substituted $C_{1-3}$ alkyl. In certain embodiments, $R^1$ is unsubstituted $C_{1-3}$alkyl; and $R^2$ is unsubstituted $C_{1-3}$ alkyl. In certain embodiments, both $R^1$ and $R^2$ are independently selected from the group consisting of methyl, ethyl, propyl, and iso-propyl. In certain embodiments, $R^1$ is methyl; and $R^2$ is iso-propyl. In certain embodiments, $R^1$ is ethyl; and $R^2$ is iso-propyl. In certain embodiments, $R^1$ is n-propyl; and $R^2$ is iso-propyl. In certain embodiments, $R^2$ is methyl; and $R^1$ is iso-propyl. In certain embodiments, $R^2$ is ethyl; and $R^1$ is iso-propyl. In certain embodiments, $R^2$ is n-propyl; and $R^1$ is iso-propyl. In certain embodiments, both $R^1$ and $R^2$ are methyl. In certain embodiments, both $R^1$ and $R^2$ are ethyl.

In certain embodiments, both $R^1$ and $R^2$ are n-propyl. In certain embodiments, both $R^1$ and $R^2$ are iso-propyl.

In certain embodiments, $R^1$ is substituted $C_{1-6}$ alkyl; and $R^2$ is unsubstituted $C_{1-6}$ alkyl. In certain embodiments, $R^1$ is —$CH_2(CH_2)_{0-4}OR^O$, wherein $R^O$ is hydrogen, optionally substituted $C_{1-6}$ alkyl, optionally substituted acyl, or an oxygen protecting group; and $R^2$ is unsubstituted $C_{1-6}$alkyl. In certain embodiments, $R^1$ is —$CH_2(CH_2)_{0-4}OH$; and $R^2$ is unsubstituted $C_{1-6}$ alkyl. In certain embodiments, $R^1$ is selected from the group consisting of —$CH_2OH$, —$CH_2CH_2OH$, —$CH_2CH_2CH_2OH$, —$CH_2CH_2CH_2CH_2OH$, or —$CH_2CH_2CH_2CH_2OH$; and $R^2$ is selected from the group consisting of methyl, ethyl, propyl, butyl, iso-propyl, iso-butyl, and sec-butyl. In certain embodiments, $R^1$ is —$CH_2CH_2OH$; and $R^2$ is iso-butyl.

Group $R^3$

As generally defined herein, $R^3$ is optionally substituted alkyl, optionally substituted aryl, optionally substituted heteroaryl, optionally substituted carbocyclyl, or optionally substituted heterocyclyl.

In certain embodiments, $R^3$ is optionally substituted alkyl. In certain embodiments, $R^3$ is optionally substituted $C_{1-6}$ alkyl. In certain embodiments, $R^3$ is optionally substituted $C_{1-3}$ alkyl.

In certain embodiments, $R^3$ is optionally substituted heteroaryl. In certain embodiments, $R^3$ is optionally substituted five-membered heteroaryl. In certain embodiments, $R^3$ is optionally substituted six-membered heteroaryl. In certain embodiments, $R^3$ is optionally substituted five- to seven-membered heteroaryl. In certain embodiments, $R^3$ is optionally substituted nine-membered heteroaryl. In certain embodiments, $R^3$ is optionally substituted ten-membered heteroaryl.

In certain embodiments, $R^3$ is optionally substituted carbocyclyl. In certain embodiments, $R^3$ is optionally substituted $C_3$carbocyclyl. In certain embodiments, $R^3$ is optionally substituted $C_4$carbocyclyl. In certain embodiments, $R^3$ is optionally substituted $C_5$carbocyclyl. In certain embodiments, $R^3$ is optionally substituted $C_6$carbocyclyl. In certain embodiments, $R^3$ is optionally substituted $C_7$ carbocyclyl. In certain embodiments, $R^3$ is optionally substituted $C_8$ carbocyclyl. In certain embodiments, $R^3$ is optionally substituted $C_9$ carbocyclyl. In certain embodiments, $R^3$ is optionally substituted $C_{10}$ carbocyclyl.

In certain embodiments, $R^3$ is optionally substituted heterocyclyl. In certain embodiments, $R^3$ is optionally substituted three-membered heterocyclyl. In certain embodiments, $R^3$ is optionally substituted four-membered heterocyclyl. In certain embodiments, $R^3$ is optionally substituted five-membered heterocyclyl. In certain embodiments, $R^3$ is optionally substituted six-membered heterocyclyl. In certain embodiments, $R^3$ is optionally substituted seven-membered heterocyclyl.

In certain embodiments, $R^3$ is optionally substituted aryl. In certain embodiments, $R^3$ is optionally substituted $C_{6-10}$ aryl. In certain embodiments, $R^3$ is optionally substituted phenyl. In certain embodiments, $R^3$ is unsubstituted phenyl. In certain embodiments, $R^3$ is substituted phenyl. In certain embodiments, $R^3$ is phenyl substituted with 0, 1, 2, 3, 4, or 5 instances of $R^4$, wherein $R^4$ is as defined herein. In certain embodiments, $R^3$ is of the formula:

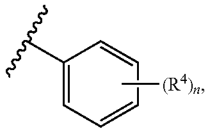

wherein $R^4$ is as defined herein; and n is 0, 1, 2, 3, 4, or 5.

In certain embodiments, $R^3$ is of one of the following formulae:

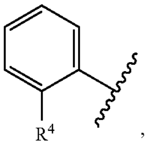
,
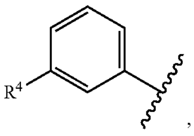
,
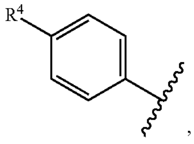
,
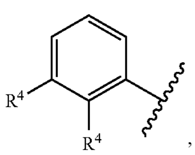
,
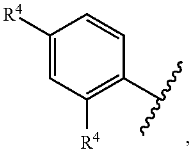
,
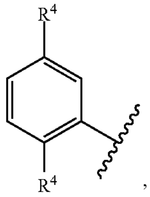
, -continued

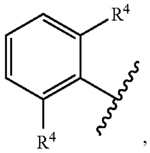, 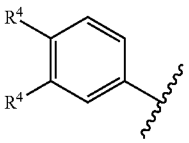, 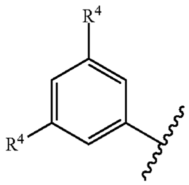,

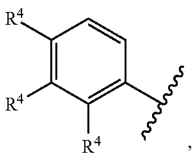, 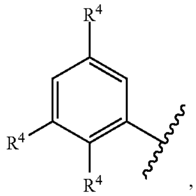,

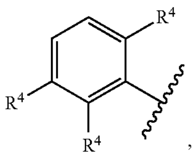, 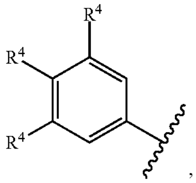,

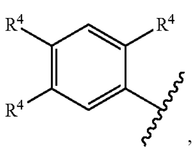, 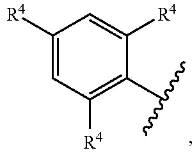,

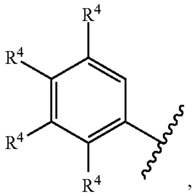, 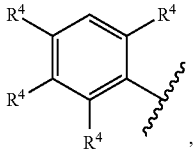,

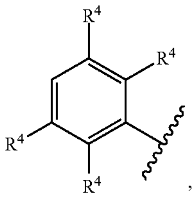, or 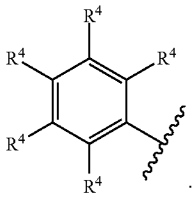.

In certain embodiments, n is 1, and $R^3$ is of the following formula:

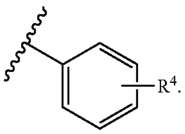

In certain embodiments, n is 1; and $R^3$ is of the formula:

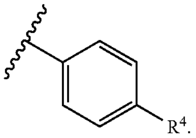

In certain embodiments, n is 1; and $R^3$ is of the formula:

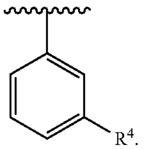

In certain embodiments, n is 1; and $R^3$ is of the formula:

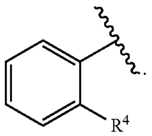

In certain embodiments, $R^3$ is of the following formula:

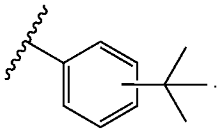

In certain embodiments, $R^3$ is of the formula:

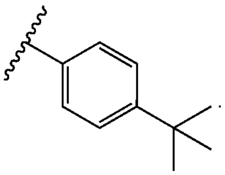 [SMILES: *c1ccc(C(C)(C)C)cc1]

In certain embodiments, $R^3$ is of the formula:

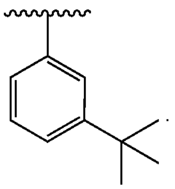 [SMILES: *c1cccc(C(C)(C)C)c1]

In certain embodiments, $R^3$ is of the formula:

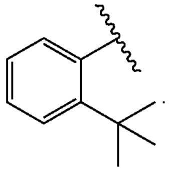 [SMILES: *c1ccccc1C(C)(C)C]

In certain embodiments, $R^3$ is of one of the following formulae:

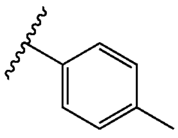
,
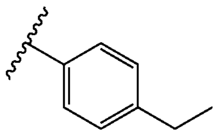
,
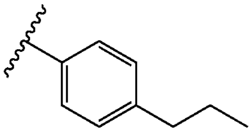
,
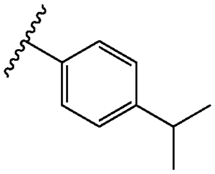
,
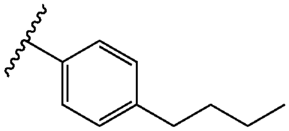
,
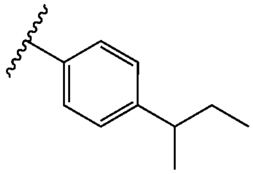
, or
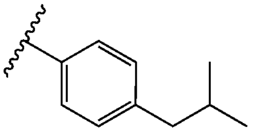
.

In certain embodiments, $R^3$ is of the following formula:

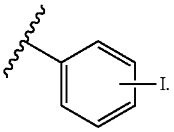

In certain embodiments, $R^3$ is of the formula:

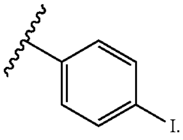 [SMILES: *c1ccc(I)cc1]

In certain embodiments, $R^3$ is of the formula:

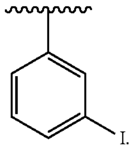 [SMILES: *c1cccc(I)c1]

In certain embodiments, $R^3$ is of the formula:

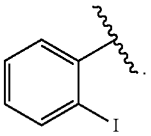 [SMILES: *c1ccccc1I]

In certain embodiments, $R^3$ is of one of the following formulae:

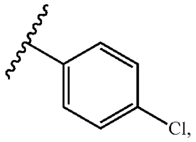
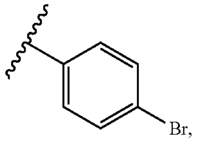
or
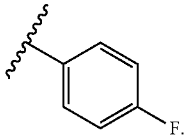

In certain embodiments, $R^3$ is optionally substituted naphthyl. In certain embodiments, $R^3$ is substituted naphthyl. In certain embodiments, $R^3$ is unsubstituted naphthyl. In certain embodiments, $R^3$ is substituted with 0, 1, 2, 3, 4, 5, 6, or 7, instances of $R^4$, wherein $R^4$ is as defined herein. In certain embodiments, $R^3$ is of one of the following formulae:

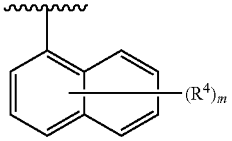
or
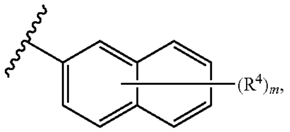

wherein $R^4$ is as defined herein and m is 0, 1, 2, 3, 4, 5, 6, or 7. In certain embodiments, m is 0 and $R^3$ is of one of the following formulae:

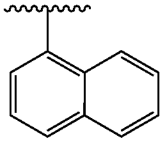
or
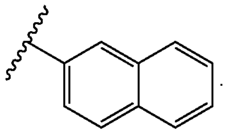 [SMILES: *c1ccc2ccccc2c1 ; "."]
.

In certain embodiments, $R^3$ is of the following formula:

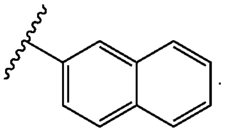
.

As generally defined herein, n is 0, 1, 2, 3, 4, or 5. In certain embodiments, n is 0. In certain embodiments, n is 1. In certain embodiments, n is 2. In certain embodiments, n is 3. In certain embodiments, n is 4. In certain embodiments, n is 5.

As generally defined herein, m is 0, 1, 2, 3, 4, 5, 6, or 7. In certain embodiments, m is 0. In certain embodiments, m is 1. In certain embodiments, m is 2. In certain embodiments, m is 3. In certain embodiments, m is 4. In certain embodiments, m is 5. In certain embodiments, m is 6. In certain embodiments, m is 7.

Groups $R^{N1}$, $R^{N2}$, $R^{N3}$, and $R^{N4}$

As generally defined herein, $R^{N1}$, $R^{N2}$, $R^{N3}$, and $R^{N4}$ are each independently hydrogen, optionally substituted alkyl, optionally substituted aryl, optionally substituted acyl, or a nitrogen protecting group; or optionally $R^{N3}$ and $R^{N4}$ are joined together with the intervening atoms to form optionally substituted heterocyclyl or optionally substituted heteroaryl. In certain embodiments, $R^{N3}$ and $R^{N4}$ are taken together with the intervening atoms to form optionally substituted heterocyclyl. In certain embodiments, $R^{N3}$ and $R^{N4}$ are taken together with the intervening atoms to form optionally substituted heteroaryl.

As generally defined herein, $R^{N1}$ is hydrogen, optionally substituted alkyl, optionally substituted aryl, optionally substituted acyl, or a nitrogen protecting group. In certain embodiments, $R^{N1}$ is optionally substituted alkyl. In certain embodiments, $R^{N1}$ is optionally substituted $C_{1-6}$alkyl. In certain embodiments, $R^{N1}$ is substituted $C_{1-6}$alkyl. In certain embodiments, $R^{N1}$ is unsubstituted $C_{1-6}$alkyl. In certain embodiments, $R^{N1}$ is optionally substituted $C_{1-3}$ alkyl. In certain embodiments, $R^{N1}$ is substituted $C_{1-3}$ alkyl. In certain embodiments, $R^{N1}$ is unsubstituted $C_{1-3}$ alkyl. In certain embodiments, $R^{N1}$ is selected from the group consisting of methyl, ethyl, propyl, iso-propyl, butyl, iso-butyl, sec-butyl, and tert-butyl. In certain embodiment, $R^{N1}$ is methyl. In certain embodiments, $R^{N1}$ is ethyl. In certain embodiments, $R^{N1}$ is optionally substituted aryl. In certain embodiments, $R^{N1}$ is substituted aryl. In certain embodiments, $R^{N1}$ is unsubstituted aryl. In certain embodiments, $R^{N1}$ is optionally substituted phenyl. In certain embodiments, $R^{N1}$ is substituted phenyl. In certain embodiments, $R^{N1}$ is unsubstituted phenyl. In certain embodiments, $R^{N1}$ is optionally substituted naphthyl. In certain embodiments, $R^{N1}$ is substituted naphthyl. In certain embodiments, $R^{N1}$ is unsubstituted naphthyl. In certain embodiments, $R^{N1}$ is optionally substituted acyl. In certain embodiments, $R^{N1}$ is substituted acyl. In certain embodiments, $R^{N1}$ is unsubstituted acyl. In certain embodiments, $R^{N1}$ is a nitrogen protecting group. In certain embodiments, $R^{N1}$ is hydrogen.

As generally defined herein, $R^{N2}$ is hydrogen, optionally substituted alkyl, optionally substituted aryl, optionally substituted acyl, or a nitrogen protecting group. In certain embodiments, $R^{N2}$ is optionally substituted alkyl. In certain embodiments, $R^{N2}$ is optionally substituted $C_{1-6}$ alkyl. In certain embodiments, $R^{N2}$ is substituted $C_{1-6}$ alkyl. In certain embodiments, $R^{N2}$ is unsubstituted $C_{1-6}$ alkyl. In certain embodiments, $R^{N2}$ is optionally substituted $C_{1-3}$ alkyl. In certain embodiments, $R^{N2}$ is substituted $C_{1-3}$ alkyl. In certain embodiments, $R^{N2}$ is unsubstituted $C_{1-3}$alkyl. In certain embodiments, $R^{N2}$ is selected from the group consisting of methyl, ethyl, propyl, iso-propyl, butyl, iso-butyl, sec-butyl, and tert-butyl. In certain embodiment, $R^{N2}$ is methyl. In certain embodiments, $R^{N2}$ is ethyl. In certain embodiments, $R^{N2}$ is optionally substituted aryl. In certain embodiments, $R^{N2}$ is substituted aryl. In certain embodiments, $R^{N2}$ is unsubstituted aryl. In certain embodiments, $R^{N2}$ is optionally substituted phenyl. In certain embodiments, $R^{N2}$ is substituted phenyl. In certain embodiments, $R^{N2}$ is unsubstituted phenyl. In certain embodiments, $R^{N2}$ is optionally substituted naphthyl. In certain embodiments, $R^{N2}$ is substituted naphthyl. In certain embodiments, $R^{N2}$ is unsubstituted naphthyl. In certain embodiments, $R^{N2}$ is optionally substituted acyl. In certain embodiments, $R^{N2}$ is substituted acyl. In certain embodiments, $R^{N2}$ is unsubstituted acyl. In certain embodiments, $R^{N2}$ is a nitrogen protecting group. In certain embodiments, $R^{N2}$ is hydrogen.

As generally defined herein, $R^{N3}$ is hydrogen, optionally substituted alkyl, optionally substituted aryl, optionally substituted acyl, or a nitrogen protecting group. In certain embodiments, $R^{N3}$ is optionally substituted alkyl. In certain embodiments, $R^{N3}$ is optionally substituted $C_{1-6}$ alkyl. In certain embodiments, $R^{N3}$ is substituted $C_{1-6}$ alkyl. In certain embodiments, $R^{N3}$ is unsubstituted $C_{1-6}$ alkyl. In certain embodiments, $R^{N3}$ is optionally substituted $C_{1-3}$ alkyl. In certain embodiments, $R^{N3}$ is substituted $C_{1-3}$ alkyl. In certain embodiments, $R^{N3}$ is unsubstituted $C_{1-3}$ alkyl. In certain embodiments, $R^{N3}$ is selected from the group consisting of methyl, ethyl, propyl, iso-propyl, butyl, iso-butyl, sec-butyl, and tert-butyl. In certain embodiment, $R^{N3}$ is methyl. In certain embodiments, $R^{N3}$ is ethyl. In certain embodiments, $R^{N3}$ is optionally substituted aryl. In certain embodiments, $R^{N3}$ is substituted aryl. In certain embodiments, $R^{N3}$ is unsubstituted aryl. In certain embodiments, $R^{N3}$ is optionally substituted phenyl. In certain embodiments, $R^{N3}$ is substituted phenyl. In certain embodiments, $R^{N3}$ is unsubstituted phenyl. In certain embodiments, $R^{N3}$ is optionally substituted naphthyl. In certain embodiments, $R^{N3}$ is substituted naphthyl. In certain embodiments, $R^{N3}$ is unsubstituted naphthyl. In certain embodiments, $R^{N3}$ is optionally substituted acyl. In certain embodiments, $R^{N3}$ is substituted acyl. In certain embodiments, $R^{N3}$ is unsubstituted acyl. In certain embodiments, $R^{N3}$ is a nitrogen protecting group. In certain embodiments, $R^{N1}$ is hydrogen.

As generally defined herein, $R^{N4}$ is hydrogen, optionally substituted alkyl, optionally substituted aryl, optionally substituted acyl, or a nitrogen protecting group. In certain embodiments, $R^{N4}$ is optionally substituted alkyl. In certain embodiments, $R^{N4}$ is optionally substituted $C_{1-6}$ alkyl. In certain embodiments, $R^{N4}$ is substituted $C_{1-6}$ alkyl. In certain embodiments, $R^{N4}$ is unsubstituted $C_{1-6}$ alkyl. In certain embodiments, $R^{N4}$ is optionally substituted $C_{1-3}$ alkyl. In certain embodiments, $R^{N4}$ is substituted $C_{1-3}$ alkyl. In certain embodiments, $R^{N4}$ is unsubstituted $C_{1-3}$ alkyl. In certain embodiments, $R^{N4}$ is selected from the group consisting of methyl, ethyl, propyl, iso-propyl, butyl, iso-butyl, sec-butyl, and tert-butyl. In certain embodiment, $R^{N4}$ is methyl. In certain embodiments, $R^{N4}$ is ethyl. In certain embodiments, $R^{N4}$ is optionally substituted aryl. In certain embodiments, $R^{N4}$ is substituted aryl. In certain embodiments, $R^{N4}$ is unsubstituted aryl. In certain embodiments, $R^{N4}$ is optionally substituted phenyl. In certain embodiments, $R^{N4}$ is substituted phenyl. In certain embodiments, $R^{N4}$ is unsubstituted phenyl. In certain embodiments, $R^{N4}$ is optionally substituted naphthyl. In certain embodiments, $R^{N4}$ is substituted naphthyl. In certain embodiments, $R^{N4}$ is unsubstituted naphthyl. In certain embodiments, $R^{N4}$ is optionally substituted acyl. In certain embodiments, $R^{N4}$ is substituted acyl. In certain embodiments, $R^{N4}$ is unsubstituted acyl. In certain embodiments, $R^{N1}$ is an oxygen protecting group. In certain embodiments, $R^{N4}$ is hydrogen.

In certain embodiments, $R^{N1}$, $R^{N2}$, $R^{N3}$, and $R^{N4}$ are all hydrogen.

In certain embodiments, $R^2$ and either $R^{N3}$ and $R^{N4}$ are joined together with the intervening atoms to form optionally substituted heterocyclyl. In certain embodiments, $R^2$ and either $R^{N3}$ and $R^{N4}$ are joined together with the intervening atoms to form optionally substituted pyrrolidine. In certain embodiments, $R^2$ and either $R^{N3}$ and $R^{N4}$ are joined together with the intervening atoms to form unsubstituted pyrrolidine. In certain embodiments, $R^2$ and either $R^{N3}$ and $R^{N4}$ are joined together with the intervening atoms to form optionally substituted azetidine. In certain embodiments, $R^2$ and either $R^{N3}$ and $R^{N4}$ are joined together with the intervening atoms to form unsubstituted azetidine. In certain embodiments, $R^2$ and either $R^{N3}$ and $R^{N4}$ are joined together with the intervening atoms to form optionally substituted piperidine. In certain embodiments, $R^2$ and either $R^{N3}$ and $R^{N4}$ are joined together with the intervening atoms to form unsubstituted piperidine.

In certain embodiments, $R^1$ and $R^{N2}$ are joined together with the intervening atoms to form optionally substituted heterocyclyl. In certain embodiments, $R^1$ and $R^{N2}$ are joined together with the intervening atoms to form optionally substituted pyrrolidine. In certain embodiments, $R^1$ and $R^{N2}$ are joined together with the intervening atoms to form unsubstituted pyrrolidine. In certain embodiments, $R^1$ and $R^{N2}$ are joined together with the intervening atoms to form optionally substituted azetidine. In certain embodiments, $R^1$ and $R^{N2}$ are joined together with the intervening atoms to form unsubstituted azetidine. In certain embodiments, $R^1$ and $R^{N2}$ are joined together with the intervening atoms to form optionally substituted piperidine. In certain embodiments, $R^1$ and $R^{N2}$ are joined together with the intervening atoms to form unsubstituted piperidine.

In certain embodiments, $R^3$ and $R^{N1}$ are joined together with the intervening atoms to form optionally substituted heterocyclyl. In certain embodiments, $R^3$ and $R^{N1}$ are joined together with the intervening atoms to form optionally substituted pyrrolidine. In certain embodiments, $R^3$ and $R^{N1}$ are joined together with the intervening atoms to form unsubstituted pyrrolidine. In certain embodiments, $R^3$ and $R^{N1}$ are joined together with the intervening atoms to form optionally substituted azetidine. In certain embodiments, $R^3$ and $R^{N1}$ are joined together with the intervening atoms to form unsubstituted azetidine. In certain embodiments, $R^3$ and $R^{N1}$ are joined together with the intervening atoms to form optionally substituted piperidine. In certain embodiments, $R^3$ and $R^{N1}$ are joined together with the intervening atoms to form unsubstituted piperidine.

As generally defined herein, p is 0, 1, or 2. In certain embodiments, p is 0. In certain embodiments, p is 1. In certain embodiments, p is 2.

Group $R^4$

As generally defined herein, each instance of $R^4$ is independently hydrogen, halogen, —CN, —$NO_2$, —$N_3$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^{4a}$, $N(R^{4b})_2$, or —$SR^{4c}$. In certain embodiments, at least one instance of $R^4$ is hydrogen. In certain embodiments, at least one instance of $R^4$ is —CN. In certain embodiments, at least one instance of $R^4$ is —$NO_2$. In certain embodiments, at least one instance of $R^4$ is —$N_3$. In certain embodiments, at least one instance of $R^4$ is optionally substituted alkenyl. In certain embodiments, at least one instance of $R^4$ is optionally substituted alkynyl. In certain embodiments, at least one instance of $R^4$ is optionally substituted carbocyclyl. In certain embodiments, at least one instance of $R^4$ is optionally substituted heterocyclyl. In certain embodiments, at least one instance of $R^4$ is optionally substituted aryl. In certain embodiments, at least one instance of $R^4$ is optionally substituted heteroaryl. In certain embodiments, at least one instance of $R^4$ is optionally substituted acyl. In certain embodiments, at least one instance of $R^4$ is —$OR^{4a}$, wherein $R^{4a}$ is as defined herein. In certain embodiments, at least one instance of $R^4$ is —$N(R^{4b})_2$, wherein $R^{4b}$ is as defined herein. In certain embodiments, at least one instance of $R^4$ is —$SR^{4c}$, wherein $R^{4c}$ is as defined herein. In certain embodiments, at least one instance of $R^4$ is optionally substituted alkyl. In certain embodiments, at least one instance of $R^4$ is substituted alkyl. In certain embodiments, at least one instance of $R^4$ is unsubstituted alkyl. In certain embodiments, at least one instance of $R^4$ is optionally substituted $C_{1-6}$alkyl. In certain embodiments, at least one instance of $R^4$ is substituted $C_{1-6}$alkyl. In certain embodiments, at least one instance of $R^4$ is unsubstituted $C_{1-6}$ alkyl. In certain embodiments, at least one instance of $R^4$ is optionally substituted $C_{1-3}$alkyl. In certain embodiments, at least one instance of $R^4$ is substituted $C_{1-3}$alkyl. In certain embodiments, at least one instance of $R^4$ is unsubstituted $C_{1-3}$alkyl. In certain embodiments, at least one instance of $R^4$ is selected from the group consisting of methyl, ethyl, propyl, iso-propyl, butyl, isobutyl, sec-butyl, and tert-butyl. In certain embodiments, at least one instance of $R^4$ is tert-butyl. In certain embodiments, one instance of $R^4$ is tert-butyl. In certain embodiments, at least one instance of $R^4$ is halogen. In certain embodiments, at least one instance of $R^4$ is selected from the group consisting of Cl, Br, F, and I. In certain embodiments, at least one instance of $R^4$ is Cl. In certain embodiments, one instance of $R^4$ is Cl. In certain embodiments, at least one instance of $R^4$ is Br. In certain embodiments, one instance of $R^4$ is Br. In certain embodiments, at least one instance of $R^4$ is F. In certain embodiments, one instance of $R^4$ is F. In certain embodiments, at least one instance of $R^4$ is I. In certain embodiments, one instance of $R^4$ is I.

As generally defined herein, each instance of $R^{4a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or an oxygen protecting group. In certain embodiments, at least one instance of $R^{4a}$ is hydrogen. In certain embodiments, at least one instance of $R^{4a}$ is optionally substituted alkyl. In certain embodiments, at least one instance of $R^{4a}$ is optionally substituted alkenyl. In certain embodiments, at least one instance of $R^{4a}$ is optionally substituted alkynyl. In certain embodiments, at least one instance of $R^{4a}$ is optionally substituted carbocyclyl. In certain embodiments, at least one instance of $R^{4a}$ is optionally substituted heterocyclyl. In certain embodiments, at least one instance of $R^{4a}$ is optionally substituted aryl. In certain embodiments, at least one instance of $R^{4a}$ is optionally substituted heteroaryl. In certain embodiments, at least one instance of $R^{4a}$ is optionally substituted acyl. In certain embodiments, at least one instance of $R^{4a}$ is an oxygen protecting group.

As generally defined herein, each instance of $R^{4b}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group; or optionally two $R^{4b}$ are joined together with the intervening atoms to form optionally substituted heterocyclyl or optionally substituted heteroaryl. In certain embodiments, at least one instance of $R^{4b}$ is hydrogen. In certain embodiments, at least one instance of $R^{4b}$ is optionally substituted alkyl. In certain embodiments, at least one instance of $R^{4b}$ is optionally substituted alkenyl. In certain embodiments, at least one instance of $R^{4b}$ is optionally substituted alkynyl. In certain embodiments, at least one instance of $R^{4b}$ is optionally substituted carbocyclyl. In certain embodiments, at least one instance of $R^{4b}$ is optionally substituted heterocyclyl. In certain embodiments, at least one instance of $R^{4b}$ is optionally substituted aryl. In certain embodiments, at least one instance of $R^{4b}$ is optionally substituted heteroaryl. In certain embodiments, at least one instance of $R^{4b}$ is optionally substituted acyl. In certain embodiments, at least one instance of $R^{4b}$ is a nitrogen protecting group. In certain embodiments, two $R^{4b}$ are joined together with the intervening atoms to form optionally substituted heterocyclyl. In certain embodiments, two $R^{4b}$ are joined together with the intervening atoms to form optionally substituted heteroaryl.

As generally defined herein, each instance of $R^{4c}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a sulfur protecting group. In certain embodiments, at least one instance of $R^{4c}$ is hydrogen. In certain embodiments, at least one instance of $R^{4c}$ is optionally substituted alkyl. In certain embodiments, at least one instance of $R^{4c}$ is optionally substituted alkenyl. In certain embodiments, at least one instance of $R^{4b}$ is optionally substituted alkynyl. In certain embodiments, at least one instance of $R^{4c}$ is optionally substituted carbocyclyl. In certain embodiments, at least one instance of $R^{4c}$ is optionally substituted heterocyclyl. In certain embodiments, at least one instance of $R^{4c}$ is optionally substituted aryl. In certain embodiments, at least one instance of $R^{4c}$ is optionally substituted heteroaryl. In certain embodiments, at least one instance of $R^{4c}$ is optionally substituted acyl. In certain embodiments, at least one instance of $R^{4c}$ is a nitrogen protecting group.

Pharmaceutical Compositions, Kits, and Administration

The present disclosure provides pharmaceutical compositions comprising a compound of Formula (I), or a pharmaceutically acceptable salt thereof, and optionally a pharmaceutically acceptable excipient. In certain embodiments, the pharmaceutical composition described herein comprises a compound of Formula (I), or a pharmaceutically acceptable salt thereof, and a pharmaceutically acceptable excipient.

In certain embodiments, the compound described herein is provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for treating a proliferative disease in a subject in need thereof. In certain embodiments, the effective amount is an amount effective for preventing a proliferative disease in a subject in need thereof. Exemplary proliferative diseases include, but are not limited to, cancer, benign neoplasms, diseases associated with angiogenesis, inflammatory diseases, and autoimmune diseases. In certain embodiments, the effective amount is an amount effective for treating a hematological disease in a subject in need thereof. In certain embodiments, the effective amount is an amount effective for treating cancer (e.g., leukemia, such as AML) in a subject in need thereof. In certain embodiments, the effective amount is an amount effective for preventing the recurrence of a hematological cancer in a subject in need thereof. In certain embodiments, the effective amount is an amount effective for reducing the risk of developing a disease (e.g., proliferative disease, hematological cancer) in a subject in need thereof. In certain embodiments, the effective amount is an amount effective for inducing apoptisis of a cell in a subject or biological sample. In certain embodiments, the effective amount is an amount effective for inhibiting alpha-enolase enzymatic activity in a subject or biological sample.

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, eveninu nrimrnse fish flaxseed, geraniol, gourd, grape seed, hazel nut, hyssop, isopropyl myristate, jojoba, kukui nut, lavandin, lavender, lemon, *litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 μg and 1 μg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive of a compound described herein. In certain embodiments, a dose described herein includes independently between 10 mg and 30 mg, inclusive of a compound described herein. In certain embodiments, a dose described herein includes independently between 30 mg and 100 mg inclusive of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, in reducing the risk to develop a disease in a subject in need thereof), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

Also encompassed by the disclosure are kits (e.g., pharmaceutical packs). The kits provided may comprise a pharmaceutical composition or compound described herein and a container (e.g., a vial ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. In certain embodiments, the kits are useful for treating a disease (e.g., proliferative disease such as cancer) in a subject in need thereof. In certain embodiments, the kits are useful for preventing a disease (e.g., proliferative disease such as cancer) in a subject in need thereof. In certain embodiments, the kits are useful for reducing the risk of developing a disease (e.g., proliferative disease such as cancer) in a subject in need thereof.

In certain embodiments, a kit described herein further includes instructions for using the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease (e.g., proliferative disease such as cancer) in a subject in need thereof. In certain embodiments, the kits and instructions provide for preventing a disease (e.g., proliferative disease such as cancer) in a subject in need thereof. In certain embodiments, the kits and instructions provide for reducing the risk of developing a disease (e.g., proliferative disease such as cancer) in a subject in need thereof. In certain embodiments, the kits and instructions provide for inhibiting the activity (e.g., aberrant activity, such as increased activity) of an alpha-enolase protein in a subject or cell. In certain embodiments, the kits and instructions provide for inducing apoptosis of a cell in a subject or biological sample. A kit described herein may include one or more additional pharmaceutical agents described herein as a separate composition.

Methods of Treatment and Use

The present invention also provides methods of using the compounds of Formula (I), and pharmaceutically acceptable salts, solvates, hydrates, polymorphs, co-crystals, tautomers, stereoisomers, isotopically labeled derivatives, and prodrugs thereof, and pharmaceutical compositions thereof, e.g., for the treatment and/or prevention of diseases or conditions, for the inhibition of alpha-enolase enzymatic activity, and for the induction of apoptosis of cells.

Provided herein are methods of treating and/or preventing a disease or condition in a subject, the methods comprising administering to the subject a compound of Formula (I), or a pharmaceutically acceptable salt, solvate, hydrate, polymorph, co-crystal, tautomer, stereoisomer, isotopically labeled derivative, or prodrug thereof, or a pharmaceutical composition thereof. The compounds provided herein may be used to treat any disease or condition. In certain embodiments, the disease or conditions is a proliferative disease, genetic disease, disease associated with angiogenesis, inflammatory disease, cardiovascular disease, hepatic disease, spleen disease, pulmonary disease, painful condition, hematological disease, neurological disease, psychiatric disorder, autoimmune disease, infectious disease, metabolic disease, gastrointestinal disorder, or endocrine disease.

In certain embodiments, the disease is a proliferative disease. Examples of proliferative diseases include, but are not limited to, benign neoplasms, diseases associated with angiogenesis, inflammatory diseases, and autoimmune diseases. In certain embodiments, the disease is cancer. In certain embodiments, the disease is an FLT3 mutant cancer. In certain embodiments, the disease is a hematological cancer. In certain embodiments, the disease is leukemia. In certain embodiments, the disease is acute lymphocytic leukemia (ALL) (e.g., B-cell ALL, T-cell ALL), acute myeloid leukemia (AML), chronic myeloid leukemia (CML), or chronic lymphocytic leukemia (CLL)). In certain embodiments, the disease is a myelodysplastic syndrome (MDS), myeloproliferative neoplasm (MPN), myelofibrosis (MF), or some combination of a hematological cancer. In certain embodiments, the disease is lymphoma. In certain embodiments, the disease is Hodgkin lymphoma (HL) (e.g., B-cell HL, T-cell HL). In certain embodiments, the disease is non-Hodgkin lymphoma (NHL). Examples of non-Hodgkin lymphoma include, but are not limited to, B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt's lymphoma, lymphoplasmacytic lymphoma (i.e., Waldenstrom's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM). In certain embodiments, the disease is multiple myeloma. In certain embodiments, the disease is AML. In certain embodiments, the disease is FLT3 mutant AML. In certain embodiments, the disease is a disease associated with aberrant alpha-enolase activity. In certain embodiments, the disease is a cancer associated with aberrant alpha-enolase activity. In certain embodiments, the disease is a disease associated with increased alpha-enolase activity. In certain embodiments, the disease is a cancer associated with increased alpha-enolase activity.

The present invention also provides uses of compounds of Formula (I), and pharmaceutically acceptable salts, hydrates, solvates, polymorphs, co-crystals, tautomers, stereoisomers, isotopically labeled derivatives, and prodrugs thereof, and pharmaceutical compositions thereof, for the treatment and/or prevention of diseases described herein.

Additionally, the present invention provides uses of compounds of Formula (I), and pharmaceutically acceptable salts, hydrates, solvates, polymorphs, co-crystals, tautomers, stereoisomers, isotopically labeled derivatives, and prodrugs thereof, and pharmaceutical compositions thereof, for the manufacture of medicaments for the treatment of diseases described herein.

Also provided herein are methods of inducing apoptosis of a cell in a subject or biological sample, the methods comprising administering to the subject or biological sample a compound of Formula (I), or a pharmaceutically acceptable salt, hydrate, solvate, polymorph, co-crystal, tautomer, stereoisomer, isotopically labeled derivative, or prodrug thereof, or a pharmaceutical composition thereof. In certain embodiments, the methods of inducing apoptosis in a cell involve contacting the cell with a compound of Formula (I), or a pharmaceutically acceptable salt, hydrate, solvate, polymorph, co-crystal, tautomer, stereoisomer, isotopically labeled derivative, or prodrug thereof, or a pharmaceutical composition thereof. In certain embodiments, the cell is a cancer cell. In certain embodiments, the cell is a hematopoietic cancer cell (e.g., AML cell). In certain embodiments, the cell is an AML cancer cell.

The present invention also provides uses of compounds of Formula (I), and pharmaceutically acceptable salts, hydrates, solvates, polymorphs, co-crystals, tautomers, stereoisomers, isotopically labeled derivatives, and prodrugs thereof, and pharmaceutical compositions thereof, for the induction of apoptosis in a cell of a subject or biological sample.

Additionally, the present invention provides uses of compounds of Formula (I), and pharmaceutically acceptable salts, hydrates, solvates, polymorphs, co-crystals, tautomers, stereoisomers, isotopically labeled derivatives, and prodrugs thereof, and pharmaceutical compositions thereof, for the manufacture of medicaments for the induction of apoptosis of a cell in a subject or biological sample.

Furthermore, provided herein are methods of modulating the enzymatic activity of (i.e., inhibiting) an alpha-enolase protein, the methods comprising contacting the alpha-enolase with a compound of Formula (I), or a pharmaceutically acceptable salt, hydrate, solvate, polymorph, co-crystal, tautomer, stereoisomer, isotopically labeled derivative, or prodrug thereof, or a pharmaceutical composition thereof. In certain embodiments, the alpha-enolase protein is inhibited in a cell. In certain embodiments, the alpha-enolase protein is inhibited in vitro. In certain embodiments, the alpha-enolase protein is inhibitited in the cell of a subject (e.g., in vivo). As described herein, alpha-enolase overexpression is associated with several cancers and tumors (e.g., hemotological cancers, gliomas, neuroendocrine tumors, neuroblastomas, prostate cancer, pancreatic cancer, cholangiocarcinoma, thyroid cancer, lung cancer, breast cancer, etc.). In untreated cancers (e.g., hemotolocial cancers such as AML), for example, enolase activity is increased due to increased protein expression. Enolase provides ATP as an energy source via its role in glycolysis. Enolase also supports microtubule polymerization and re-organization, which are required for cell cycling. Without wishing to be bound by a particular theory, compounds of the present invention can inhibit alpha-enolase enzymatic activity, thereby reducing ATP for microtubule polymerization and leading to apoptotic cell death.

The present invention also provides uses of compounds of Formula (I), and pharmaceutically acceptable salts, hydrates, solvates, polymorphs, co-crystals, tautomers, stereoisomers, isotopically labeled derivatives, and prodrugs thereof, and pharmaceutical compositions thereof, for the inhibition of enzymatic activity of an alpha-enolase protein.

Additionally, the present invention provides uses of compounds of Formula (I), and pharmaceutically acceptable salts, hydrates, solvates, polymorphs, co-crystals, tautomers, stereoisomers, isotopically labeled derivatives, and prodrugs thereof, and pharmaceutical compositions thereof, for the manufacture of medicaments for the inhibition of an alpha-enolase protein.

In certain embodiments, the methods described herein comprise administering to a subject a therapeutically effective amount compound of Formula (I), or a pharmaceutically acceptable salt, solvate, hydrate, polymorph, co-crystal, tautomer, stereoisomer, isotopically labeled derivative, or prodrug thereof, or a pharmaceutical composition thereof, wherein "therapeutically effective amount" is as defined herein.

In certain embodiments, the methods described herein comprise administering to a subject a prophylactically effective amount compound of Formula (I), or a pharmaceutically acceptable salt, solvate, hydrate, polymorph, co-crystal, tautomer, stereoisomer, isotopically labeled derivative, or prodrug thereof, or a pharmaceutical composition thereof, wherein "prophylactically effective amount" is as defined herein.

A compound or composition provided herein may be administered concurrently with, prior to, or subsequent to, one or more additional therapeutically active agents. In general, each agent will be administered at a dose and/or on a time schedule determined for that agent. It will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually. In certain embodiments, the additional therapeutic agent is an anti-proliferative agent, wherein "anti-proliferative" agent is as defined herein. In certain embodiments, the additional therapeutic agent is an anti-cancer agent, wherein "anti-cancer" agent is as defined herein.

In certain embodiments, the compounds or pharmaceutical compositions described herein can be administered in combination with an anti-cancer therapy including, but not limited to, surgery, radiation therapy, transplantation (e.g., stem cell transplantation, bone marrow transplantation), immunotherapy, and chemotherapy.

In certain embodiments, the subject being treated is a mammal. In certain embodiments, the subject is a human. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent, dog, or non-human primate. In certain embodiments, the subject is a non-human transgenic animal such as a transgenic mouse or transgenic pig.

In certain embodiments, the provided methods comprise contacting a cell with an effective amount of a compound or a pharmaceutical composition as described herein. The cell may be contacted in vitro or in vivo. In certain embodiments, the contacting is in vivo. In certain embodiments, the contacting is in vitro. In certain embodiments, the cell is a cancer cell. In certain embodiments, the cell is a leukemia cell. In certain embodiments, the cell is an acute myeloid leukemia cell (AML cell). In certain embodiments, the cell is a cancer stem cell such as a leukemia stem cell.

In certain embodiments, the methods described herein include contacting a biological sample with an effective amount of a compound of Formula (I), or a pharmaceutically acceptable salt, solvate, hydrate, polymorph, co-crystal, tautomer, stereoisomer, isotopically labeled derivative, or prodrug thereof, or a pharmaceutical composition thereof. In certain embodiments, the biological sample is contacted in vitro. In certain embodiments, the biological sample is obtained from a subject.

EXAMPLES

These and other aspects of the present invention will be further appreciated upon consideration of the following Examples, which are intended to illustrate certain particular embodiments of the invention but are not intended to limit its scope, as defined by the claims.

Synthesis of Compounds

General Synthesis

Compounds of Formula (I) were prepared as shown in Scheme 1. The mBHA (4-methylbenzhydrylamine) resin-bound Boc-protected dipeptide 1 was made using standard Boc (tert-butyloxycarbonyl) chemistry. Reagents and conditions for Scheme 1 are as follows: (a) 55% TFA/DCM (trifluoroacetic acid/dichloromethane), 30 min; 3×5% DIEA (N,N-diisopropylethylamine); (b) Sulfonyl chloride (e.g., Cl—$SO_2R^3$) (8 equiv 0.1M anhydrous DCM), DIEA (10 equiv), room temperature, overnight; (c) $BH_3$-THF (borane-tetrahydrofuran), 65° C., 100 hours; (d) piperidine, 65° C., 24 hours; (e) HF (hydrofluoric acid), 0° C., 7 hours. In all cases the final products were extracted from their HF vessels with 95% acetic acid and then underwent three successive rounds of freezing, lyophilizing, and resuspending with 50% acetonitrile/water.

Scheme 1

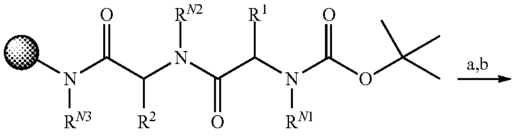

1

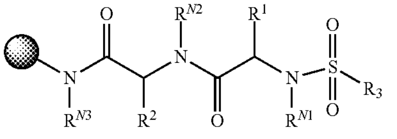

2

-continued

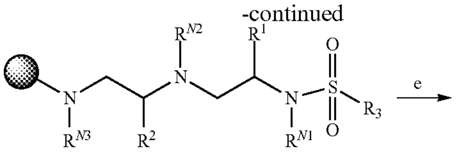

3

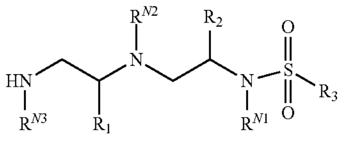

4

 = mHBA resin

Purification and Characterization

Instrumentation

All purification were carried out using a Shimadzu Semi-preparative HPLC (high performance liquid chromatography). The HPLC system consisting of LC-6AD binary pumps, a DGU-20A 3R degassing unit, a CBM-20A communication bus module, a SIL-10AP auto sampler, and a FRC-10A fraction collector. All chromatographic peak detections were performed by using a SPD-20A diode array detector set to detect 214 nm absorbance. All chromatographic separations were performed using a Phenomenex Luna C18 preparative column (5 m, 150×21.20 mm i.d.). The inlet of the column was protected by a Phenomenex C18 Prep security guard cartridge (15×21.2 mm i.d.).

Chemicals and Reagents

All samples were reconstituted in 2000/3000 uL of a 50/50 mixture of HPLC grade or higher acetonitrile/water mixture obtained through Sigma Aldrich. The samples were then filtered through a Spartan 30, 0.45 μm syringe filter before injecting onto the HPLC for separation. The mobile phases consisted of deionized water and HPLC grade acetonitrile with 0.1% LCMS (liquid chromatography-mass spectrometry) grade formic acid obtained from Sigma Aldrich and Fisher Scientific.

HPLC Conditions

The initial setting for the HPLC was 95% water. The gradient was linearly increased to 20% acetonitrile (v/v) over 6 minutes. The gradient was again linearly increased to 60% acetonitrile (v/v) over 39 minutes. The gradient was then linearly increased to 95% acetonitrile (v/v) over 3 minutes and then held for an additional 4 minutes. Finally the gradient was linearly decreased to 5% acetonitrile (v/v) over 1 minute and held until stop. The total run time was equal to 58 minutes. The total flow rate used was 12 mL per minute and peak divide time was set at 0.75 minutes. A slope of 1,000,000uV/sec was set for this unit along with a level of 1,004,500uV, a slope override was also set for 5,510uV. Sample volume injected were based upon crude material yields with either 2000 uL or 3000 uL being injected 1×.

LCMS Analysis

Samples analyzed on Shimadzu Prominence liquid chromatograph (Solvent A: water with 0.1% formic acid; Solvent B: acetonitrile with 0.1% formic acid), Shimadzu Prominence UV (ultraviolet light) Detector (wavelength 214 and 254 nm) and Shimadzu LCMS-2010 (positive mode scanning 175-1000 m/z). Samples are run in reverse phase mode with a flow rate of 0.5 mL/min and a gradient of 5-95% over 6 minutes on a Phenomenex Luna C18 5μ 100 A 50×4.60 mm column.

Exemplary compound 2470-15 was made utilizing the general procedure outlined in Scheme 1. $R^2$ was incorporated from Boc-Val; $R^1$ from Boc-Ala; and $R^3$ from 4-tert-butylbenzene-1-sulfonyl chloride. LCMS Retention Time at 3.74 minutes found $[M+H]^+$ 356.

Exemplary compound 2470-23 was made utilizing the general procedure outlined in Scheme 1. $R^2$ was incorporated from Boc-Val; $R^1$ from Boc-Val; and $R^3$ from 4-iodobenzene-1-sulfonyl chloride. LCMS Retention Time at 3.71 minutes found $[M+H]^+$454.

Exemplary compound 2470-40 was made utilizing the general procedure outlined in Scheme 1. $R^2$ was incorporated from Boc-D-leu; $R^1$ from Boc-Asp(OBzl)-OH; and $R^3$ from naphthalene-2-sulfonyl chloride. LCMS Retention Time at 3.30 minutes found $[M+H]^+$ 394.

Exemplary compound 2470-49 was made utilizing the general procedure outlined in Scheme 1. $R^2$ was incorporated from Boc-D-val; $R^1$ from Boc-Ala; and $R^3$ from naphthalene-2-sulfonyl chloride. LCMS Retention Time at 3.32 minutes found $[M+H]^+$ 350.

Exemplary compound 2470-51 was made utilizing the general procedure outlined in Scheme 1. $R^2$ was incorporated from Boc-D-val; $R^1$ from Boc-Ala; and $R^3$ from 4-tert-butylbenzene-1-sulfonyl chloride. LCMS Retention Time at 3.67 minutes found $[M+H]^+$ 356.

In Vitro and In Vivo Studies

Figure 2:
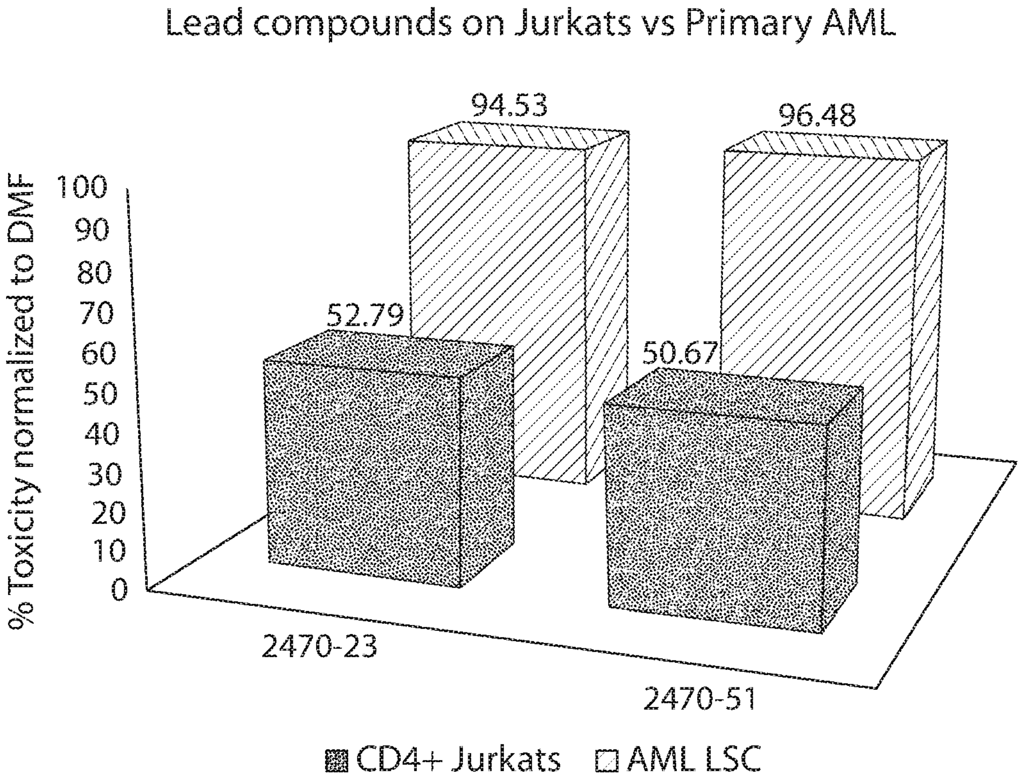
FIG. 2. Comparison of average AML-LSC toxicity vs. Jurkat toxicity. The 2470-23 and 2470-51 single-dose treatments were compared on lymphoid (CD4+ Jurkat) versus myeloid (AML LSC) leukemias to demonstrate the specificity of these compounds for AML.
Figure 3:
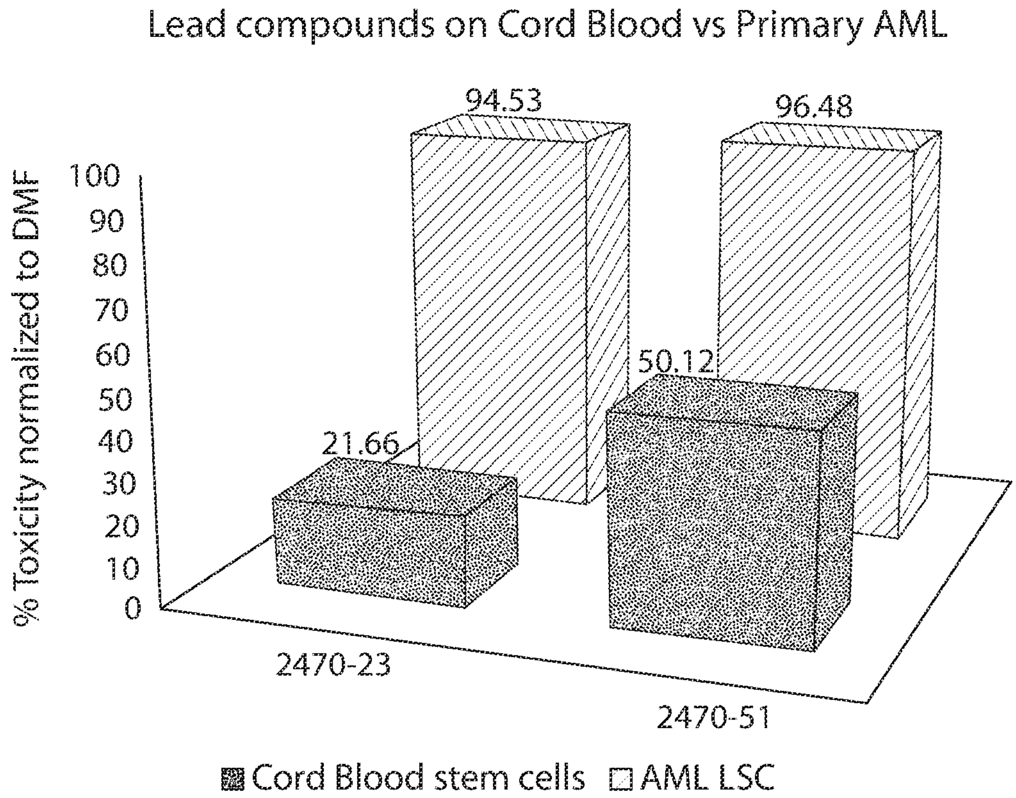
FIG. 3. Comparison of average AML-LSC toxicity vs. cord blood stem cell toxicity. The single-dose treatments of 2470-23 and 2470-51 on normal healthy blood stem cells (sourced from fresh umbilical cord blood) and AML LSC were compared. The compounds do not deplete healthy stem cells while they do deplete the leukemia stem cells. These results indicate selectivity for diseased cells and suggest sparing of normal cells.
Figure 4:
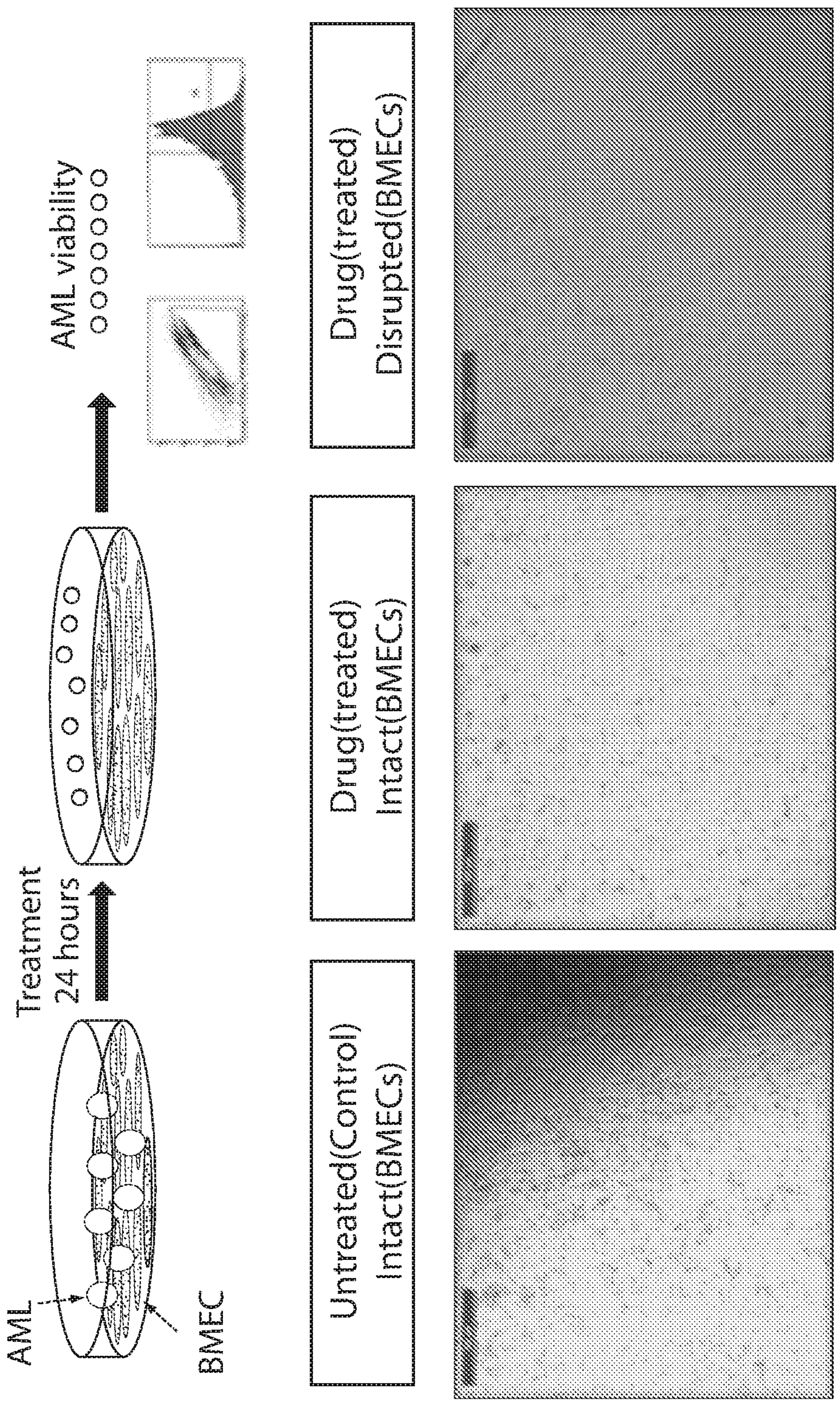
FIG. 4. Schematic of high throughput screening assay. AML cells are cultured on bone marrow derived endothelial cells. After 24 hours of exposure to compound treatment, the AML cells and endothelial cells are analyzed for viability using flow cytometry for 7-AAD and annexin. The phase contrast micrographs in the bottom portion of this figure are representative of untreated control and drug treated conditions. In the control situation, spindle shaped endothelial cells appear under the round shaped AML cells. In the drug treated conditions, some compounds disrupt the spindle shaped endothelial cells and lead to their detachment and death. While other compounds leave the endothelial layer intact but cause AML cells to appear picnotic due to apoptotic death, compounds of the present invention caused AML cell death while leaving the endothelial cell layer intact and viable. This is optimal because of the high toxicity to the malignant cells and low toxicity to stromal cells. Stromal cell viability represents safety.
Figure 5A:
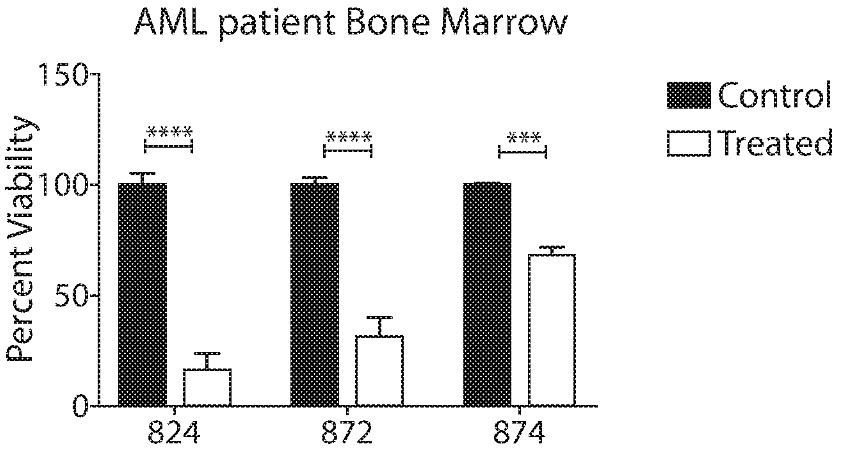
FIG. 5A. Primary human AML specimens (824, 872, 874) treated with 2470-51 for 24 hours at 50 ng/mL significantly reduced AML cell viability compared to vehicle-treated controls (* $P<0.05$).
Figure 5B:
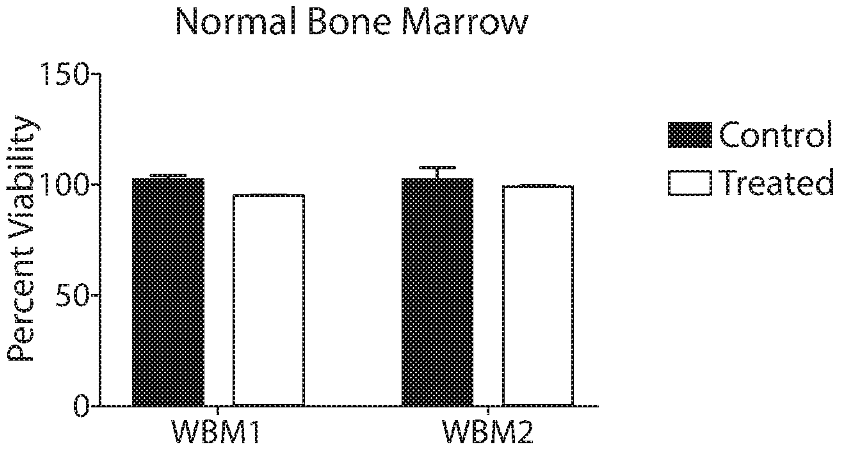
FIG. 5B. Compound 2470-51 did not reduce cell viability of bone marrow cells from healthy adults compared to vehicle control.
Figure 5C:
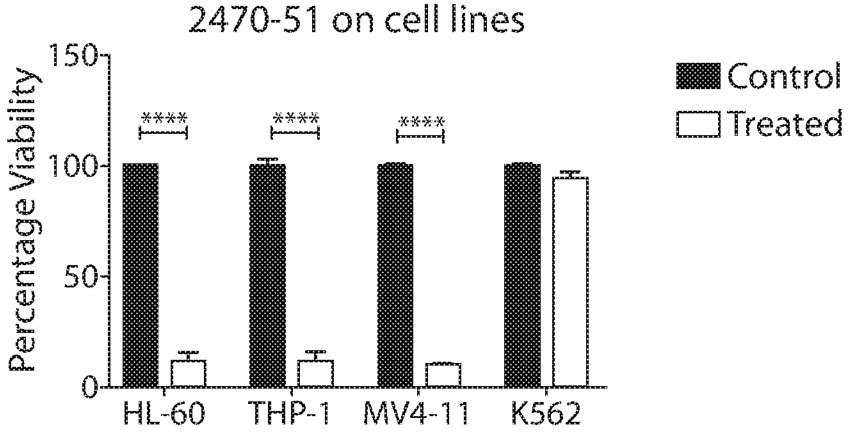
FIG. 5**C. Effect of compound 2470-51 on viability of four cell lines (HL-60, THP-1, MV4-11, and K562).
Figure 6:
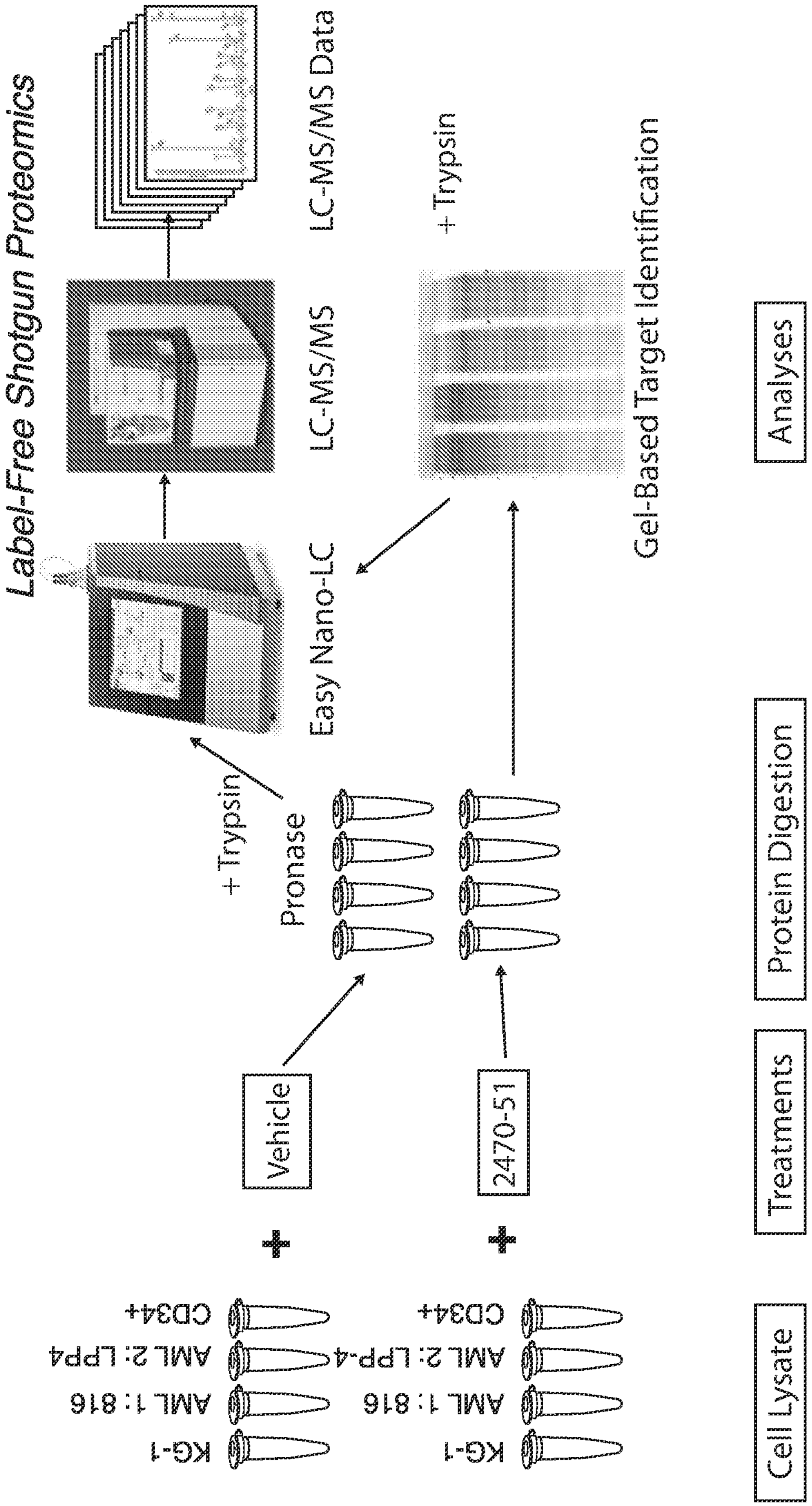
FIG. 6. This schematic illustrates the proteomics work flow in identifying protein targets for the compounds. AML cells (KG-1, AML 1:816, AML 2:LPP4) and health hematopoietic stem/progenitor cells (CD34+) were lysed and then mixed with either vehicle or a compound (e.g., 2470-51). Following compound-protein binding, pronase was used to cleave the proteins. Where the compound bound to proteins, this site was protected from pronase digestion. The peptides were then analyzed via gel-based target identification and label-free mass spectrometry.
Figure 7A:
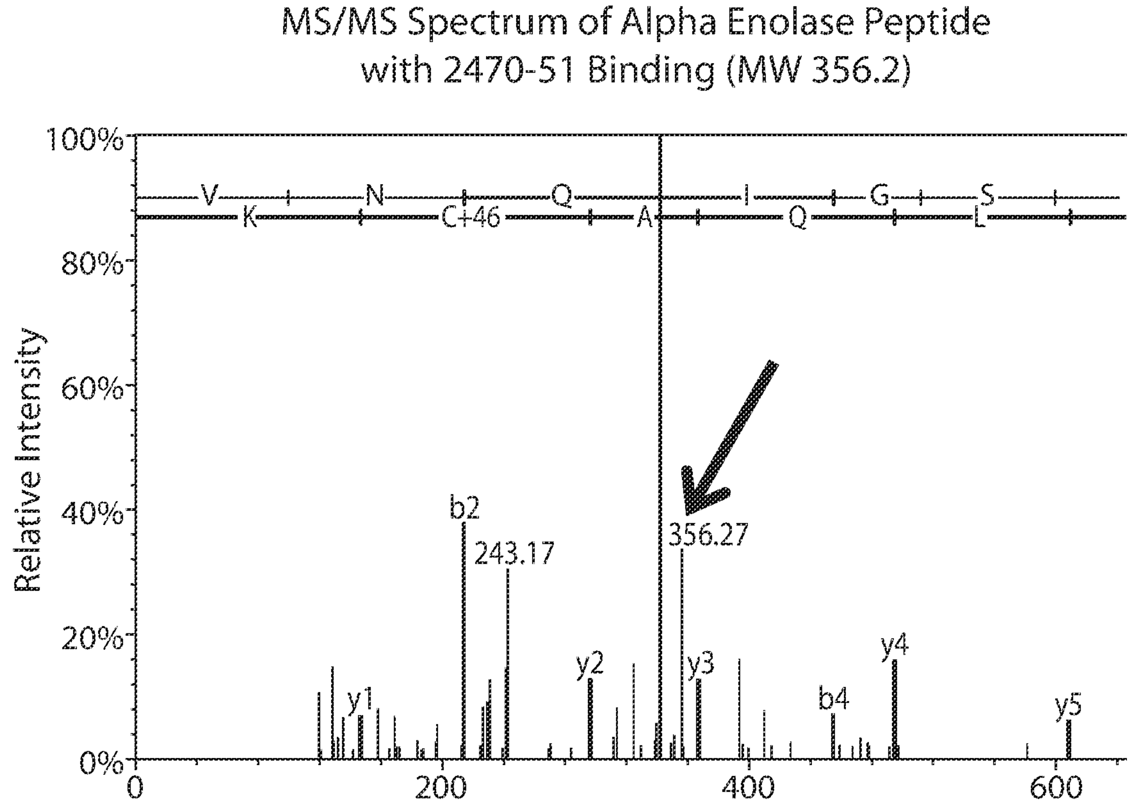
FIG. 7A. Using mass spectometry/mass spectometry (MS/MS) techniques, an alpha-enolase peptide was identified as covalently bound to compound 2470-51.
Figure 7B:
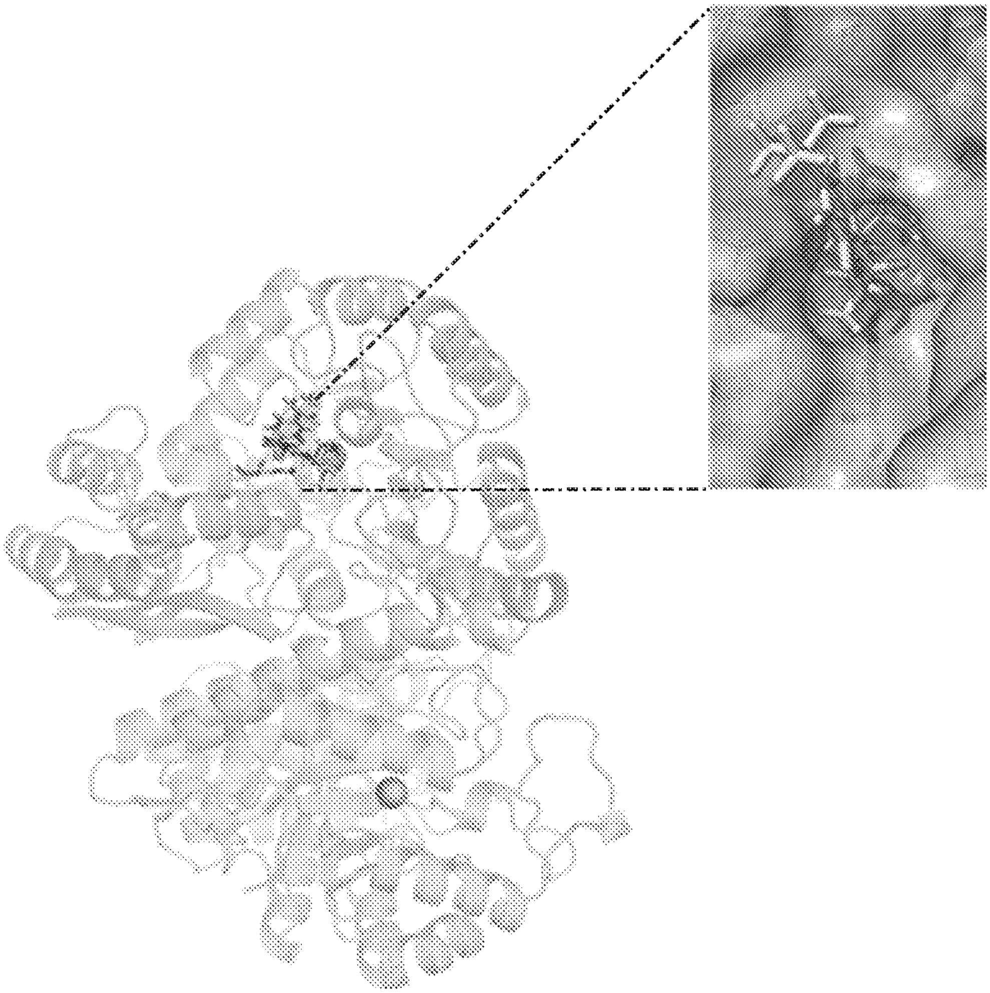
FIG. 7B. Computational docking using SWISS identified an active site binding pocket within alpha-enolase that the 2470-51 compound fit into.
Figure 8A:
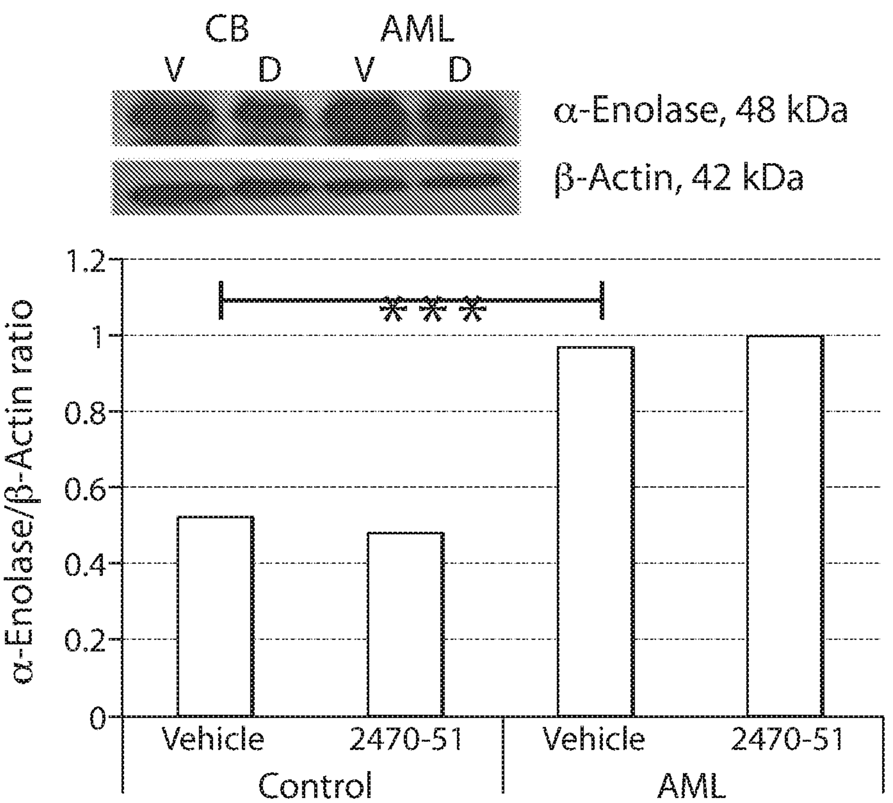
FIG. 8A. Enolase protein expression. AML cells showed higher protein expression of enolase compared to healthy human hematopoietic stem/progenitor cells (CD34+ cord blood (CB)). However, compound 2470-51 (denoted by D) did not change protein expression relative to vehicle (denoted by V) treatment. Thus, enolase correlates with malignant transformation, but is not changed by applying compounds of the present invention.
Figure 8B:
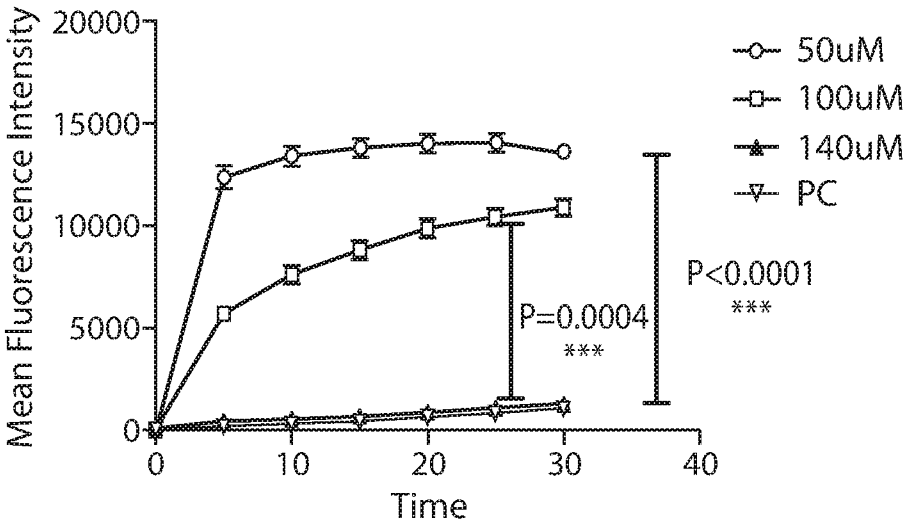
FIG. 8B. Effect of compounds on enolase enzyme activity. Although protein expression did not change, enolase enzymatic activity was reduced in a dose-dependent fashion by compound 2470-51.
Figure 9:
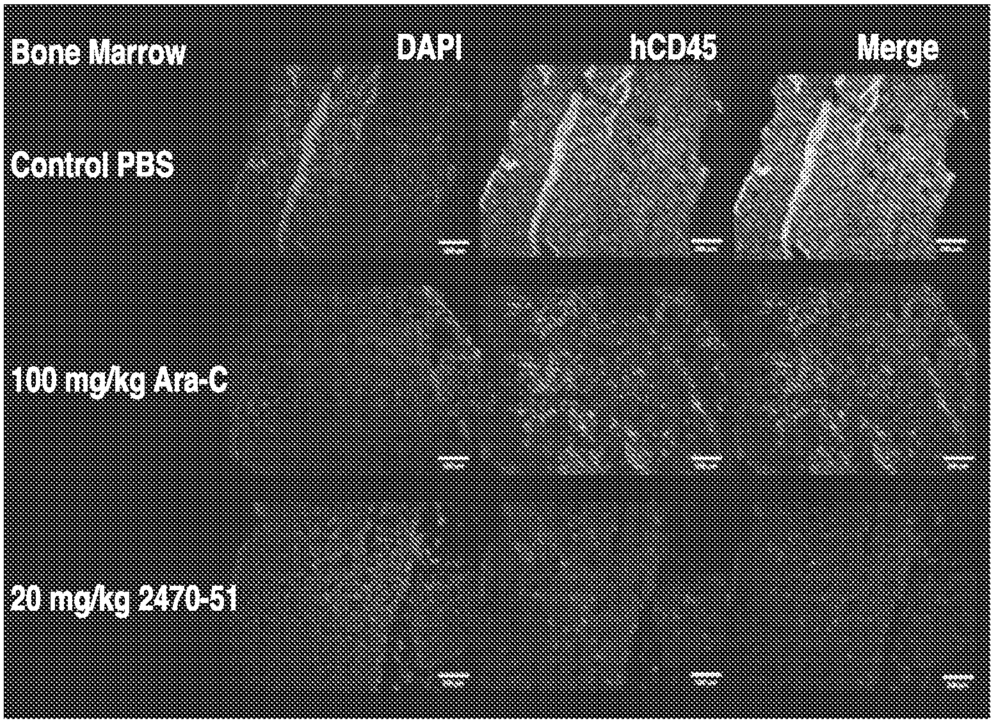
FIG. 9. Compound 2470-51 significantly reduced AML engraftment. Immunocompromised NRGS (NOD.CG-Rag1$^{tm1Mom}$Il2rg$^{tm1Wjl}$ (CMV-IL3, CSF2, KITLG) 1Eav/J) mice were given sub-lethal irradiation (200 cGy), followed by tail vein injection of primary human AML cells. At the end of four week, the animals were randomized into two-week treatment groups: vehicle-treated (PBS treatment control), cytarabine-treated 100 mg/kg IP TIW (positive treatment control), and 2470-51 20 mg/kg IP TIW. Bone marrows were examined for the presence of human CD45+ (green) and DAPI).

Compounds of Formula (I) were found to have significant toxicity in KG-1 cell lines (human acute myeloid leukemia cells) with minimal BMEC disruption at 50 µg/mL (see Table 1). The values given for percent toxicity to KG-1 cells is normalized to DMF. To compare the average AML-LSC toxicity vs. AML total toxicity, fresh human primary leukemia bone marrow mononuclear cells were treated with single doses of compounds, 2470-23 and 2470-51, at a single time point, and the killing of the AML leukemia stem cell (LSC) population versus the total AML cell population was quantified (FIG. 1). This demonstrates that both 2470 compounds were selectively toxic to the AML LSC fraction. Next, AML-LSC toxicity versus T lymphocyte (Jurkat) toxicity was investigated. The single-dose treatments 2470-23 and 2470-51 were compared on lymphoid (CD4+ Jurkat) versus myeloid (AML LSC) leukemia cells to demonstrate the specificity of these compounds for AML (FIG. 2). The single-dose treatments of 2470-23 and 2470-51 on normal healthy blood stem cells (sourced from fresh umbilical cord blood) versus AML LSC were also compared. As shown in FIG. 3, the inventive compounds do not deplete healthy stem cells while they do deplete the leukemia stem cells. These results indicate the specificity of action on diseased cells, with relative sparing of normal cells.

TABLE 1

Exemplary compounds with AML cell (KG1) toxicity and no BMEC disruption

| Compound | Structure | KG1 toxicity (50 µg/mL) | Exact Mass | LogP | tPSA ($Å^2$) | CLogP |
|---|---|---|---|---|---|---|
| 2470-40 | 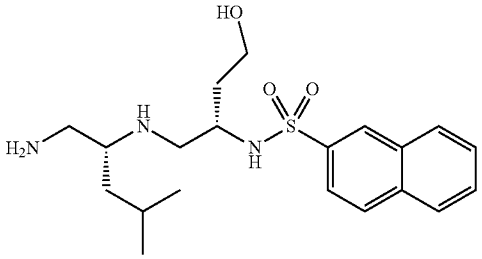 [SMILES: CC(C)C[C@H](CN)NC[C@H](CCO)NS(=O)(=O)c1ccc2ccccc2c1] | 37.4% | 393.21 | 2.25 | 104.45 | 2.3137 |
| 2470-49 | 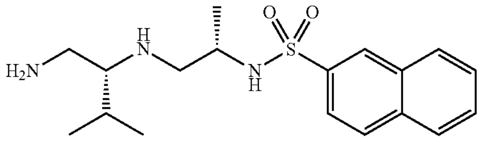 [SMILES: CC(C)[C@H](CN)NC[C@H](C)NS(=O)(=O)c1ccc2ccccc2c1] | 46.7% | 349.18 | 2.5 | 84.22 | 2.5647 |
| 2470-51 | 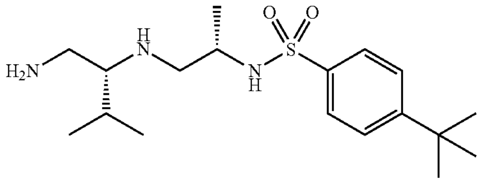 [SMILES: CC(C)[C@H](CN)NC[C@H](C)NS(=O)(=O)c1ccc(C(C)(C)C)cc1] | 93.2% | 355.23 | 3.26 | 84.22 | 3.2167 |
| 2470-15 | 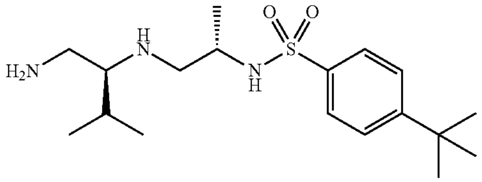 [SMILES: CC(C)[C@@H](CN)NC[C@H](C)NS(=O)(=O)c1ccc(C(C)(C)C)cc1] | 38.4% | 355.23 | 3.26 | 84.22 | 3.2167 |

TABLE 1-continued

Exemplary compounds with AML cell (KG1) toxicity and no BMEC disruption

| Compound | Structure | KG1 toxicity (50 μg/mL) | Exact Mass | LogP | tPSA ($Å^2$) | CLogP |
|---|---|---|---|---|---|---|
| 2470-23 | 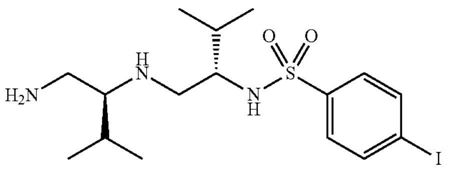 [SMILES: CC(C)[C@@H](CN)NC[C@@H](NS(=O)(=O)c1ccc(I)cc1)C(C)C] | 45.9% | 453.09 | 3.34 | 84.22 | 3.7441 |

Pharmacologic and ADME (absorption, distribution, metabolism, excretion) data for compound 2570-51 is shown in Table 2. Additional biological data for compounds of the present invention can be found in in the Figures and the Brief Description of the Drawings.

TABLE 2

Pharmacologic characteristics and ADME data for compound 2470-51

| Aqueous Solubility | Microsomal Stability, $t_{1/2}$ | Human plasma half-life | CYP450 inhibition | Plasma protein binding | PAMPA |
|---|---|---|---|---|---|
| >100 μM | mouse: 8 min<br>rat: 9 min<br>human: 33 min | >200 min | 2C9 > 20 μM<br>2D6 = 10.8 μM<br>3A4 > 20 μM | 80.5% | $1 \times 10^{-6}$ cm/s (moderate) |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I):

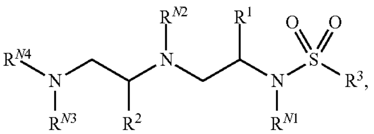

(I)

or a pharmaceutically acceptable salt thereof, wherein:

$R^1$ is optionally substituted $C_{1-6}$ alkyl, optionally substituted carbocyclyl, optionally substituted heterocyclyl, optionally substituted heterocyclylalkyl, or optionally substituted heteroaralkyl;

$R^2$ is optionally substituted $C_{1-6}$ alkyl, optionally substituted carbocyclyl, optionally substituted heterocyclyl, optionally substituted heterocyclylalkyl, or optionally substituted heteroaralkyl;

$R^3$ is optionally substituted alkyl, optionally substituted aryl, optionally substituted heteroaryl, optionally substituted carbocyclyl, or optionally substituted heterocyclyl; and $R^{N1}$, $R^{N2}$, $R^{N3}$, and $R^{N4}$ are each independently hydrogen, optionally substituted alkyl, optionally substituted aryl, or optionally substituted acyl; or optionally $R^{N3}$ and $R^{N4}$ are joined together with the intervening atoms to form optionally substituted heterocyclyl or optionally substituted heteroaryl;

provided that neither $R^1$ nor $R^2$ is substituted or unsubstituted benzyl.

2. The compound of claim 1, wherein $R^3$ is optionally substituted aryl.

3. The compound of claim 1, wherein the compound of Formula (I) is of Formula (II):

(II)

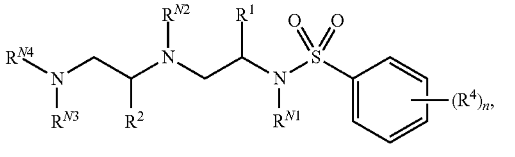

or a pharmaceutically acceptable salt thereof, wherein:

each instance of $R^4$ is independently hydrogen, halogen, —CN, —$NO_2$, —$N_3$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^{4a}$, —$N(R^{4b})_2$, or —$SR^{4c}$;

each instance of $R^{4a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or an oxygen protecting group;

each instance of $R^{4b}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group; or optionally two $R^{4b}$ are joined together with the intervening atoms to form optionally substituted heterocyclyl or optionally substituted heteroaryl;

each instance of $R^{4c}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a sulfur protecting group; and n is 0, 1, 2, 3, 4, or 5.

4. The compound of claim 3, wherein the compound of Formula (II) is of Formula (II-a):

(II-a)

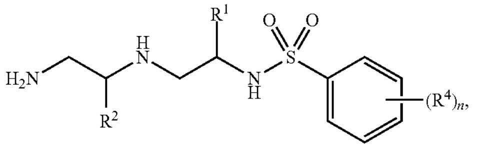

or a pharmaceutically acceptable salt thereof.

5. The compound of claim 3, wherein n is 1.

6. The compound of claim 3, wherein at least one instance of $R^4$ is halogen.

7. The compound of claim 3, wherein at least one instance of $R^4$ is optionally substituted $C_{1-6}$ alkyl.

8. The compound of claim 3, wherein the compound is selected from the group consisting of:

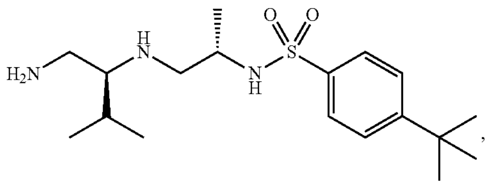
,

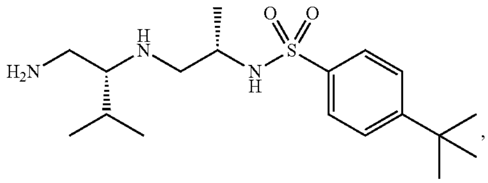
,

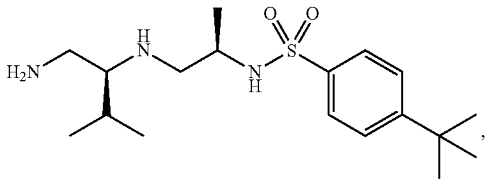
,

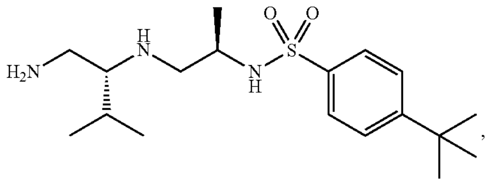
,

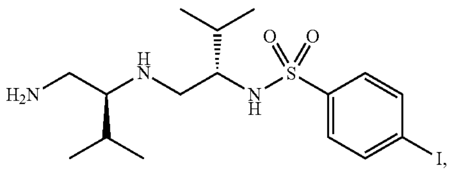
,

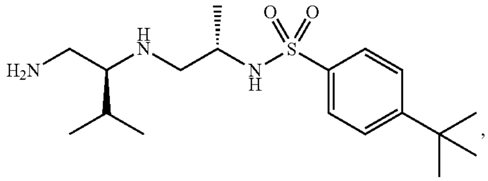
,

-continued

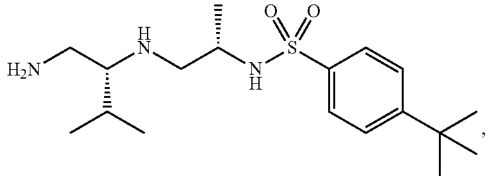

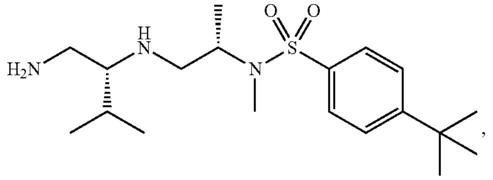

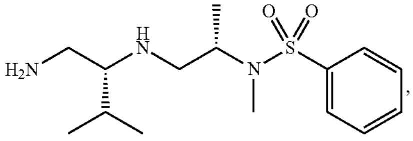

and pharmaceutically acceptable salts thereof.

9. The compound of claim 3, wherein the compound is of Formula (II-b) or (II-c):

(II-b)

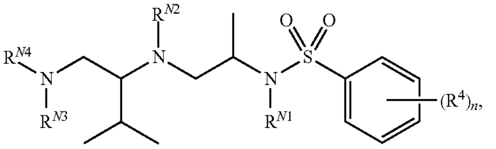

(II-c)

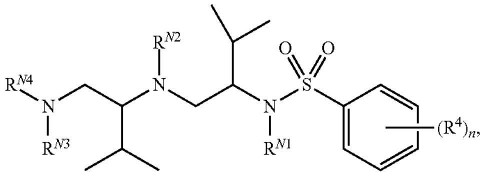

or a pharmaceutically acceptable salt thereof.

10. The compound of claim 3, wherein the compound is of Formula (II-d) or (II-e):

(II-d)

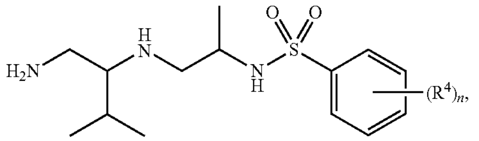

(II-e)

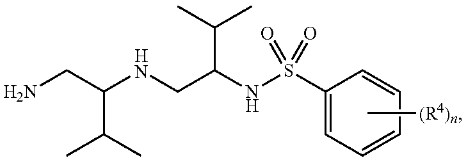

or a pharmaceutically acceptable salt thereof.

11. The compound of claim 3, wherein the compound is of Formula (II-f):

(II-f)

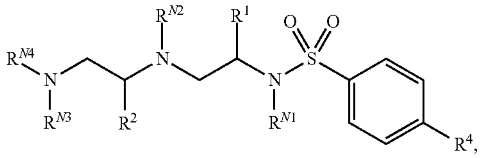

or a pharmaceutically acceptable salt thereof.

12. The compound of claim 3, wherein the compound is of Formula (II-g):

(II-g)

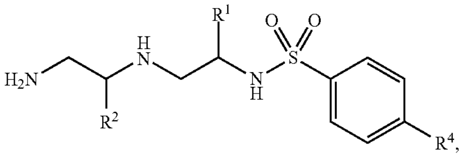

or a pharmaceutically acceptable salt thereof.

13. The compound of claim 3, wherein the compound is of Formula (II-h) or (II-i):

(II-h)

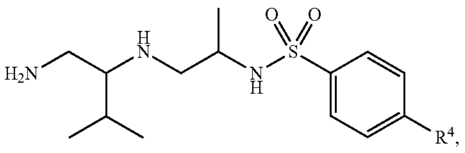

(II-i)

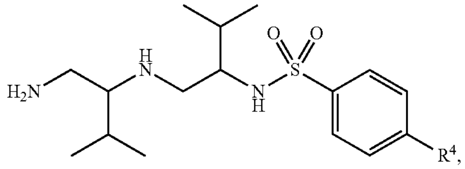

or a pharmaceutically acceptable salt thereof.

14. The compound of claim 3, wherein the compound is of Formula (II-j) or (II-k):

(II-j)

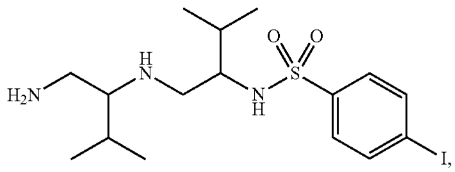

(II-k)

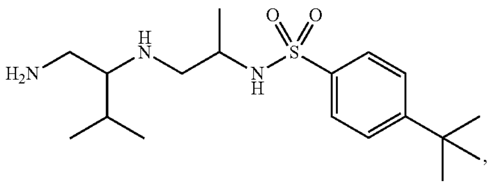 [SMILES: CC(C)[C@H](CN)NC[C@H](C)NS(=O)(=O)c1ccc(C(C)(C)C)cc1]

or a pharmaceutically acceptable salt thereof.

15. The compound of claim 3, wherein at least one instance of $R^4$ is —I.

16. The compound of claim 3, wherein at least one instance of $R^4$ is tert-butyl.

17. The compound of claim 3, wherein the compound is the following:

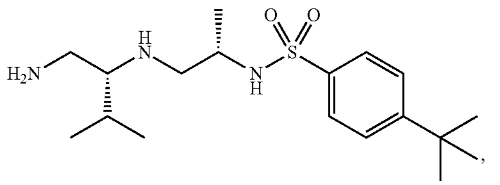

or a pharmaceutically acceptable salt thereof.

18. The compound of claim 1, wherein the compound of Formula (I) is of Formula (III):

(III)

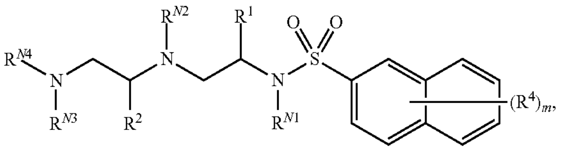

or a pharmaceutically acceptable salt thereof, wherein:

each instance of $R^4$ is independently hydrogen, halogen, —CN, —$NO_2$, —$N_3$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^{4a}$, —$N(R^{4b})_2$, or —$SR^{4c}$;

each instance of $R^{4a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or an oxygen protecting group;

each instance of $R^{4b}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group; or optionally two $R^{4b}$ are joined together with the intervening atoms to form optionally substituted heterocyclyl or optionally substituted heteroaryl;

each instance of $R^{4c}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a sulfur protecting group; and m is 1, 2, 3, 4, 5, 6, or 7.

19. The compound of claim 18, wherein the compound of Formula (III) is of Formula (III-a):

(III-a)

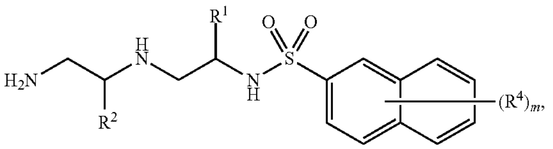

or a pharmaceutically acceptable salt thereof.

20. The compound of claim 18, wherein the compound is selected from the group consisting of:

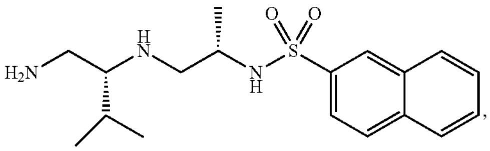

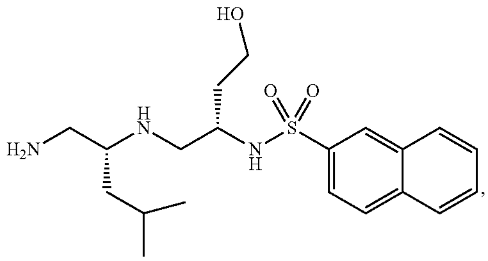

and pharmaceutically acceptable salts thereof.

21. The compound of claim 18, wherein the compound is of Formula (III-b) or (III-c):

(III-b)

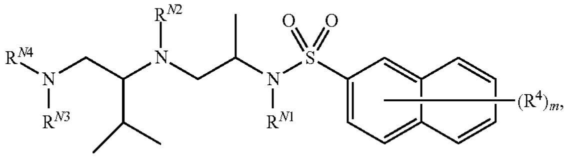

(III-c)

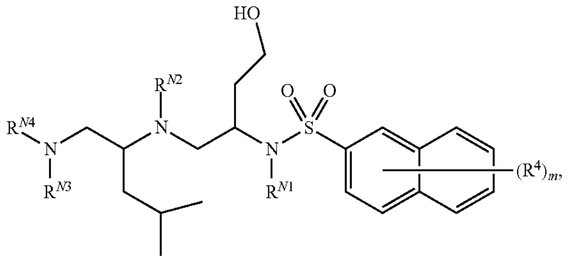

or a pharmaceutically acceptable salt thereof.

22. The compound of claim 18, wherein the compound is of Formula (III-d) or (III-e):

(III-d)

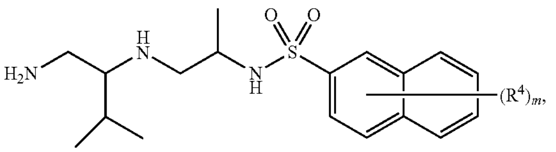

(III-e)

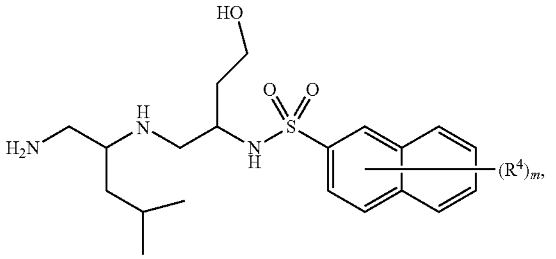

or a pharmaceutically acceptable salt thereof.

23. The compound of claim 18, wherein the compound is of Formula (III-f) or (III-g):

(III-f)

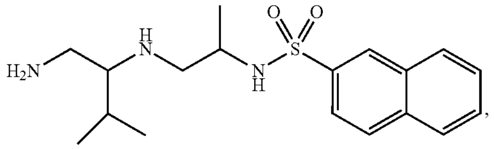

(III-g)

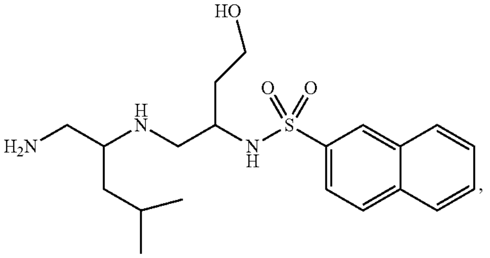

or a pharmaceutically acceptable salt thereof.

24. The compound of claim 18, wherein m is 0.

25. The compound of claim 1, wherein $R^1$ is optionally substituted $C_{1-6}$ alkyl.

26. The compound of claim 1, wherein $R^2$ is optionally substituted $C_{1-6}$ alkyl.

27. The compound of claim 1, wherein $R^{N1}$, $R^{N2}$, $R^{N3}$, and $R^{N4}$ are hydrogen.

28. The compound of claim 1, wherein $R^1$ is unsubstituted $C_{1-6}$ alkyl.

29. The compound of claim 1, wherein $R^1$ is selected from the group consisting of methyl, ethyl, propyl, butyl, iso-propyl, iso-butyl, sec-butyl, tert-butyl, $—CH_2OH$, $—CH_2CH_2OH$, $—CH(OH)CH_3$, $—CH_2CH(OH)CH_3$, $—CH_2SH$, $—CH_2CH_2SCH_3$, $—CH_2NH_2$, $CH_2(CH_2)_{1-4}NH_2$

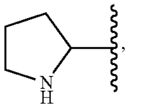 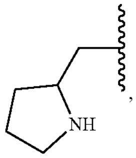 and 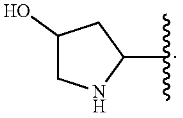

30. The compound of claim 1, wherein $R^1$ is selected from the group consisting of methyl, iso-propyl, and $—CH_2CH_2OH$.

31. The compound of claim 1, wherein $R^2$ is unsubstituted $C_{1-6}$ alkyl.

32. The compound of claim 1, wherein $R^2$ is selected from the group consisting of methyl, ethyl, propyl, butyl, iso-propyl, iso-butyl, sec-butyl, tert-butyl, $—CH_2OH$, $—CH_2CH_2OH$, $—CH(OH)CH_3$, $—CH_2CH(OH)CH_3$, $—CH_2SH$, $—CH_2CH_2SCH_3$, $—CH_2NH_2$, $—CH_2(CH_2)_{1-4}NH_2$,

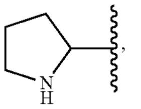 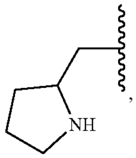 and 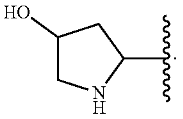

33. The compound of claim 1, wherein $R^2$ is iso-propyl or iso-butyl.

34. A pharmaceutical composition comprising a compound of claim 1, or a pharmaceutically acceptable salt thereof, and optionally a pharmaceutically acceptable excipient.

35. A kit comprising a compound of claim 1, or a pharmaceutically acceptable salt thereof, or a pharmaceutical composition thereof; and optionally instructions for administering the compound, the pharmaceutically acceptable salt thereof, or the pharmaceutical composition thereof.

36. A method of treating a proliferative disease in a subject, the method comprising administering to the subject a therapeutically effective amount of a compound of claim 1, or a pharmaceutically acceptable salt thereof.

37. The method of claim 36, wherein the proliferative disease is cancer.

38. The method of claim 37, wherein the cancer is a hematological cancer.

39. The method of claim 37, wherein the cancer is selected from the group consisting of leukemias, myeloproliferative neoplasms, lymphomas, and multiple myeloma.

40. The method of claim 37, wherein the cancer is leukemia.

41. The method of claim 37, wherein the cancer is acute myeloid leukemia (AML).

42. A method for inducing apoptosis of a cell in a subject or biological sample, the method comprising administering to the subject or biological sample a compound of claim 1, or a pharmaceutically acceptable salt thereof.

43. A method for inhibiting the enzymatic activity of an alpha-enolase protein, the method comprising contacting an alpha-enolase protein with a compound of claim 1, or a pharmaceutically acceptable salt thereof.

* * * * *